United States Patent
Fukuda et al.

(10) Patent No.: US 10,585,032 B2
(45) Date of Patent: Mar. 10, 2020

(54) URINE ANALYSIS SYSTEM, IMAGE CAPTURING APPARATUS, URINE ANALYSIS METHOD

(71) Applicant: SYSMEX CORPORATION, Kobe-shi, Hyogo (JP)

(72) Inventors: Masakazu Fukuda, Kobe (JP); Masamichi Tanaka, Kobe (JP); Yousuke Tanaka, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 22 days.

(21) Appl. No.: 15/715,190

(22) Filed: Sep. 26, 2017

(65) Prior Publication Data

US 2018/0017480 A1    Jan. 18, 2018

Related U.S. Application Data

(63) Continuation of application No. PCT/JP2016/052775, filed on Jan. 29, 2016.

(30) Foreign Application Priority Data

Mar. 31, 2015  (JP) .................................. 2015-071680
Oct. 7, 2015   (JP) .................................. 2015-199806

(51) Int. Cl.
  *G01N 15/14*      (2006.01)
  *G01N 33/493*    (2006.01)
  (Continued)

(52) U.S. Cl.
  CPC ........... *G01N 15/1463* (2013.01); *G01N 1/14* (2013.01); *G01N 15/14* (2013.01);
  (Continued)

(58) Field of Classification Search
  CPC ........... G01N 15/1463; G01N 21/6428; G01N 15/1436; G01N 15/1459; G01N 33/48792;
  (Continued)

(56) References Cited

U.S. PATENT DOCUMENTS 9,075,043 B2    7/2015  Mizumoto et al.
2007/0076190 A1  4/2007  Nakaya et al.
(Continued)

FOREIGN PATENT DOCUMENTS

CN    1727902 A     2/2006
CN    101762584 A   6/2010
(Continued)

OTHER PUBLICATIONS

The Japanese office action dated Jul. 2, 2019 in a counterpart Japanese patent application.

(Continued)

*Primary Examiner* — Amandeep Saini
(74) *Attorney, Agent, or Firm* — Metrolex IP Law Group, PLLC

(57) ABSTRACT

A urine analysis system according to an embodiment includes: a testing apparatus that measures particles included in a urine sample according to a flow cytometry method; an image capturing apparatus that captures images of particles in the urine sample to acquire particle images; and a management apparatus that receives a measurement result obtained by the testing apparatus and the particle images acquired by the image capturing apparatus. The management apparatus generates an order to capture an image of the urine sample based on the measurement result obtained by the testing apparatus. The image capturing apparatus executes the image capturing processing of the particles in the urine sample for which the image capturing order has (Continued)

been generated by the management apparatus, and transmits the acquired particle images to the management apparatus.

20 Claims, 38 Drawing Sheets

(51) Int. Cl.
G01N 33/52 (2006.01)
G01N 21/78 (2006.01)
G01N 33/483 (2006.01)
G01N 1/14 (2006.01)
G01N 21/64 (2006.01)
G01N 33/487 (2006.01)
G01N 15/00 (2006.01)
G01N 15/10 (2006.01)

(52) U.S. Cl.
CPC ..... *G01N 15/1436* (2013.01); *G01N 15/1459* (2013.01); *G01N 21/6428* (2013.01); *G01N 21/78* (2013.01); *G01N 33/483* (2013.01); *G01N 33/48792* (2013.01); *G01N 33/493* (2013.01); *G01N 33/52* (2013.01); *G01N 2015/0065* (2013.01); *G01N 2015/1006* (2013.01); *G01N 2021/6439* (2013.01); *G01N 2201/068* (2013.01)

(58) Field of Classification Search
CPC .......... G01N 1/14; G01N 15/14; G01N 21/78; G01N 33/52; G01N 33/493; G01N 33/483; G01N 2201/068; G01N 2015/0065; G01N 2015/1006; G01N 2021/6439
USPC ......................................... 382/133
See application file for complete search history.

(56) References Cited

U.S. PATENT DOCUMENTS

| | | | |
|---|---|---|---|
| 2007/0269897 A1 | 11/2007 | Tanaka et al. | |
| 2008/0212866 A1 | 9/2008 | Lett et al. | |
| 2009/0050821 A1* | 2/2009 | Tanaka | G01N 15/1459 250/458.1 |
| 2009/0191585 A1 | 7/2009 | Yamada et al. | |
| 2010/0111767 A1 | 5/2010 | Yonekura et al. | |
| 2010/0169811 A1 | 7/2010 | Yamada | |
| 2010/0242633 A1* | 9/2010 | McDevitt | G01N 1/2208 73/863.22 |
| 2010/0248374 A1 | 9/2010 | Kitagawa et al. | |
| 2014/0273082 A1 | 9/2014 | Cremins | |
| 2016/0291306 A1* | 10/2016 | Fukuda | G02B 21/241 |

FOREIGN PATENT DOCUMENTS

| | | | |
|---|---|---|---|
| CN | 101852716 A | 10/2010 | |
| CN | 101852798 A | 10/2010 | |
| CN | 102156088 A | 8/2011 | |
| CN | 102393705 A | 3/2012 | |
| CN | 103460054 A | 12/2013 | |
| EP | 2239568 A1 | 10/2010 | |
| EP | 2327977 A2 * | 6/2011 | ........... G01N 15/147 |
| EP | 2327977 A2 | 6/2011 | |
| EP | 2327977 A3 | 8/2017 | |
| JP | S56-154647 A | 11/1981 | |
| JP | S60-162955 A | 8/1985 | |
| JP | H07-294414 A | 11/1995 | |
| JP | H08-136438 A | 5/1996 | |
| JP | H08-297121 A | 11/1996 | |
| JP | H09281028 A | 10/1997 | |
| JP | H09-329596 A | 12/1997 | |
| JP | H11-248698 A | 9/1999 | |
| JP | 2002-188993 A | 7/2002 | |
| JP | 2006-138654 A | 6/2006 | |
| JP | 2007-093356 A | 4/2007 | |
| JP | 2007-309765 A | 11/2007 | |
| JP | 2009-128266 A | 6/2009 | |
| JP | 2009-174966 A | 8/2009 | |
| JP | 2010-032539 A | 2/2010 | |
| JP | 2010-054425 A | 3/2010 | |
| JP | 2010-512508 A | 4/2010 | |
| JP | 2010-107399 A | 5/2010 | |
| JP | 2010-151647 A | 7/2010 | |
| JP | 2010-236952 A | 10/2010 | |
| JP | 2011-133460 A | 7/2011 | |
| WO | 2009147931 A1 | 12/2009 | |
| WO | 2009148954 A2 | 12/2009 | |
| WO | 2011152193 A1 | 12/2011 | |
| WO | 2012128345 A1 | 9/2012 | |

OTHER PUBLICATIONS

The office action dated Jan. 25, 2019, in a counterpart Chinese patent application.
The office action dated Aug. 29, 2019 in a counterpart Chinese patent application.
The communication dated Sep. 20, 2019 in a counterpart European patent application.
Japanese Office action (JPOA) dated Nov. 12, 2019 in a related Japanese patent application.
Chinese Office action (CNOA) dated Dec. 18, 2019 in a counterpart Chinese patent application.

* cited by examiner

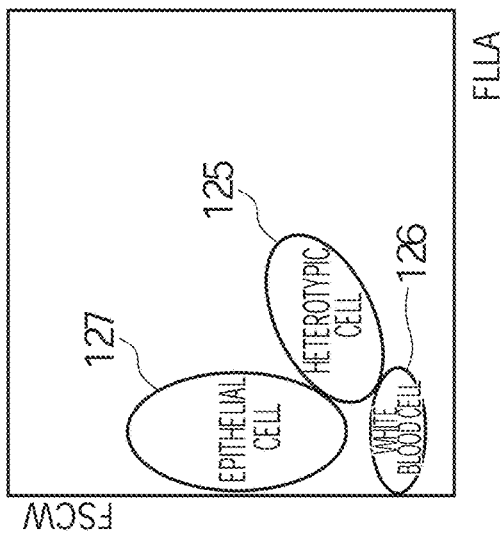
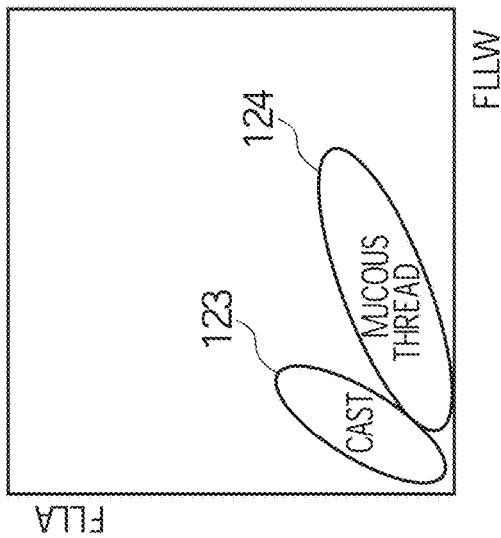
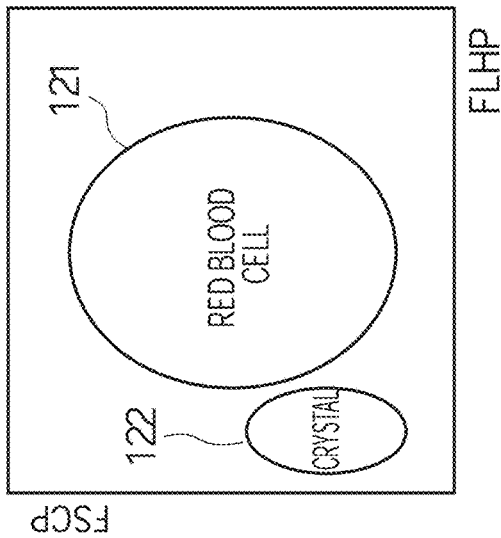
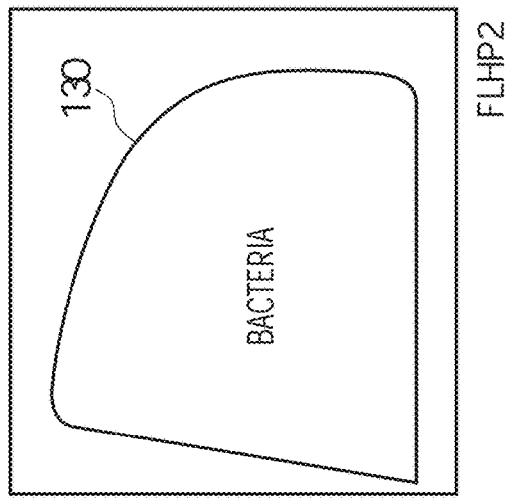
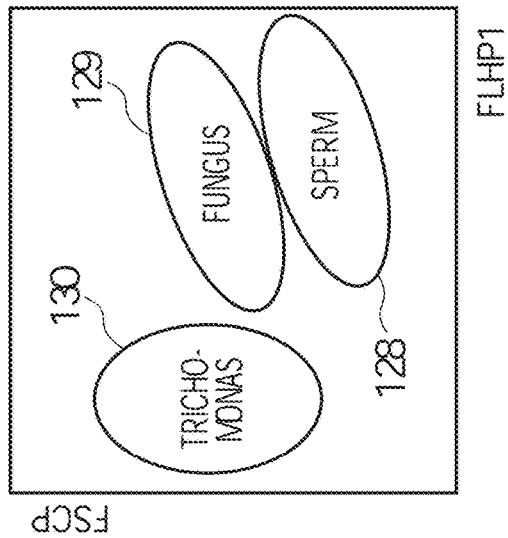

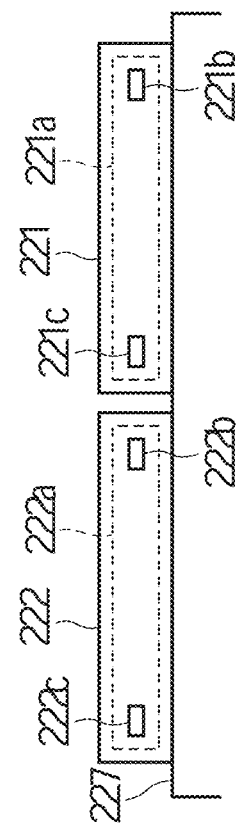
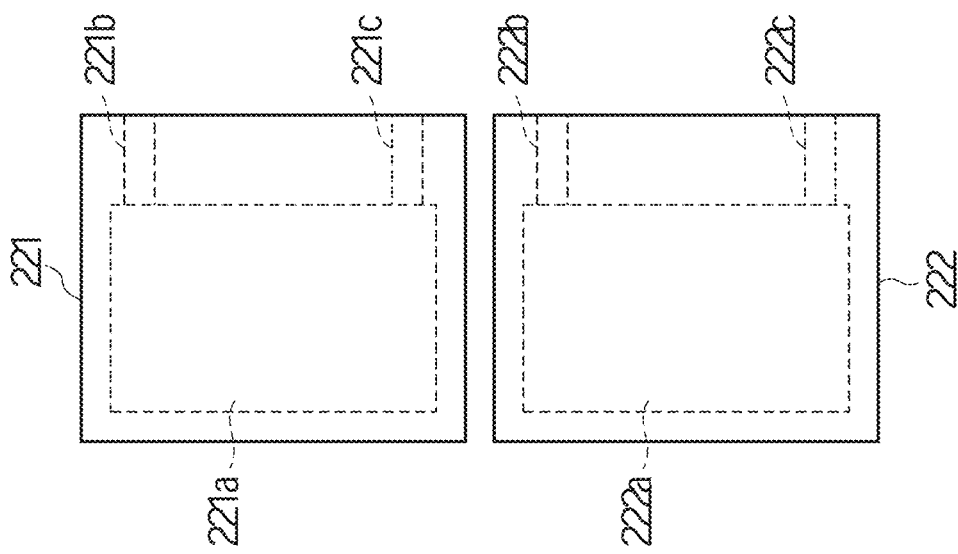

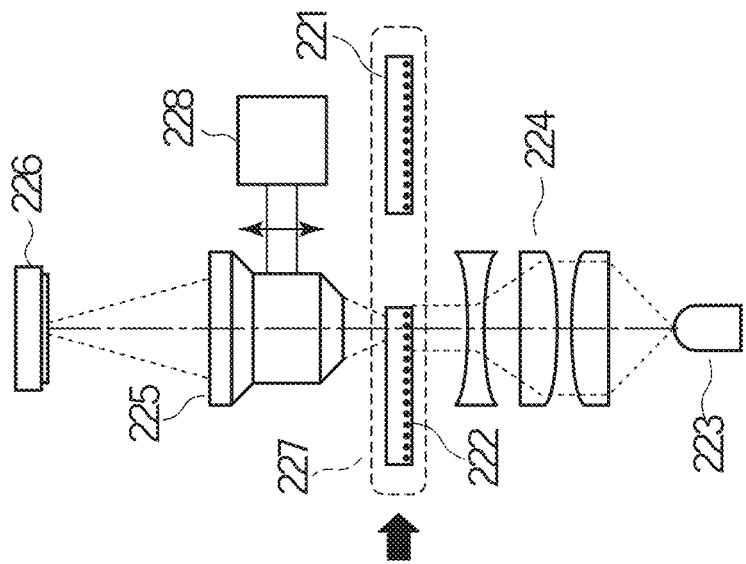
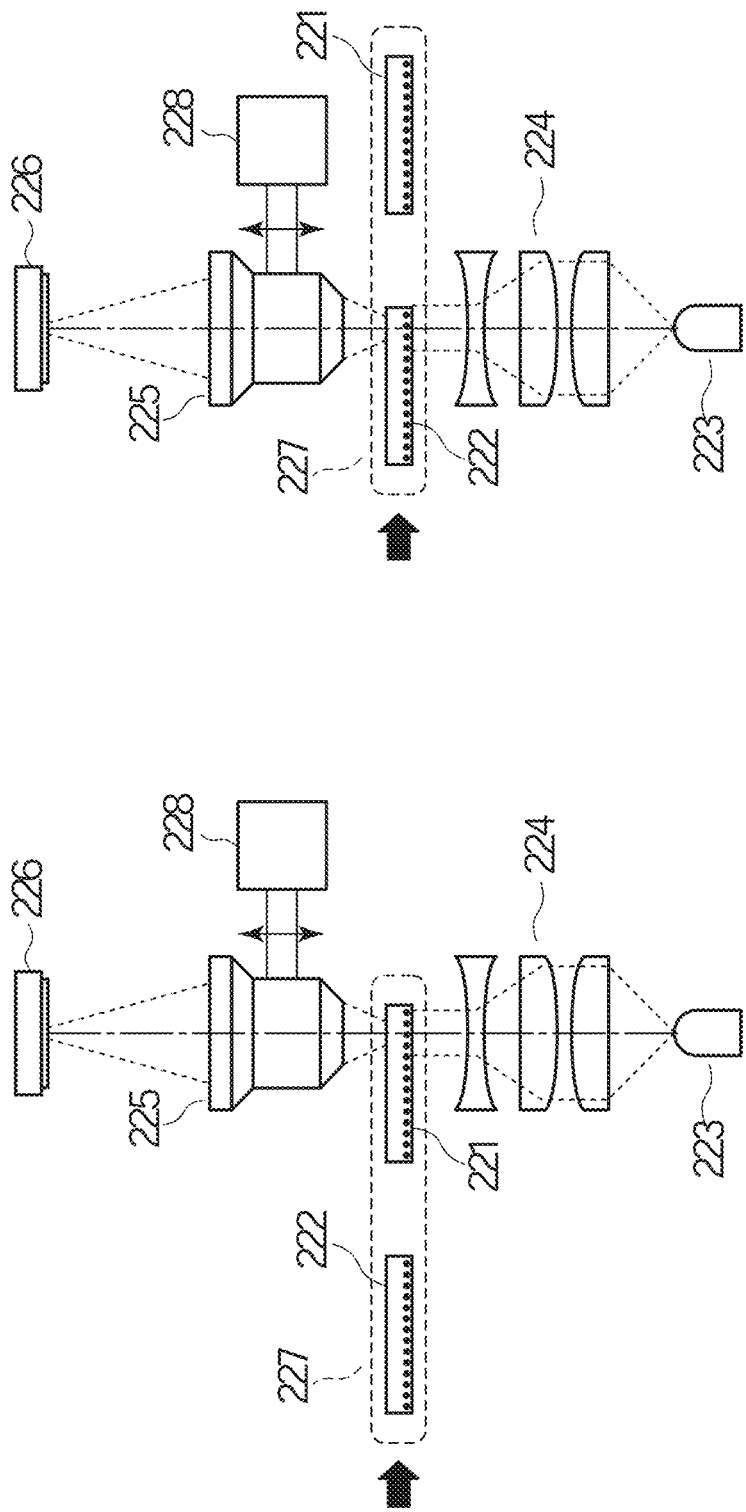

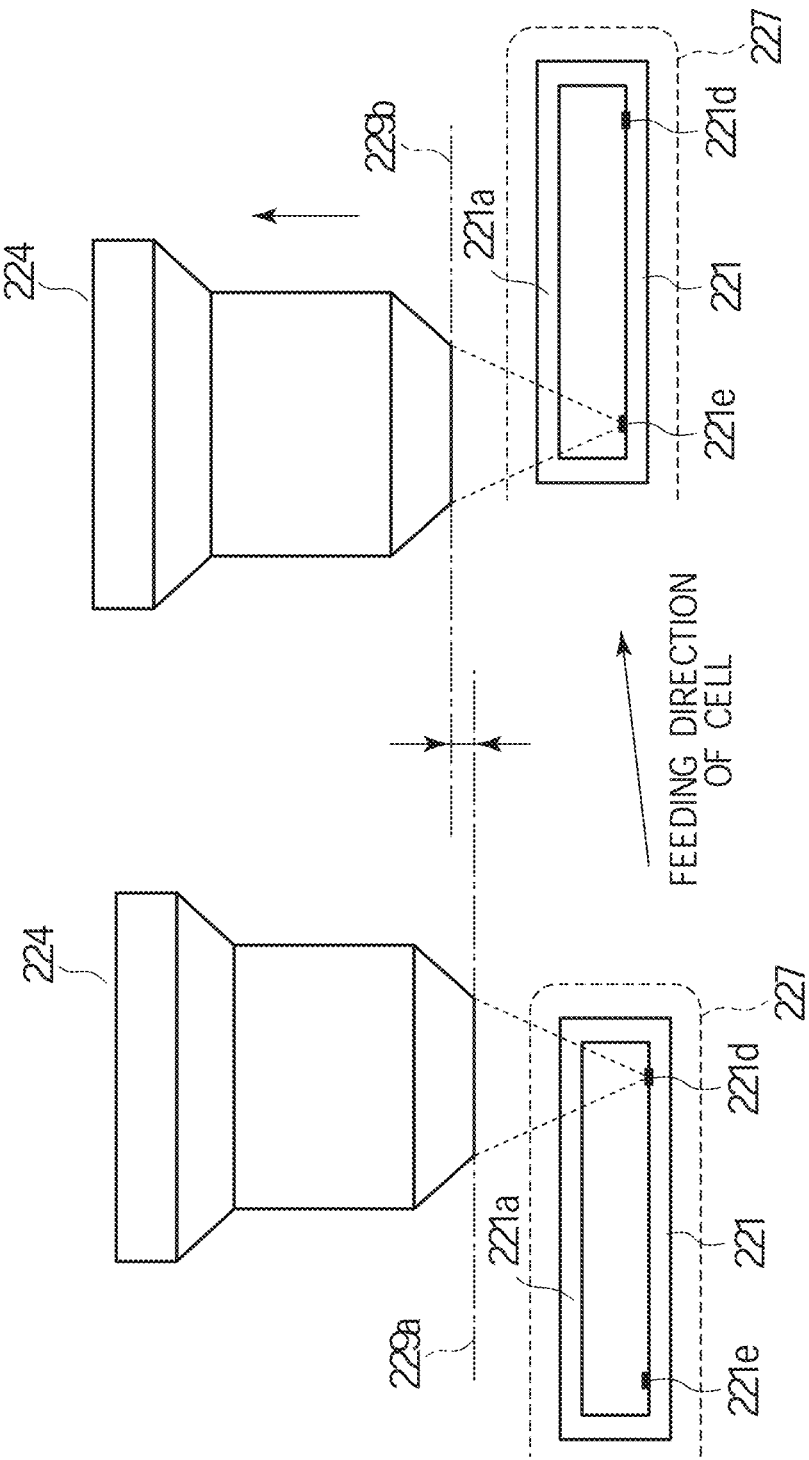

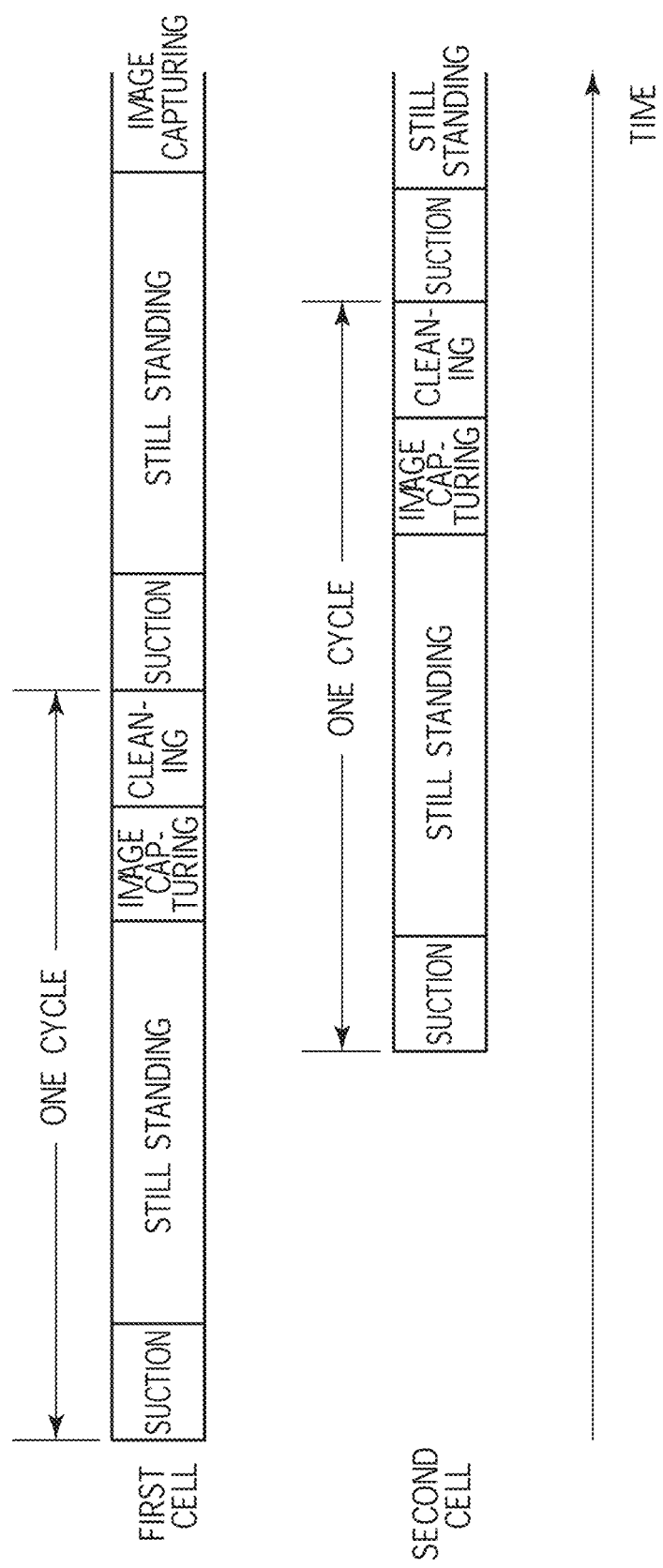

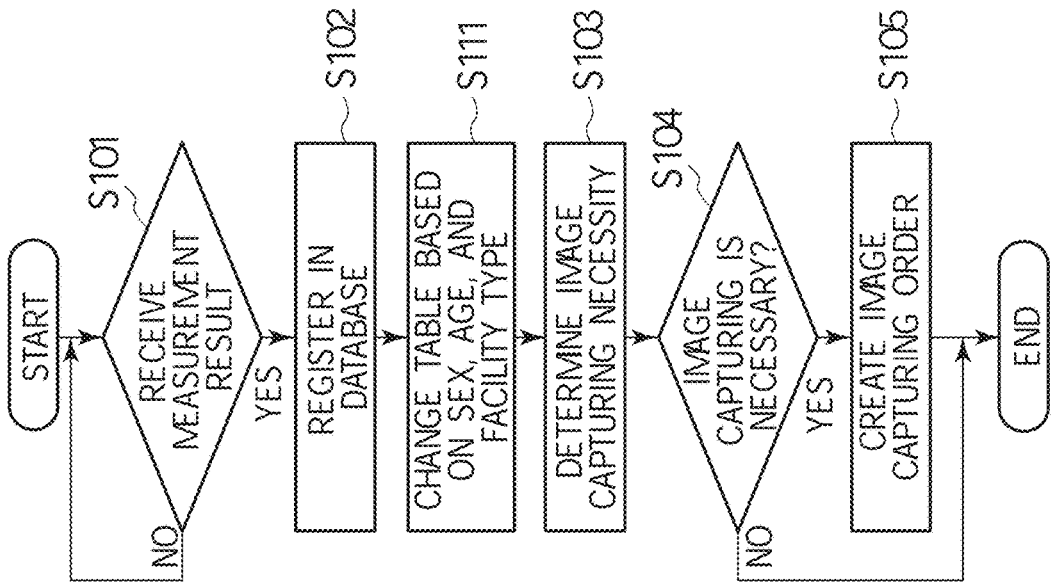

FIG. 15A FIRST CONDITION TABLE

| MEASUREMENT ITEM | THRESHOLD OF IMAGE CAPTURING NECESSITY |
|---|---|
| OCCULT BLOOD | +1 |
| PROTEIN | +1 |
| SULFUROUS ACID | +1 |
| WHITE BLOOD CELL | +1 |
| SUGAR | +1 |

FIG. 15B SECOND CONDITION TABLE

| MEASUREMENT ITEM | THRESHOLD OF IMAGE CAPTURING NECESSITY | CLOSE INSPECTION MODE CONDITION |
|---|---|---|
| OCCULT BLOOD | +1 | — |
| PROTEIN | +1 | ○ |
| SULFUROUS ACID | +1 | — |
| WHITE BLOOD CELL | +1 | — |
| SUGAR | +1 | — |

FIG. 15C PROCESSING OF MANAGEMENT APPARATUS

START
↓
S101 RECEIVE MEASUREMENT RESULT — NO (loop) / YES
↓
S102 REGISTER IN DATABASE
↓
S111 CHANGE TABLE BASED ON SEX, AGE, AND FACILITY TYPE
↓
S103 DETERMINE IMAGE CAPTURING NECESSITY
↓
S104 IMAGE CAPTURING IS NECESSARY? — NO / YES
↓
S105 CREATE IMAGE CAPTURING ORDER
↓
END

FIG. 16

URINE ANALYSIS SYSTEM, IMAGE CAPTURING APPARATUS, URINE ANALYSIS METHOD

CROSS REFERENCE TO RELATED APPLICATIONS

This application is a condition of application of International Application No. PCT/JP2016/052775, filed on Jan. 29, 2016, entitled "URINE ANALYSIS SYSTEM, IMAGE CAPTURING APPARATUS, CELL IMAGE CAPTURING APPARATUS, URINE ANALYSIS METHOD, MANAGEMENT APPARATUS, AND INFORMATION PROCESSING METHOD", which claims priority based on 35 USC 119 from prior Japanese Patent Applications Nos. 2015-071680 filed on Mar. 31, 2015, and 2015-199806 filed on Oct. 7, 2015, the entire contents of which are incorporated herein by reference.

BACKGROUND

The disclosure relates to a urine analysis system for analyzing a urine sample, an image capturing apparatus for capturing an image of the urine sample, a cell image capturing apparatus for capturing an image of a cell included in a liquid specimen, a urine analysis method, a management apparatus, and an information processing apparatus.

There is known an automatic analysis apparatus that analyzes particles in a urine specimen using a flow cytometry method (Japanese Patent Publication Application Nos. H09-329596, 2002-188993, and H08-136438). The automatic analysis apparatus that performs an analysis using the flow cytometry method is advantageous in that measurement can be quickly performed and particles in urine can be analyzed accurately because a large amount of the urine specimen can be processed by a flow cytometer in the measurement.

However, in the urine, in some case, mucous threads sometimes having a form like a cast and aggregates of bacteria, salts and the like are present. In a method of performing an analysis using the flow cytometer, these particles sometimes cannot be distinguished and accurately detected since scattered lights and fluorescent lights detected from the particles are similar to one another. Similarly, when crystal components and yeast-like funguses having a shape similar to red blood cells are present in the urine, these particles sometimes cannot be accurately detected.

Atypical cells are sometimes included in urine of a patient having a cancer in a urinary tract system. The atypical cells refer to malignant cells and malignant suspicious cells, and in other words, cells showing heteromorphism such as a nucleus increase accompanying an increase in the amount of nucleic acid and a chromatin increase. It is extremely clinically important for early finding of a kidney disease and cancer of a urinary tract system to detect atypical cells included in urine. However, in the method using the flow cytometer, the atypical cells in the urine sometimes cannot be distinguished from other urine particles and accurately detected.

Therefore, some of samples are sent to a reexamination, in which a smear is prepared after pretreatment such as concentration by centrifugation, staining, and the like, and a visual test on the prepared smear is performed by a laboratory technician using a microscope.

The pretreatment such as the concentration by the centrifugation, the staining, and the like and the preparation of the smear take labor and time. A large burden is imposed on the laboratory technician for the visual test of the prepared smear. It is demanded that the labor and time and the burden be reduced and particles in urine be efficiently and accurately distinguished.

SUMMARY

A first aspect of the disclosure relates to a urine analysis system. The urine analysis system according to this aspect includes: a testing apparatus that measures particles included in a urine sample according to a flow cytometry method; an image capturing apparatus that captures images of the urine sample to acquire images of particles in the urine sample; and a management apparatus that receives a measurement result obtained by the testing apparatus and the particle images acquired by the image capturing apparatus. The management apparatus generates an image capturing order for the urine sample based on the measurement result obtained by the testing apparatus. The image capturing apparatus executes the image capturing processing of the urine sample for which the image capturing order has been generated by the management apparatus, and transmits the acquired particle images to the management apparatus.

A second aspect of the disclosure relates to an image capturing apparatus. The image capturing apparatus according to this aspect includes: a suction unit or a suction device that sucks a urine sample; an image capturer that captures images of the urine sample sucked by the suction unit to acquire images of particles in the urine sample; and a controller that controls the suction unit and the image capturer. Based on a measurement result of the particles in the urine sample measured by a flow cytometry method, the controller controls the suction unit to suck the urine sample and controls the image capturer to capture an image of the urine sample sucked by the suction unit.

A third aspect of the disclosure relates to an image capturing apparatus. The image capturing apparatus according to this aspect includes: a cell to which a liquid specimen including particles is introduced; an image capturer that captures images of the liquid specimen introduced into the cell; and a processing unit that extracts images of particles included in the captured images acquired by the image capturer. The processing unit is configured to execute a normal mode for acquiring particle images by for causing the image capturer to capture a first number of images of the liquid specimen, and a close inspection mode for acquiring particle images by causing the image capturer to acquire a second number of images of the liquid specimen, the second number being larger than the first number, and executes any one of the normal mode and the close inspection mode based on which of a first condition set for the normal mode and a second condition set for the close inspection mode the liquid specimen of a test target satisfies.

It may be preferable that the cell comprises a first cell and a second cell into which the liquid specimen is introduced, wherein when the normal mode is executed, the cell image capturing apparatus introduces the liquid specimen into any one of the first cell and the second cell and acquires the captured images, and when the close inspection mode is executed, the cell image capturing apparatus introduces the liquid specimen into both of the first cell and the second cell and acquires the captured images.

It may be preferable that the first condition and the second condition each include at least one of sex, age, and a type of a facility that samples the liquid specimen.

A fourth aspect of the disclosure relates to a urine analysis method. The urine analysis method according to this aspect includes: measuring particles included in a urine sample according to a flow cytometry method; automatically sucking the urine sample based on a measurement result of the particles; capturing images the urine sample to acquire images of particles in the urine sample; and displaying the measurement result obtained by the flow cytometry method and the particle images in a comparable manner.

A fifth aspect of the disclosure relates to a management apparatus communicably connected to a first testing apparatus that measures particles in a urine sample according to a flow cytometry method, a second testing apparatus that measures a chemical component in the urine sample using test paper, and an image capturing apparatus that captures images of the particles in the urine sample to acquire images of particles in the urine sample. The management apparatus according to this aspect includes: a controller that receives a first measurement result of the particles in the urine sample obtained by the first testing apparatus, a second measurement result of the chemical component in the urine sample obtained by the second testing apparatus, and the particle images acquired by the image capturing apparatus; and a display unit. The controller causes the display unit to display, on one screen, the particle images and at least one of the first measurement result and the second measurement result.

It may be preferable that the controller causes the particle images to be displayed on the screen with the particle images divided into classes defined by a predetermined indicator.

It may be preferable that the predetermined indicator is size of the particles.

It may be preferable that, in the case where the urine sample contains a particle determined as an error in classification by the first testing apparatus, the controller further displays information indicating the particle determined as the error in the classification when displaying the first measurement result.

It may be preferable that the controller is configured to cause the screen to display a comment field for the urine sample, and when the urine sample contains a particle determined as an error in classification by the first testing apparatus, displays a detail of the classification error in the comment field.

It may be preferable that the management apparatus further comprises an input unit, wherein the controller receives input of a new comment through the input unit in the comment field.

It may be preferable that the management apparatus further comprises an input unit, wherein when one of the classes displayed on the screen is selected through the input unit, the controller causes the display unit to display, on one screen, particle images included in the one class, a classification operation region for inputting kinds of particles presented in the particle images via the input unit, and at least one of the first measurement result and the second measurement result.

It may be preferable that the image capturing apparatus captures images of the urine sample to acquire the captured images and acquires the particle images from the captured images, and when one of the particle images is selected as a classification target through the input unit, the controller displays, on the screen, the captured image that includes the selected particle image and surroundings of the particle image.

It may be preferable that the controller displays the selected particle image distinguishably in the captured images displayed on the screen.

It may be preferable that the controller causes the display unit to display a classification result input via the input unit in the classification operation region.

It may be preferable that the image capturing apparatus captures images of the urine sample to acquire the captured images and acquires the particle images from the captured images, the management apparatus further comprises an input unit, and when receiving a region corresponding to a cell in the captured image via the input unit, the controller acquires anew, as a particle image, an image in the region received via the input unit.

A sixth aspect of the disclosure relates to an information processing method. The information processing method according to this aspect includes: receiving a first measurement result obtained by measuring particles in a urine sample according to a flow cytometry method, a second measurement result obtained by measuring a chemical component in the urine sample using test paper, and particle images acquired by capturing images of particles in the urine sample; and displaying, on one screen, the particle images and at least one of the first measurement result and the second measurement result.

A seventh aspect of the disclosure relates to a management apparatus communicably connected to a testing apparatus that classifies and counts particles in a urine sample according to a flow cytometry method and an image capturing apparatus that captures images of the urine sample to acquire images of particles in the urine sample. The management apparatus according to this aspect includes: a controller that receives respective count values of various kinds of the particles in the urine sample obtained by the testing apparatus and the particle images acquired by the image capturing apparatus; an input unit; and a display unit. The controller causes the display unit to display the count values of the kinds of the particles and the particle images on one screen and receives information on the particles in the urine sample via the input unit. For each of the kinds of particles classified by the testing apparatus, when not receiving information on the kind of particles via the input unit, the controller causes the display unit to display, as a test result, the count value of the kind of particles obtained by the testing apparatus, or when receiving the information on the kind of particles via the input unit, the controller causes the display unit to display, as the test result, a count value based on the information on the kind of particles received via the input unit.

It may be preferable that, when receiving validation of a count value displayed on the display unit as the test result via the input unit, the controller sets the validated count value as a test result reportable to an outside.

According to one or more of the above described aspects, it is possible to proceed with highly accurate diagnosis of urine without being requested to perform complicated work.

Effects and significances of the present disclosure will be made apparent from the following explanation of embodiments. However, the embodiments explained below are only examples in carrying out the invention. The invention is not limited by the embodiments explained below.

BRIEF DESCRIPTION OF DRAWINGS

FIGS. 3A to 3E are diagrams illustrating measurement results of particles of the testing apparatus according to the first embodiment;

FIGS. 5A and 5B are respectively a plan view and a side view illustrating the configurations of a first cell and a second cell according to the first embodiment;

FIGS. 6A and 6B are diagrams illustrating the operation of the image capturing unit according to the first embodiment;

FIGS. 7A and 7B are diagrams illustrating a control method of the image capturer according to the first embodiment;

FIG. 8 is a timing chart of an image capturing operation according to the first embodiment;

FIGS. 15A and 15B are respectively diagrams illustrating the configurations of first and second condition tables referred to in necessity determination for generation of an image capturing order according to the second embodiment;

FIG. 15C is a flowchart for explaining image capturing order generation processing of a management apparatus according to a modification;

FIG. 16 is a diagram illustrating the configuration of a list screen according to a third embodiment;

Figure 1:
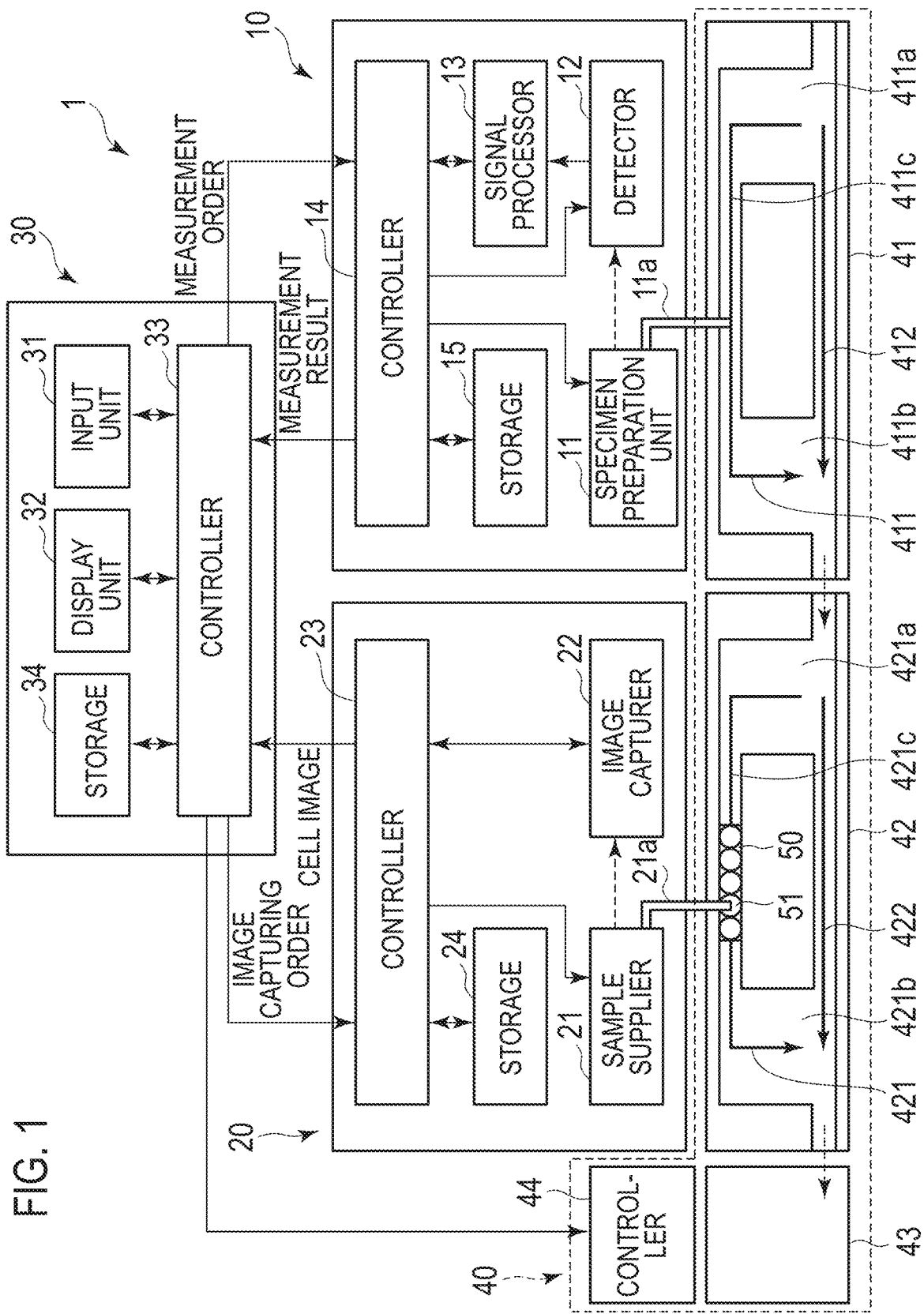
FIG. 1 is a diagram illustrating the configuration of a urine analysis system according to a first embodiment.

However, the drawings are solely for explanation and do not limit the scope of the invention.

DETAILED DESCRIPTION

Embodiments are explained with reference to drawings. In the respective drawings referenced herein, the same constituents are designated by the same reference numerals and duplicate explanation concerning the same constituents is basically omitted. All of the drawings are provided to illustrate the respective examples only. No dimensional proportions in the drawings shall impose a restriction on one or more embodiments. For this reason, specific dimensions and the like should be interpreted with the following descriptions taken into consideration. In addition, the drawings may include parts whose dimensional relationship and ratios are different from one drawing to another.

One or more embodiments are applied to a urine analysis system that analyzes a urine sample including particles such as blood cells, bacteria, casts, and epithelial cells. The urine sample serving as a measurement target includes, besides excreted urine, urine sampled from a living organism such as urine in a bladder.

First Embodiment

As illustrated in FIG. 1, urine analysis system 1 includes testing apparatus (flow cytometer) 10, image capturing apparatus 20, management apparatus 30, and conveyance apparatus 40. Testing apparatus 10 is a sediment device that classifies and counts particles included in a urine sample. Image capturing apparatus 20 captures images of the particles included in the urine sample. Note that in this disclosure, the particle images are also referred to as cell images.

Management apparatus 30 receives and manages a measurement result obtained by testing apparatus 10 and the cell images acquired by image capturing apparatus 20. Management apparatus 30 transmits a measurement order to testing apparatus 10 and transmits an image capturing order to image capturing apparatus 20 based on the measurement result obtained from testing apparatus 10. Conveyance apparatus 40 conveys the urine sample to testing apparatus 10 and image capturing apparatus 20 based on the measurement order and the image capturing order received from management apparatus 30. The urine sample is stored in sample container 51.

Conveyance apparatus 40 conveys sample rack 50, which holds sample containers 51, to testing apparatus 10 and image capturing apparatus 20.

Barcodes are respectively stuck to sample racks 50 and sample container 51. Sample rack 50 is identified by the barcode stuck to sample rack 50. Urine samples stored in sample containers 51 are identified by the barcodes stuck to sample containers 51. The barcodes stuck to sample containers 51 retain identification information of the urine samples.

Testing apparatus 10 includes specimen preparation unit 11, optical detector 12, signal processor 13, controller 14, and storage 15.

Specimen preparation unit 11 or a specimen preparation device includes suction unit 11a or a suction device that sucks a urine sample. Suction unit 11a includes a pipe-like suction tube. Specimen preparation unit 11 sucks the urine sample from sample container 51 with suction unit 11a. Specimen preparation unit 11 mixes a reagent in the urine sample sucked by suction unit 11a and prepares a measurement specimen. The reagent mixed in the urine sample is a staining solution containing a pigment for staining particles in the urine sample or a diluent.

A staining solution for staining particles not having nucleic acid (hereinafter, "nucleus-less components") is a fluorescent pigment that more easily combines with lipid and protein of a cell membrane than the nucleic acid. A pigment not affecting a form of red blood cells is desirable. The diluent to be mixed is a reagent containing a buffer agent as a main component. The diluent contains a buffer agent having pH for obtaining a stable fluorescent light signal without hemolyzing red blood cells. The staining solution and the diluent are mixed in the urine sample, whereby cell membranes or protein of the nucleus-less components in the urine sample is stained.

As a staining solution for staining particles having nucleic acid (hereinafter, "components with nucleuses"), a fluorescent pigment more easily combining with the nucleic acid than lipid and protein is selected. A diluent to be mixed is a reagent for damaging a cell membrane and promoting membrane permeation of the staining solution. The diluent contains a surface active agent. The red blood cell is hemolyzed and foreign matters such as chips of the red blood cells are contracted by the surface active agent. The staining solutions and the diluents are mixed in the urine sample, whereby the particles having nucleic acids in the urine sample are stained.

Detector 12 measures the measurement specimen prepared by specimen preparation unit 11.

Figure 2:
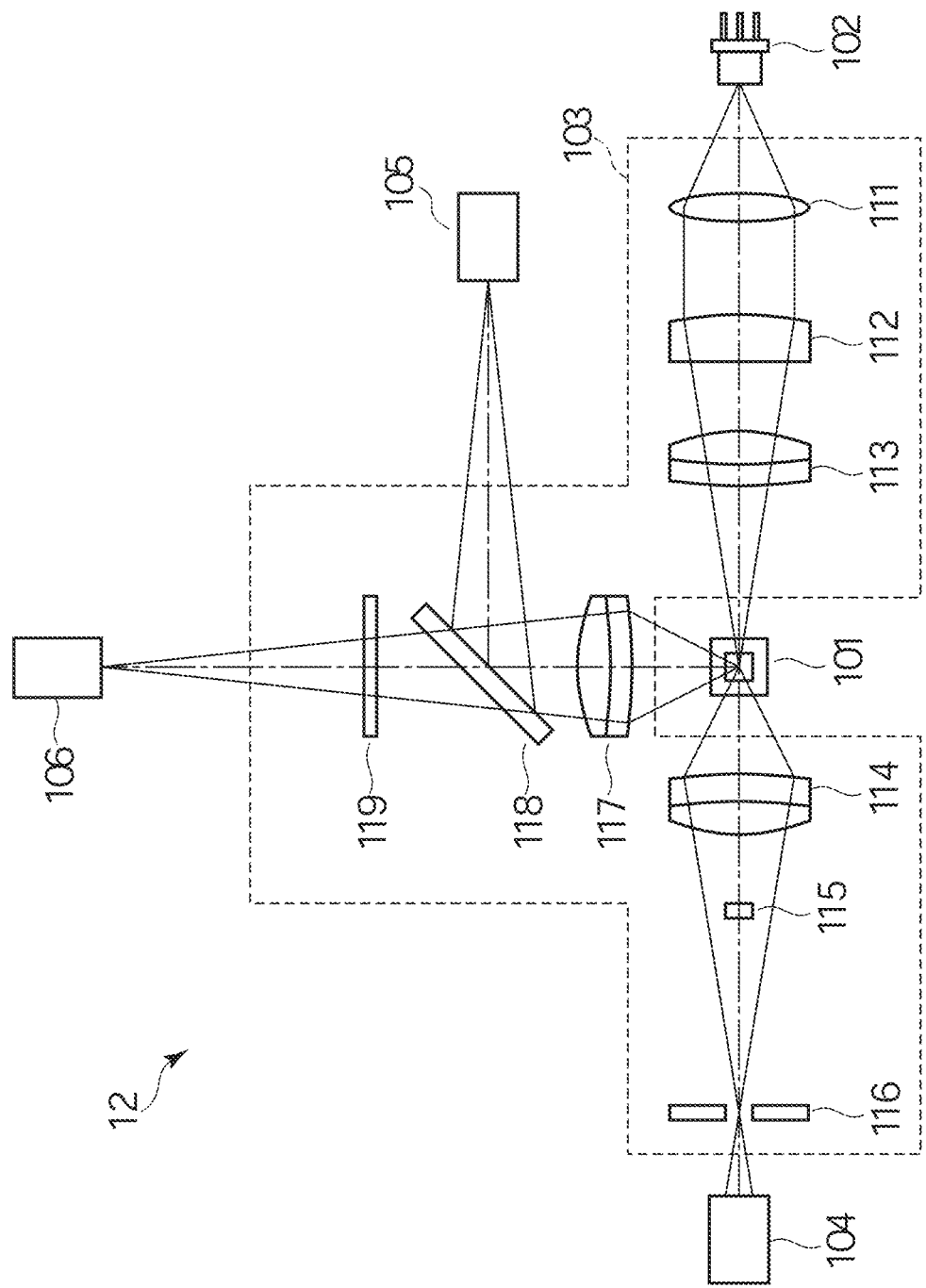
FIG. 2 is a schematic diagram illustrating the configuration of a detector of a testing apparatus (a flow cytometer) according to the first embodiment.

As illustrated in FIG. 2, detector 12 includes flow cell 101, light source 102, optical system 103, and light receivers 104 to 106. Flow cell 101 feeds the measurement specimen in one direction in a state in which the measurement specimen is surrounded by sheath liquid. Light source 102 is formed from, for example, a laser diode and emits light having a predetermined wavelength. Optical system 103 irradiates light emitting from light source 102 on a sample flow in flow cell 101. Optical system 103 guides front scattered light generated from the particles in flow cell 101 to light receiver 104. Optical system 103 guides side scattered light and side fluorescent light generated from the particles respectively to light receivers 105 and 106.

Optical system 103 includes collimator lens 111, cylindrical lens 112, condenser lens 113, condensing lens 114, beam stopper 115, pinhole 116, condensing lens 117, dichroic mirror 118, and optical filter 119.

Collimator lens 111 converts light emitted from light source 102 into parallel light. Cylindrical lens 112 and condenser lens 113 shape the light transmitted through collimator lens 111 into a shape wide in a direction perpendicular to the flow of the measurement specimen and apply the shaped light to the sample flow in flow cell 101. Consequently, front scattered light is generated in the front of the particles flowing in flow cell 101 and side scattered light and fluorescent light are generated on the side of the particles flowing in flow cell 101.

Condensing lens 114 condenses the front scattered light in the position of pinhole 116. Beam stopper 115 blocks the light transmitted through flow cell 101 without being applied to particles in the measurement specimen. Light receiver 104 receives the front scattered light passed through pinhole 116. Light receiver 104 includes, for example, a photodiode. Light receiver 104 amplifies a detection signal with an amplifier, generates a front scattered light signal based on the front scattered light, and outputs the generated front scattered light signal to signal processor 13 illustrated in FIG. 1.

Condensing lens 117 causes the side scattered light and the fluorescent light to respectively converge. Dichroic mirror 118 reflects the side scattered light transmitted through condensing lens 117. Light receiver 105 receives the side scattered light reflected by dichroic mirror 118. Light receiver 105 includes, for example, a photodiode or a photomultiplier tube. Light receiver 105 amplifies a detection signal with an amplifier, generates a side scattered light signal based on the side scattered light, and outputs the generated side scattered light signal to signal processor 13 illustrated in FIG. 1.

Dichroic mirror 118 transmits the fluorescent light transmitted through condensing lens 117. Optical filter 119 removes light in a wavelength band, which is noise, from the fluorescent light transmitted through dichroic mirror 118.

Light receiver 106 receives the fluorescent light transmitted through optical filter 119. Light receiver 106 includes, for example, a photomultiplier. Light receiver 106 amplifies a detection signal with an amplifier, generates a fluorescent light signal based on the fluorescent light, and outputs the generated fluorescent light signal to signal processor 13.

Light receivers 104, 105, and 106 are capable of switching light reception sensitivity between low sensitivity and high sensitivity by switching a driving voltage in photoelectric conversion or with the amplifiers. Light receivers 104 to 106 respectively generate, while the measurement specimen flows in flow cell 101, signals of the lights in the case of the low light reception sensitivity and signals of the lights in the case of the high light reception sensitivity and output the signals to signal processor 13 illustrated in FIG. 1.

Referring back to FIG. 1, signal processor 13 processes the signals respectively output from light receivers 104 to 106 and acquires signal waveforms of the front scattered light, the side scattered light, and the fluorescent light generated from the particles passing through flow cell 101. That is, signal processor 13 acquires, for each of the particles (red blood cells, white blood cells, epithelial cells, casts, bacteria, etc.) included in the measurement specimen, signal waveforms corresponding to the lights. Signal processor 13 outputs data of the acquired signal waveforms to controller 14.

Controller 14 includes an arithmetic processing circuit such as a CPU. Storage 15 includes memories such as a ROM, a RAM, and a hard disk. Storage 15 retains various kinds of information necessary for control by controller 14. Storage 15 is also used as a work region when controller 14 performs control. Controller 14 controls the components in testing apparatus 10 according to a computer program stored in storage 15. Controller 14 causes storage 15 to store the data of the signal waveforms of the particles acquired from signal processor 13. Controller 14 calculates, concerning the signal waveforms of the front scattered light, the side scattered light, and the fluorescent light, characteristic parameters such as peak values, widths, and areas. Controller 14 causes storage 15 to store the calculated characteristic parameters. Further, controller 14 classifies the particles based on the calculated characteristic parameters and counts the numbers of the particles included in the measurement specimen.

As illustrated in FIGS. 3A to 3E, controller 14 classifies the particles in the measurement specimen based on scattergrams having predetermined characteristic parameters as two axes.

In the following explanation, for convenience, regions of the particles are set on the scattergrams and the particles are classified. However, the scattergram sand the regions do not always need to be created as a figure or a graph. Extraction of the particles included in the regions may be performed by data processing for extracting, through filtering, only the particles belonging to a specific numerical value range.

In the scattergrams illustrated in FIGS. 3A to 3E, the vertical axis and the horizontal axis indicates any ones of FSCP, FSCW, SSCP, FLLP, FLLW, FLLA, FLHP, FLHW, and FLHA. The FSCP is a peak value of the intensity of the front scattered light, that is, the front scattered light signal. The FSCW is a pulse width of the front scattered light signal. The SSCP is a peak value of the intensity of the side scattered light, that is, the side scattered light signal. The FLLP is a peak value of the low-sensitivity fluorescent light signal. The FLLW is a pulse width of the low-sensitivity fluorescent light signal. The FLLA is a pulse area of the low-sensitivity fluorescent light signal. The FLHP is a peak value of the high-sensitivity fluorescent light signal. The FLHW is a pulse width of the high-sensitivity fluorescent light signal. The FLHA is a pulse area of the high-sensitivity fluorescent light signal.

In the scattergram illustrated in FIG. 3A, a red blood cell and a crystal are respectively included in regions 121 and 122. In the scattergram illustrated in FIG. 3B, a cast and a mucous thread are respectively included in regions 123 and 124. In the scattergram illustrated in FIG. 3C, a heterotypic cell, a white blood cell, and an epithelial cell are respectively included in regions 125 to 127. In the scattergram illustrated in FIG. 3D, a sperm, a fungus, and Trichomonas are respectively included in regions 128 to 130. In the scattergram illustrated in FIG. 3E, bacteria are included in region 131. Controller 14 counts the numbers of the particles included in the regions on the scattergrams and acquires values of the count as the numbers of particles by types corresponding to the regions.

Referring back to FIG. 1, controller 14 of testing apparatus 10 transmits the characteristic parameters calculated from optical information acquired from the particles of the measurement specimen, that is, the front scattered light signal, the side scattered light signal, and the fluorescent light signal and the numbers of the particles counted for each of the types based on the optical information to management apparatus 30. The optical information includes the characteristic parameters calculated from the front scattered light signals, the side scattered light signals, and the fluorescent light signals in the cases in which light receivers 104 to 106 are respectively set to low sensitivity and high sensitivity. Management apparatus 30 stores the received information in association with identification information of the urine sample.

Image capturing apparatus 20 includes sample supplier 21, image capturer 22, controller 23, and storage 24.

Sample supplier 21 includes suction unit 21a that sucks the urine sample. Suction unit 21a is formed from a pipe-like suction tube. Sample supplier 21 supplies the urine sample sucked by suction unit 21a to image capturer 22. Image capturer 22 captures images of the supplied urine sample and transmits the captured images to controller 23. Controller 23 includes an arithmetic processing circuit such as a CPU. Storage 24 includes memories such as a ROM, a RAM, and a hard disk. Storage 24 retains various kinds of information necessary for control by controller 23. Storage 24 is also used as a work region when controller 23 performs control.

Controller 23 controls the components of image capturing apparatus 20 according to a computer program stored in storage 24. Controller 23 causes storage 24 to store the captured images acquired from image capturer 22. Controller 23 segments cell images from the captured images and classifies the segmented cell images into eight classes based on the sizes of the cell images. Controller 23 causes storage 24 to store the cell images together with the classes. Controller 23 transmits the cell images to controller 33 of management apparatus 30 together with the classes. Note that controller 23 may subject the segmented cell images to image processing to thereby automatically classify kinds of particles included in the cell images and transmit the cell images to management apparatus 30 together with a result of the automatic classification.

Figure 4:
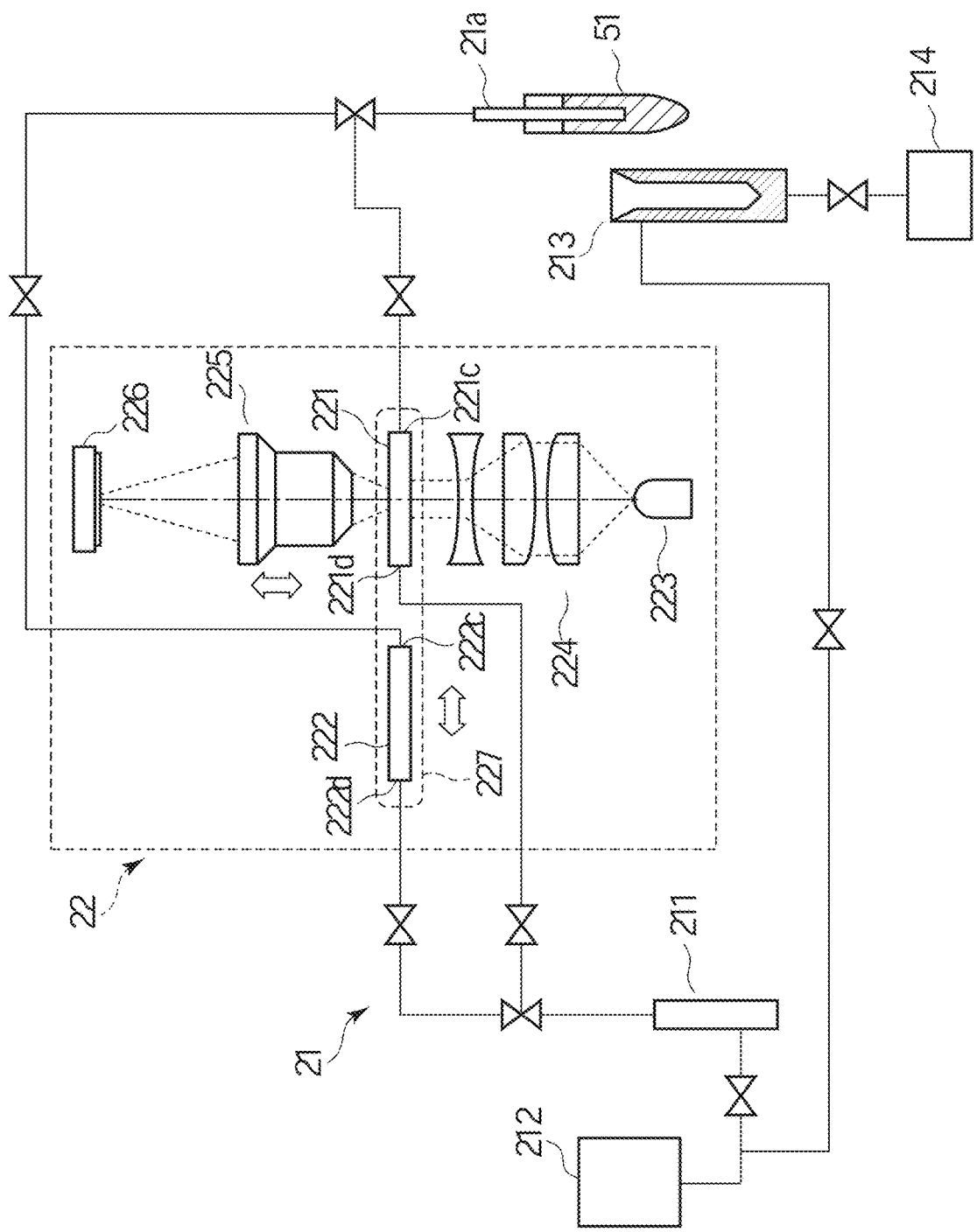
FIG. 4 is a diagram illustrating the configuration of an image capturer according to the first embodiment.

As illustrated in FIG. 4, image capturer 22 includes first cell 221, second cell 222, light source 223, irradiation optical system 224, objective lens 225, image capturing element 226, and stage 227.

First cell 221 and second cell 222 are respectively a cubic container made of a transparent material such as quartz glass. First cell 221 and second cell 222 are fixed to stage 227. Stage 227 feeds first cell 221 and second cell 222 in an arrangement direction of first cell 221 and second cell 222.

As illustrated in FIGS. 5A and 5B, first cell 221 and second cell 222 respectively include rectangular parallelepiped internal spaces 221a and 222a having small width in the thickness direction. Internal spaces 221a and 222a have the same shape and the same size. As illustrated in FIG. 5A, internal spaces 221a and 222a are disposed in the same position in the left-right direction. As illustrated in FIG. 5B, internal spaces 221a and 222a are disposed in the same position in the up-down direction.

First cell 221 includes inflow port 221b for causing the urine sample to flow into internal space 221a and outflow port 221c for causing the urine sample to flow out from internal space 221a. Second cell 222 includes inflow port 222b for causing the urine sample to flow into internal space 222a and outflow port 222c for causing the urine sample to flow out from internal space 222a. The bottom surface of internal space 221a of first cell 221 and the bottom surface of internal space 222a of second cell 222 are formed as a uniform plane having high surface accuracy.

Referring back to FIG. 4, light source 223 emits light having a predetermined wavelength. Light source 223 is, for example, a light emitting diode. Irradiation optical system 224 is configured by combining lenses. Irradiation optical system 224 converts the light from light source 223 into parallel light and applies the light to an image capturing region of objective lens 225. Objective lens 225 forms, on a light receiving surface of image capturing element 226, an image of the image capturing region to which the light is applied. Image capturing element 226 is, for example, a CCD image sensor or a CMOS image sensor. Objective lens 225 is driven in an optical axis direction for focus adjustment.

Inflow port 221b of first cell 221 is connected to suction unit 21a via a tube and two electromagnetic valves. Outflow port 221c of first cell 221 is connected to pump 211 via a tube and two electromagnetic valves. Inflow port 222b of second cell 222 is connected to suction unit 21a via a tube and two electromagnetic valves. Outflow port 222c of second cell 222 is connected to pump 211 via a tube and two electromagnetic valves.

Pump 211 is connected to, via a tube and an electromagnetic valve, container 212 that stores buffer liquid. The buffer liquid is filled in the tube in order to introduce the urine sample. Container 212 is connected to cleaning tank 213 via a tube and two electromagnetic valves. The buffer liquid is supplied to cleaning tank 213 and used as cleaning liquid as well. Waste liquid container 214 is provided below cleaning tank 213.

The urine sample stored in sample container 51 is introduced into either one of first cell 221 and second cell 222 by operating pump 211 in a state in which the electromagnetic valves are controlled to be opened and closed. Pump 211 operates until the urine sample flows out from outflow port 221c or outflow port 222c. Consequently, the urine sample is filled in internal space 221a of first cell 221 or internal space 222a of second cell 222.

When the image capturing for the urine sample filled in first cell 221 or second cell 222 ends, cleaning of suction unit 21a and first cell 221 or second cell 222 is performed. For the cleaning, suction unit 21a is moved to cleaning tank 213. When pump 211 operates, the buffer liquid is supplied to internal space 221a of first cell 221 or internal space 222a of second cell 222. Internal space 221a or internal space 222a is cleaned. The urine sample pushed out from internal space 221a of first cell 221 or internal space 222a of second cell 222 by the inflow of the buffer liquid is discharged to cleaning tank 213 from suction unit 21a. When pump 211 further operates, the buffer liquid is discharged from suction unit 21a. The inside of suction unit 21a is cleaned. The buffer liquid is supplied to cleaning tank 213 from container 212. The outer side of suction unit 21a is cleaned. Waste liquid discharged from cleaning tank 213 is stored in waste liquid container 214.

As illustrated in FIGS. 6A and 6B, during the image capturing, first cell 221 and second cell 222 are fed in the right direction by stage 227. While first cell 221 and second cell 222 are fed in the right direction, objective lens 225 is moved in an optical axis direction by driving mechanism 228 and focus adjustment is performed. While first cell 221 is fed, image capturing element 226 captures images of the urine sample filled in first cell 221 at a fixed interval. In this way, a predetermined number of images are captured for first cell 221. For example, forty images are captured for first cell 221.

After the image capturing for first cell 221 ends, further, first cell 221 and second cell 222 are fed in the right direction. When the image capturing region of objective lens 225 reaches a start position of second cell 222, image capturing for second cell 222 is started. As explained above, a predetermined number of images are captured for second cell 222. The number of captured images for second cell 222 is the same as the number of captured images for first cell 221.

As illustrated in FIG. 7A, during the image capturing, first cell 221 is fed in the right direction. At this point, first cell 221 is fed by stage 227 in a direction tilting at a fixed angle from the horizontal direction while the bottom surface of internal space 221a keeps the horizontal state. On the bottom surface of first cell 221, reference marks 221d and 221e of predetermined patterns are formed in an image capturing start position and an image capturing end position. Reference marks 221d and 221e are formed by fine grooves formed by laser machining. As explained below, a focus position of objective lens 225 during an image capturing operation is determined using reference marks 221d and 221e.

First, prior to the start of the image capturing operation, the buffer liquid is filled in first cell 221. Subsequently, as illustrated in FIG. 7A, objective lens 225 is focused such that an image of reference mark 221d is formed on image capturing element 226. Position 229a of objective lens 225 where the image of reference mark 221d is formed on image capturing element 226 is acquired as a focus position. Thereafter, first cell 221 is fed in the direction tilting at the fixed angle from the horizontal position as explained above. First cell 221 is located in a position illustrated in FIG. 7B. In this position, objective lens 225 is focused such that an image of reference mark 221e is formed on image capturing element 226. Position 229b of objective lens 225 where the image of reference mark 221e is formed on image capturing element 226 is acquired as a second focus position. A tilt of a linear function of a focus position with respect to a feeding direction is calculated based on a difference between the first focus position and the second focus position and the distance between reference marks 221d and 221e in the feeding direction of first cell 221. A tilt of a linear function is calculated for second cell 222 in the same manner.

During the image capturing for first cell 221 and second cell 222, the focus positions of objective lens 225 in the feeding positions of first cell 221 and second cell 222 are set using the linear functions, the tiles of which are calculated as explained above. The buffer liquid is selected such that a refractive index of the buffer liquid and a refractive index of the urine sample are approximate to each other. Therefore, when the position of objective lens 225 is set according to the linear functions, the tilts of which are calculated as explained above, the focus of objective lens 225 is located near the bottom surfaces of first cell 221 and second cell 222 in the feeding positions of first cell 221 and second cell 222. Consequently, it is possible to properly capture images of particles sunk on the bottoms of first cell 221 and second cell 222. The image capturing for first cell 221 and second cell 222 is performed while the position of objective lens 225 is adjusted in this way.

As illustrated in FIG. 8, as a cycle of the image capturing operation for first cell 221 and second cell 222, four processes of suction, still standing, image capturing, and cleaning are one cycle. The suction process is a process for filing the urine sample in first cell 221 or second cell 222. The standing still process is a process for sinking the particles in the urine sample filled in first cell 221 or second cell 222 to the bottom surface of first cell 221 or second cell 222. The image capturing process is a process for capturing images of the urine sample filled in first cell 221 or second cell 222. The cleaning process is a process for cleaning internal space 221a of first cell 221 or internal space 222a of second cell 222.

In a period of the still standing process of first cell 221, the processes of image capturing, cleaning, and suction for second cell 222 are performed. In a period of the still standing process of second cell 222, the processes of image capturing, cleaning, and suction for first cell 221 are performed. Consequently, the image capturing, the cleaning, and the suction for the cells can be smoothly performed. During the image capturing operation, the processes of one cycle illustrated in FIG. 8 are repeatedly performed for first cell 221 and second cell 222.

Referring back to FIG. 1, management apparatus 30 includes input unit 31, display unit 32, controller 33, and storage 34. Management apparatus 30 is configured from, for example, a personal computer. Input unit 31 includes a keyboard and a mouse. Display unit 32 is a monitor. Controller 33 is configured from an arithmetic processing circuit such as a CPU and executes control conforming to a control program stored in storage 34. Storage 34 includes memories such as a ROM, a RAM, and a hard disk.

Conveyance apparatus 40 includes two conveyance units 41 and 42, collection unit 43, and controller 44. Conveyance units 41 and 42 are respectively disposed on the front sides of testing apparatus 10 and image capturing apparatus 20. Conveyance units 41 and 42 have the same configuration.

Conveyance unit 41 includes first conveyance path 411 for measuring sample container 51 held in sample rack 50 and second conveyance path 412 for conveying sample rack 50 to the downstream side. First conveyance path 411 and second conveyance path 412 are lower than the upper surface of conveyance unit 41 by one stage. First conveyance path 411 includes right tank 411a, left tank 411b, and linear section 411c that connects right tank 411a and left tank 411b. Second conveyance path 412 is a linear conveyance path. Second conveyance path 412 includes a belt conveyor that feeds sample rack 50 downward.

When sample rack 50 is conveyed on first conveyance path 411, a not-illustrated push-out mechanism pushes the front surface of sample rack 50 and pushes out sample rack 50 from second conveyance path 412 to right tank 411a of first conveyance path 411. A not-illustrated feeding mechanism feeds sample rack 50 to linear section 411c. The feeding mechanism causes right tank 411a to project protrusions from the left and the right and move the protrusions in the direction of linear section 411c. At this point, the protrusions come into contact with the front surface of sample rack 50 and feed sample rack 50 to linear section 411c.

Linear section 411c includes a belt conveyor. Sample rack 50 is fed in the left direction by the belt conveyor. Suction unit 11a sucks the urine sample from the predetermined sample container 51 held by sample rack 50. When the suction operation for sample rack 50 ends, the belt conveyor of linear section 411c feeds sample rack 50 to the left end of linear section 411c. The not-illustrated push-out mechanism pushes the rear surface of sample rack 50 and pushes sample rack 50 into left tank 411b. The not-illustrated feeding mechanism pushes the rear surface of sample rack 50 in the direction of second conveyance path 412 oppositely to the case of right tank 411a and feeds sample rack 50 to second conveyance path 412. The belt conveyor of second conveyance path 412 conveys sample rack 50 downstream.

Like conveyance unit 41, conveyance unit 42 includes first conveyance path 421 and second conveyance path 422. First conveyance path 421 includes right tank 421a, left tank 421b, and linear section 421c that connects right tank 421a and left tank 421b. Second conveyance path 422 is a linear conveyance path. As illustrated in FIG. 1, second conveyance path 422 of conveyance unit 42 is connected to second conveyance path 412 of conveyance unit 41. Consequently, sample rack 50 is passed from conveyance unit 41 to conveyance unit 42.

Collection unit 43 houses sample rack 50 for which measurement and image capturing ends. Controller 44 includes an arithmetic processing circuit such as a CPU and controls conveyance units 41 and 42 and collection unit 43 according to a control program.

When images of the urine sample in any one of sample containers 51 held by sample rack 50 is captured by image capturing apparatus 20, controller 44 of conveyance apparatus 40 performs, on conveyance unit 42 on the front side of image capturing apparatus 20, control for conveying, with first conveyance path 421, sample container 51, which stores an image capturing target urine sample, to a suction position of suction unit 21a. When it is unnecessary to capture, with image capturing apparatus 20, an image of urine samples in all of sample containers 51 held by sample rack 50, controller 44 of conveyance apparatus 40 performs, on conveyance unit 42 on the front side of image capturing apparatus 20, control for conveying, with the second conveyance path 422, sample rack 50 to collection unit 43.

In conveyance unit 41, controller 14 of testing apparatus 10 may perform the control of right tank 411a and linear section 411c in first conveyance path 421. Similarly, in conveyance unit 42, controller 23 of image capturing apparatus 20 may perform the control of right tank 421a and linear section 421c in first conveyance path 421.

Figure 9:
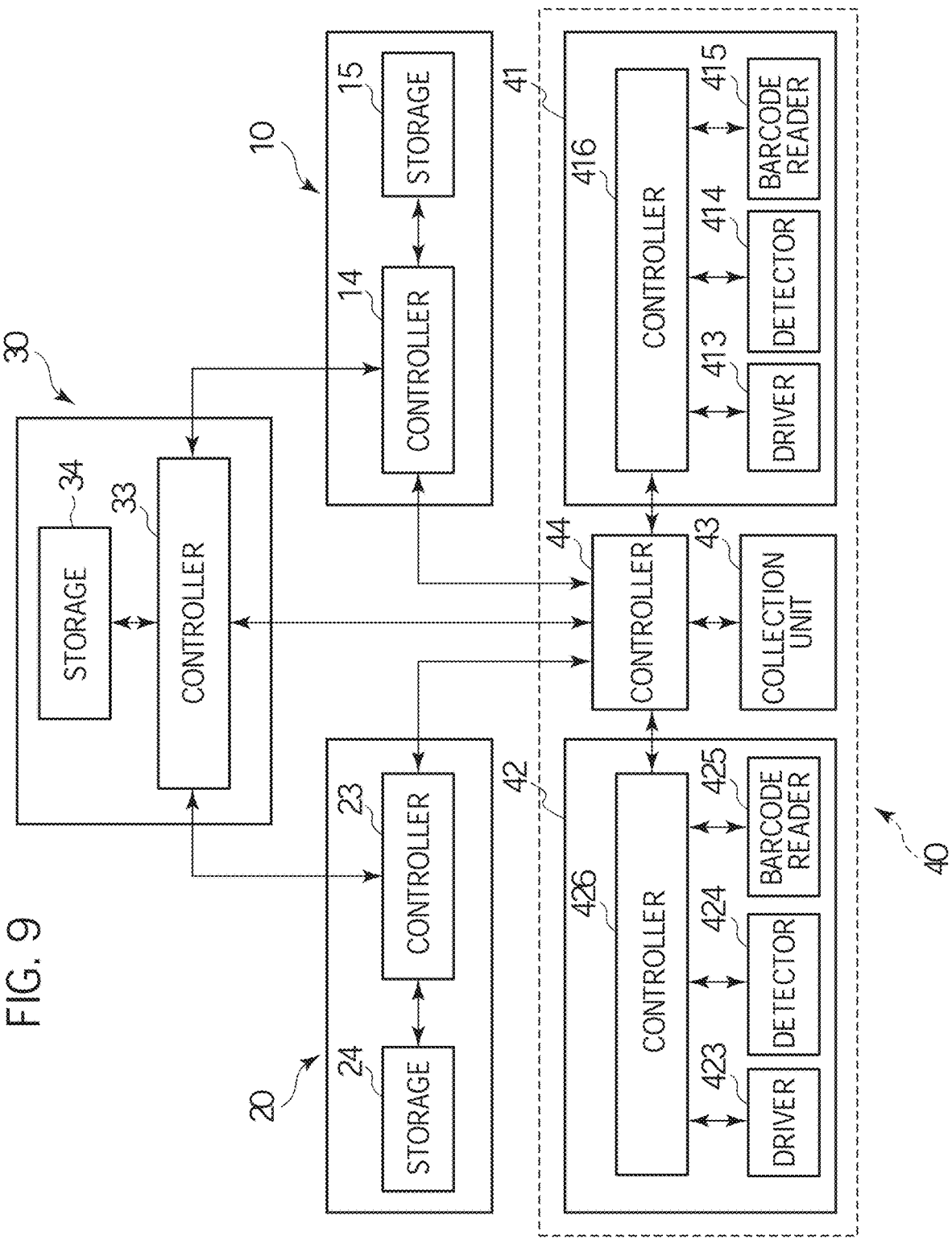
FIG. 9 is a diagram illustrating the configuration of a control system of the urine analysis system according to the first embodiment.

As illustrated in FIG. 9, conveyance unit 41 on the front side of testing apparatus 10 includes driver 413, detector 414, barcode reader 415, and controller 416. Driver 413 includes a belt conveyor, a feeding mechanism, and a push-out mechanism for conveying sample rack 50 with first conveyance path 411 and second conveyance path 412 illustrated in FIG. 1. Detector 414 includes a sensor that detects sample rack 50 and sample container 51 in predetermined positions on first conveyance path 411 and second conveyance path 412.

Barcode reader 415 reads a barcode of sample rack 50 and a barcode of sample container 51 held by sample rack 50. The reading of the barcodes is performed in a predetermined position between the right end of linear section 411c of first conveyance path 411 and a suction position of suction unit 11a. Controller 416 includes an arithmetic processing circuit such as a CPU and executes control conforming to a control program. Controller 416 includes a memory for storing an image capturing order and the like explained below.

Like conveyance unit 41, conveyance unit 42 on the front side of image capturing apparatus 20 includes driver 423, detector 424, barcode reader 425, and controller 426. Reading of the barcodes of sample rack 50 and sample container 51 is performed in a position between the right end of linear section 421c of first conveyance path 421 and the suction position of suction unit 21a.

Measurement of the urine sample is started when sample rack 50 is placed in right tank 411a of conveyance unit 41 on the front side of testing apparatus 10. Controller 416 causes driver 413 to convey sample rack 50 from right tank 411a to linear section 411c and further convey sample rack 50 to a reading position of barcode reader 415. Controller 416 causes barcode reader 415 to read the barcode of sample rack 50 and the barcode of sample container 51. Consequently, controller 416 acquires identification information of sample rack 50 and identification information of sample container 51.

Controller 416 transmits the acquired identification information to controller 44. Controller 44 transmits, together with the received identification information, a transmission request for a measurement order of the urine sample in sample container 51 held by sample rack 50 to management apparatus 30. Controller 33 of management apparatus 30 extracts a measurement order from storage 34 based on the received identification information. The user registers measurement orders of the urine samples in management apparatus 30 in advance. Controller 33 transmits the extracted measurement order to controller 44 of conveyance apparatus 40. At this point, controller 33 transmits the extracted measurement order to controller 14 of testing apparatus 10 as well.

Controller 44 of conveyance apparatus 40 transmits a conveyance command to controller 41 according to the received measurement order. Controller 416 conveys, according to the received conveyance order, sample containers 51 of sample rack 50 to the suction position of suction unit 11a of testing apparatus 10 in order. Every time the conveyance of sample containers 51 to the suction position is completed, controller 416 notifies the conveyance completion to controller 14 of testing apparatus 10 via controller 44. The notification includes the identification information of sample container 51 conveyed to the suction position. In response to the notification, controller 14 refers to the measurement order for sample container 51 present in the suction position and executes processing conforming to the measurement order.

When measurement for the urine sample in sample container 51 is necessary according to the measurement order, controller 14 causes suction unit 11a to suck the urine sample and performs measurement processing. When the measurement for the urine sample in sample container 51 is unnecessary according to the measurement order, controller 14 skips the suction of the urine sample. When the suction processing for sample container 51 conveyed to the suction position ends, controller 14 notifies suction processing completion to controller 416 via controller 44 of conveyance apparatus 40. When the suction for sample container 51 is skipped, controller 14 also performs the notification of the suction processing completion. In response to the notification of the suction processing completion, controller 416 conveys the next sample container 51 to the suction position of suction unit 11a. In this way, controller 416 of conveyance unit 41 conveys all of sample containers 51 held by sample rack 50 to the suction position of suction unit 11a of testing apparatus 10 in order.

In the measurement in testing apparatus 10, a predetermined amount, e.g., approximately 8 μL of the urine sample is sucked from sample container 51 and a measurement specimen is prepared. The prepared measurement sample is fed to flow cell 101 and measurement is performed. That is, a measurement amount of the urine samples in testing apparatus 10 is, for example, approximately 8 μL. On the other hand, volumes of the urine sample that can be filled in first cell 221 and second cell 222 of image capturing apparatus 20 are respectively, for example, 1 μL. In testing apparatus 10, since an amount of the urine sample considerably larger than the amount of the urine in image capturing apparatus 20 is measured. Therefore, a highly accurate measurement result is obtained even when an amount of particles included in the urine sample is small.

Controller 14 of testing apparatus 10 transmits a measurement result for the urine samples in the urine containers 51 held by sample rack 50 to controller 33 of management apparatus 30 together with identification information of the urine sample. The measurement result includes the optical information acquired from the particles included in the urine sample, that is, the characteristic parameters calculated from the front scattering light signal, the side scattering light signal, and the fluorescent light signal and the number of particles counted for each of types. Consequently, controller 33 of management apparatus 30 determines necessity of image capturing for the urine sample, the measurement result of which is received.

Figure 10:
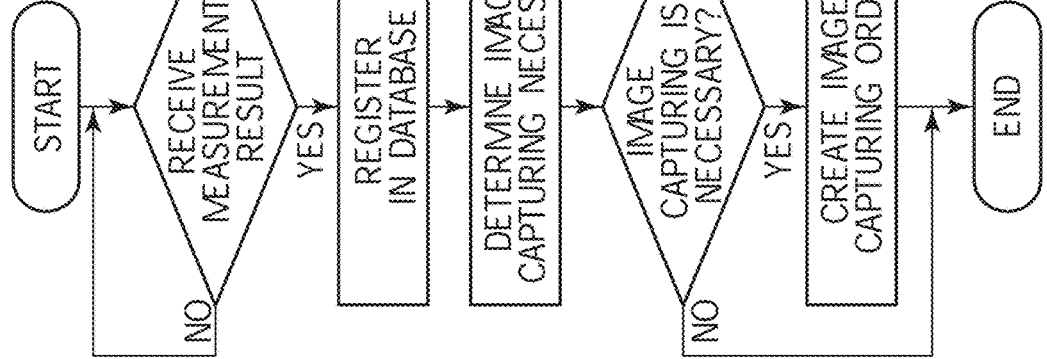
FIG. 10A is a flowchart for explaining image capturing order generation processing of a management apparatus according to the first embodiment.
FIGS. 10B and 10C are respective diagrams illustrating the configurations of first and second condition tables referred to in necessity determination for generation of an image capturing order according to the first embodiment.

As illustrated in FIG. 10A, in S101, controller 33 of management apparatus 30 determines whether a measurement result and identification information of a urine sample are received from testing apparatus 10. When the determination in S101 is YES, in S102, controller 33 causes storage 34 to store the received measurement result in association with the identification information of the urine sample. In storage 34, a database for storing the measurement result is constructed. Controller 33 registers the measurement result and the identification information received from testing apparatus 10 in the database. In S103, controller 33 determines necessity of image capturing by image capturing apparatus 20 based on the received measurement result. In the determination, controller 33 refers to a first condition table and a second condition table illustrated in FIGS. 10B and 10C.

In management apparatus 30, the user is capable of setting whether image capturing by image capturing apparatus 20 is performed in only a normal mode or in the normal mode and a close inspection mode. When the setting for performing the image capturing only in the normal mode is performed, controller 33 of management apparatus 30 refers to the first condition table illustrated in FIG. 10B and performs the determination in S103. When the setting for performing the image capturing in the normal mode and the close inspection mode is performed, controller 33 of management apparatus 30 refers to the second condition table illustrated in FIG. 10C and performs the determination in S103.

The normal mode is a mode for filling a urine sample sucked from one sample container 51 in only either one of first cell 221 and second cell 222 illustrated in FIG. 4 and performing image capturing. In this case, the number of captured images for the urine sample is a predetermined number, for example, forty. In the normal mode, images of particles are analyzed with respect to the number of images. The close inspection mode is a mode for filling the urine sample sucked from one sample container 51 in both of first cell 221 and second cell 222 illustrated in FIG. 4 and performing image capturing. In this case, the number of captured images for the urine sample is twice as many as the number of captured images in the normal mode, for example, eighty. In the close inspection mode, the images of particles are analyzed with respect to images twice as many as the number of images in the normal mode.

As illustrated in FIG. 10B, in the first condition table, a threshold for performing image capturing is set for each of particles. When the first condition table is used, controller 33 of management apparatus 30 compares count values of the particles included in the measurement result of testing apparatus 10 and thresholds of the particles of the first condition table. When the count value of at least one particle exceeds the threshold of the first condition table, controller 33 determines that image capturing by image capturing apparatus 20 is necessary for the urine sample. When the count values of all of the particles do not exceed the thresholds of the first condition table, controller 33 determines that the image capturing by image capturing apparatus 20 for the urine sample is unnecessary.

As illustrated in FIG. 10C, in the second condition table, a threshold for performing image capturing is set for each of the particles. Further, in the second condition table, conditions for performing the close inspection mode are set for predetermined particles. When the second condition table is used, first, controller 33 of management apparatus 30 compares the count values of the particles included in the measurement result of testing apparatus 10 and thresholds of the particles of the second condition table. When the count value of at least one particle exceeds the threshold of the second condition table, controller 33 determines that the image capturing by image capturing apparatus 20 is necessary for the urine sample. When the count values of all of the particles do not exceed the thresholds of the second condition table, controller 33 determines that the image capturing by image capturing apparatus 20 for the urine sample is unnecessary.

When determining according to the thresholds that the image capturing is necessary, controller 33 further refers to the conditions of the close inspection mode and determines necessity of the close inspection mode. In the case of FIG. 10C, when a count value of at least one of an epithelial cell and a cast exceeds a threshold for the image capturing necessity determination, controller 33 determines that the image capturing by the close inspection mode is necessary. Even if count values of both of the epithelial cell and the cast do not exceed thresholds for the image capturing necessity determination, when a count value of a red blood cell is equal to or larger than 60 µL, which is a condition of the close inspection mode, controller 33 determines that the image capturing by the close inspection mode is necessary. When both of the conditions of the close inspection mode are satisfied, controller 33 determines that the image capturing by the close inspection mode is unnecessary and selects the image capturing by the normal mode.

The user may be capable of optionally setting the threshold of the first condition table, the threshold of the second condition table, and the conditions of the close inspection mode.

In S104, controller 33 determines whether a determination result that the image capturing by image capturing apparatus 20 is necessary is obtained for the urine sample for which the measurement result is received. When the determination in S104 is YES, in S105, controller 33 generates an image capturing order for the urine sample and causes storage 34 to store the generated image capturing order in association with identification information of the urine sample. The image capturing order includes information on in which of the normal mode and the close inspection mode image capturing and analysis for the urine sample are executed. When the determination in S104 is NO, controller 33 ends the processing without generating an image capturing order for the urine sample.

Figure 11:
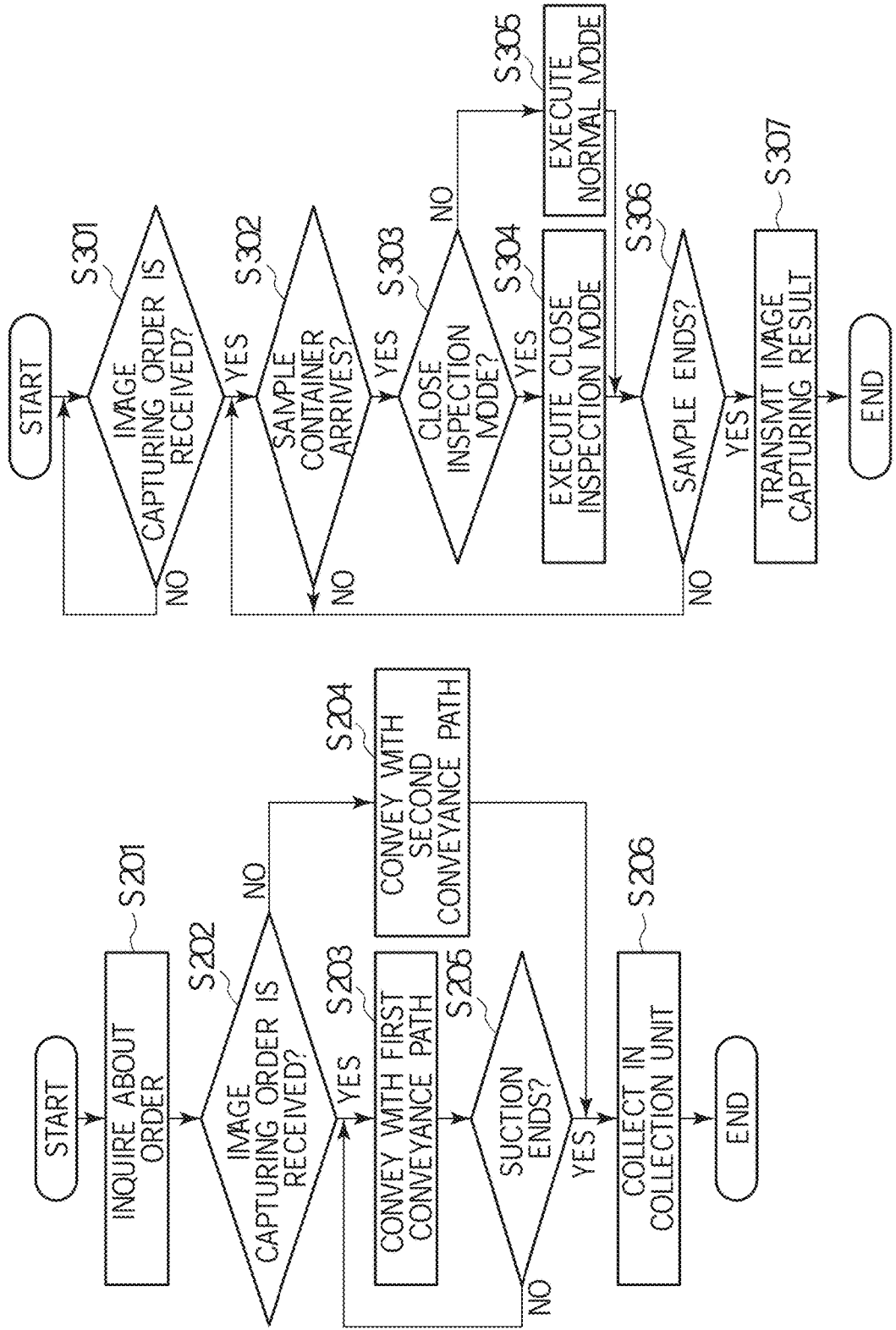
FIG. 11A is a flowchart for explaining conveyance control of a conveyance apparatus according to the first embodiment.
FIG. 11B is a flowchart for explaining image capturing processing of an image capturing apparatus according to the first embodiment.

As illustrated in FIG. 11A, when the sample track 50 is delivered from conveyance unit 41 on the front side of testing apparatus 10 to conveyance unit 42 on the front side of image capturing apparatus 20, in S201, controller 44 of conveyance apparatus 40 transmits a transmission request for an image capturing order to management apparatus 30 together with the identification information of sample containers 51 held by the conveyance target sample rack 50. Controller 33 of management apparatus 30 extracts image capturing orders for urine samples from storage 34 based on the received identification information. When an image capturing order is extracted concerning any one of the urine samples, controller 33 transmits the extracted image capturing order and identification information associated with the image capturing order to controller 44 of conveyance apparatus 40 and controller 23 of image capturing apparatus 20. When an image capturing order is not extracted concerning all of the urine samples, controller 33 transmits a notification indicating to that effect to controller 44 of conveyance apparatus 40.

In S202, controller 44 of conveyance apparatus 40 determines whether an image capturing order is received concerning the urine sample in sample container 51 held by the conveyance target sample rack 50. When the determination in S202 is YES, in S203, controller 44 transmits, to controller 426 of conveyance unit 42 disposed on the front side of image capturing apparatus 20, a conveyance command for conveying, with first conveyance path 421, an image capturing target urine sample to the suction position of suction unit 21a. Controller 426 conveys sample container 51, which stores the image capturing target sample, to the suction position of suction unit 21a.

When the conveyance of sample container 51 to the suction position is completed, controller 426 transmits a conveyance completion notification to controller 23 of image capturing apparatus 20 via controller 44. The conveyance completion notification includes the identification information of sample container 51 conveyed to the suction position. In response to the notification, suction of the urine sample from sample container 51 is performed in image capturing apparatus 20. When the suction is completed, controller 23 of image capturing apparatus 20 transmits a notification to that effect to controller 426 of conveyance unit 42 via controller 44 of conveyance apparatus 40.

In S205, controller 426 determines whether the suction in image capturing apparatus 20 ends for all of image capturing target urine samples stored in the conveyance target sample rack 50. Controller 426 conveys the image capturing target urine samples to the suction position in order until the suction ends for all of the image capturing target urine samples. When the determination in S205 is YES, in S206, controller 426 conveys the conveyance target sample rack 50 to collection unit 43. Consequently, controllers 44 and 426 end the processing for the conveyance target sample rack 50.

When the determination in S202 is NO, in S204, controller 44 transmits, to controller 426 of conveyance unit 42, a conveyance command for conveying, with second conveyance path 422, the conveyance target sample rack 50 to collection unit 43. In S206, controller 426 conveys the conveyance target sample rack 50 to collection unit 43 based on the received conveyance command. Consequently, controllers 44 and 426 end the processing for the conveyance target sample rack 50.

As illustrated in FIG. 11B, in S301, controller 23 of image capturing apparatus 20 determines whether an image capturing order is received. As explained above, in S201 in FIG. 11A, the image capturing order is transmitted to controller 23 of image capturing apparatus 20. That is, in response to the transmission request for an image capturing order from controller 44 of conveyance apparatus 40, controller 33 of management apparatus 30 extracts an image capturing order for sample container 51 held by the conveyance target sample rack 50. Controller 33 of management apparatus 30 transmits the extracted image capturing order to controller 44 of conveyance apparatus 40 and transmits the extracted image capturing order to controller 23 of image capturing apparatus 20 as well. In this way, when controller 23 of image capturing apparatus 20 receives the image capturing order, the determination in S301 is YES. Controller 23 of image capturing apparatus 20 causes storage 24 to store the received image capturing order.

In S302, controller 23 determines whether sample container 51, which stores the image capturing target urine sample, has reached the suction position of suction unit 21a. The determination in S302 is YES when, in S203 in FIG. 11A, controller 44 of conveyance apparatus 40 transmits the conveyance completion notification of sample container 51 to controller 23 of image capturing apparatus 20 and controller 23 of image capturing apparatus 20 receives the conveyance completion notification. As explained above, the conveyance completion notification includes the identification number of sample container 51 conveyed to the suction position.

When determining YES in S302, controller 23 of image capturing apparatus 20 refers to an image capturing order corresponding to the identification information included in the conveyance completion notification among the image capturing orders stored in storage 24. In S303, controller 23 determines whether the image capturing order referred to includes mode information in the close inspection mode. When the image capturing order referred to includes mode information of the close inspection mode, the determination in S303 is YES. When the image capturing order referred to includes mode information of the normal mode, the determination in S303 is NO.

When the determination in S303 is YES, in S304, controller 23 executes image capturing and analysis in the close inspection mode. When the determination in S303 is NO, in S305, controller 23 executes image capturing and analysis in the normal mode. Controller 23 executes the processing in S302 to S305 until it is determined in S306 that the processing for all of the image capturing target urine samples stored in sample rack 50 ends. When the determination in S306 is YES, in S307, controller 23 transmits cell images of the particles obtained by the analysis and an image capturing result including classes of the cell images and the identification information of the urine sample to management apparatus 30 and ends the processing. Controller 33 of management apparatus 30 registers the received image capturing result in association with identification information corresponding to the database constructed in storage 34.

When the mode of image capturing apparatus 20 is set to the mode for executing only the normal mode, S303 and S304 are omitted and S305 is executed on all of the image capturing target urine samples.

In S304 and S305, controller 23 segments cell images from a captured image. Controller 23 classifies the cell images into eight classes based on the sizes of the segmented cell images. In the normal mode, for example, the segmentation and the classification of cell images are performed on forty captured images. In the close inspection mode, the segmentation and the classification of cell images are performed on, for example, eighty captured images twice as many as the captured images in the normal mode. In the close inspection mode, analysis processing takes time compared with the normal mode. However, more cell images can be segmented and acquired.

Management apparatus 30 is configured to display, for each of the urine samples, on display unit 32, a screen simultaneously including the measurement result of testing apparatus 10 and the image capturing result of image capturing apparatus 20 registered in the database in this way.

Figure 12:
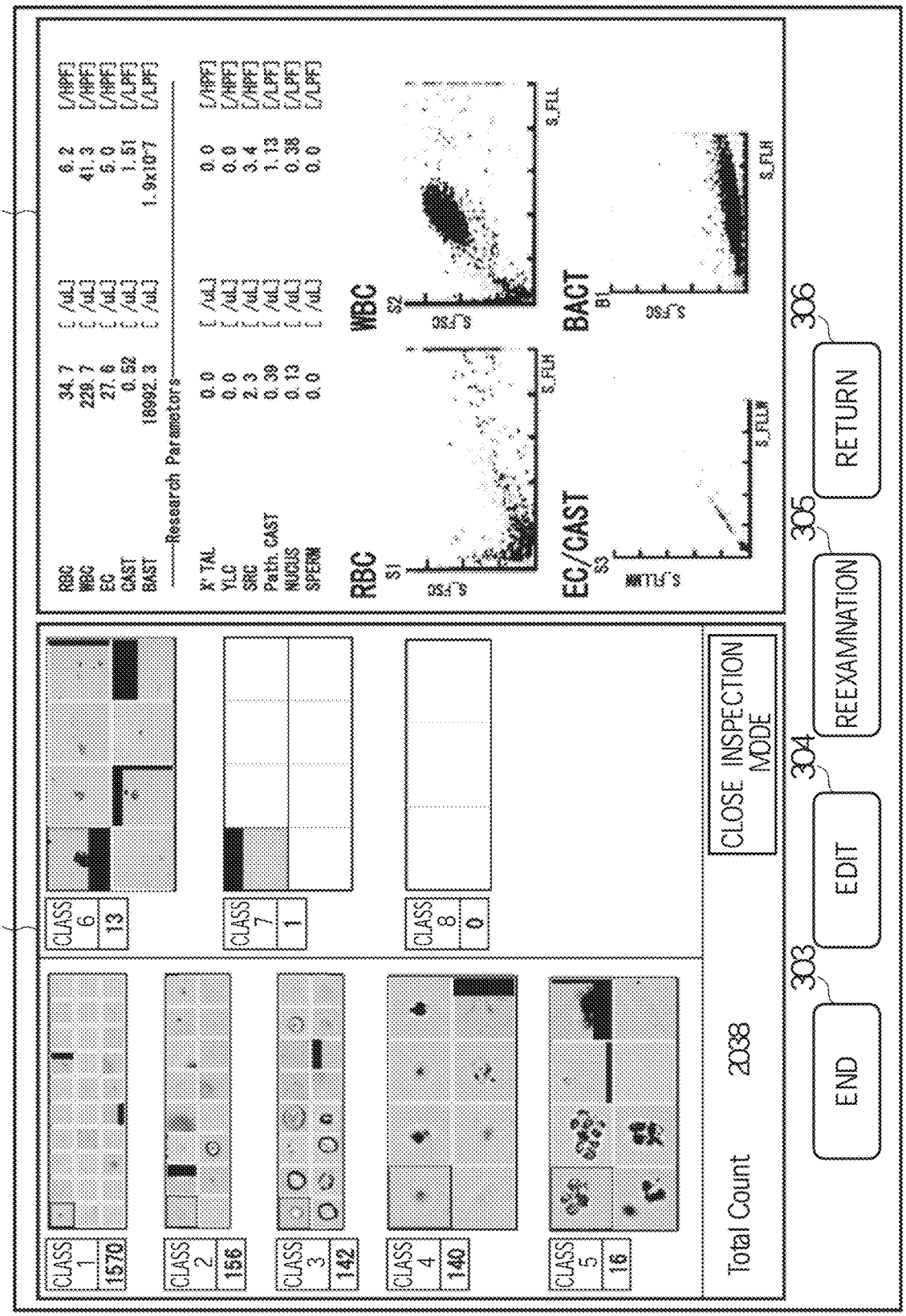
FIG. 12 is a diagram illustrating the configuration of a browsing screen of the management apparatus according to the first embodiment.

For example, a browsing screen illustrated in FIG. 12 is displayed on display unit 32. The browsing screen includes region 301 where the measurement result of testing apparatus 10 is displayed, region 302 where the image capturing result of image capturing apparatus 20 is displayed, and operation buttons 303 to 306. In region 301, counting results of the particles are displayed in an upper part as counting values per unit volume. In a lower part of region 301, scattergrams for the particles are displayed. In the scattergrams, colors of plots are changed for each of the particles.

In region 302, the cell images are classified and displayed in an upper part. In lower parts of labels of the classes, the numbers of cells included in the classes are added. In a lower part of region 302, a total number of extracted cell images and indication indicating in which of the close inspection mode and the normal mode the image capturing and the analysis are performed. In the example illustrated in FIG. 12, it is indicated that the image capturing and the analysis are executed in the close inspection mode. When the user clicks the labels of the classes via input unit 31, the browsing screen is switched to a screen on which all of the cell images included in the classes are displayed. A scroll bar is added to the screen as appropriate.

The cell images are classified into the classes according to the sizes of the cell images and displayed. For example, in class 1, a cell image having a size equivalent to bacteria is displayed. In class 2, a cell image having a size equivalent to a red blood cell, a crystal, and a fungus is displayed. In class 3, a cell image having a size equivalent to a white blood cell, a crystal, and a fungus is displayed. In class 4, a cell image having a size equivalent to a small circular epithelial cell is displayed. In class 5, a cell image having a size equivalent to a flat epithelial cell is displayed. In class 6, a cell image having a size equivalent to a cast and a flat epithelial cell is displayed. In class 7, a cell image having a size equivalent to a cast and an epithelial cell is displayed. In class 8, a cell image having a size equivalent to a cast and an epithelial cell larger than the size of the class 7 is displayed. Therefore, the user is capable of estimating types of the particles illustrated in the cell images referring to the classes.

On an immediately preceding screen of the browsing screen illustrated in FIG. 12, a list of measurement results and image capturing results registered in the database is displayed in association with identification numbers of the urine samples. In the list, a test date and time, a name, sex, and age of a subject, and a type and a name of a facility that samples the urine samples are described. The type of the facility is a subject of medical treatment of a facility that uses a measurement result of urine such as a urology department and a pediatric department. When a predetermined identification number in the displayed list is selected via input unit 31, the browsing screen illustrated in FIG. 12 is displayed. When returning to the list, the user presses button 306 via input unit 31.

On the screen illustrated in FIG. 12, a laboratory technician or the like is capable of performing editing work for classifying the cell images included in the classes for each of the particles. The user can perform editing by pressing button 304 via input unit 31. For example, when the user presses button 304 after selecting a class via input unit 31, a screen including all of the cell images included in the selected class and storage boxes of the particles is displayed. The user performs classification of the cell images by dragging the displayed cell images to the storage boxes of the particles corresponding to the displayed cell images. The user drags the cell images, which are not the classification target particles, to a storage box unrelated to the classification target. When the editing work ends, the user presses button 303 via input unit 31. Consequently, the classification of the cell images is decided. Information after the classification is stored in the database. According to the information after the classification, for example, a browsing screen illustrated in FIG. 13 is displayed.

Figure 13:
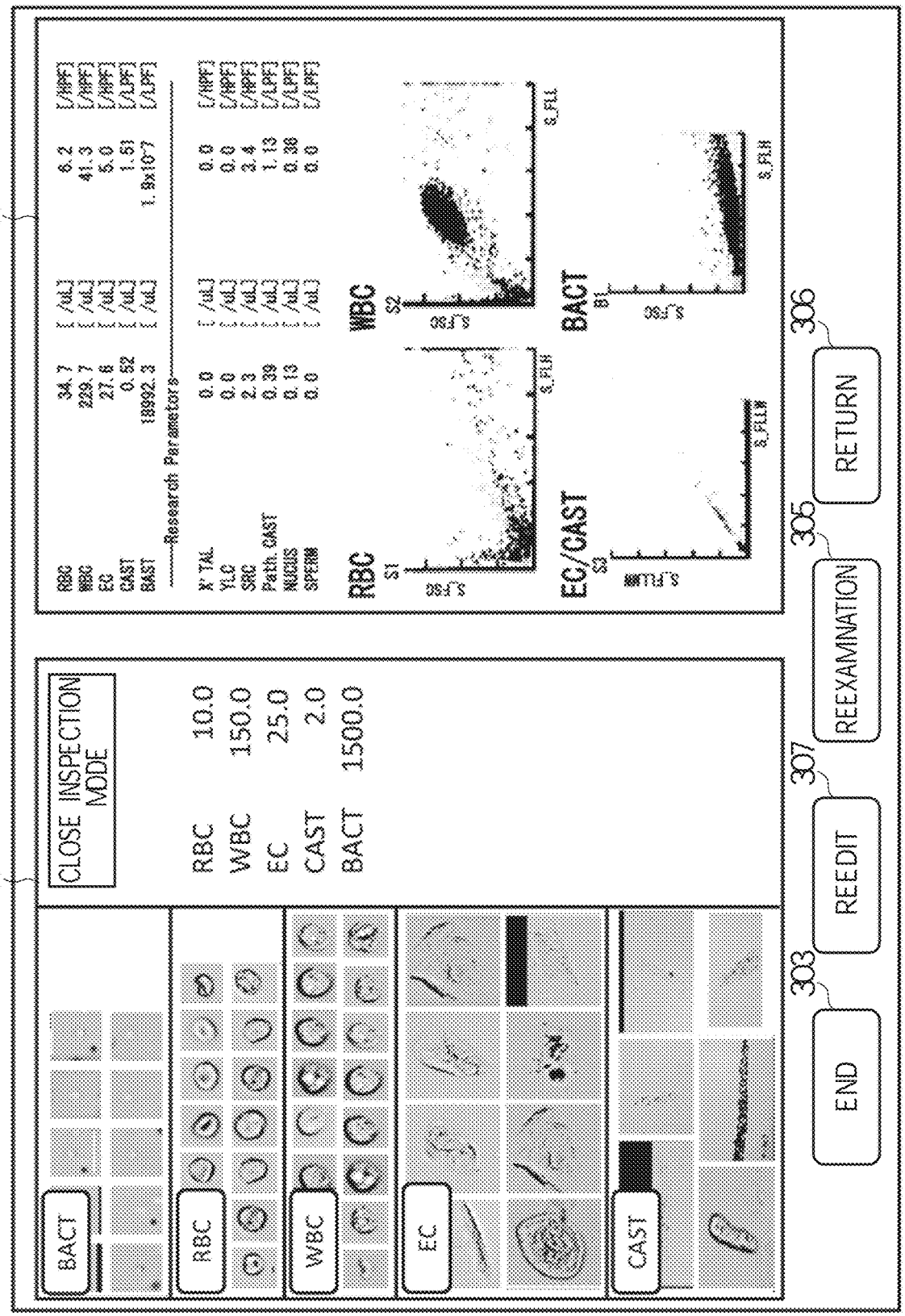
FIG. 13 is a diagram illustrating the configuration of the browsing screen of the management apparatus according to the first embodiment.

In the browsing screen illustrated in FIG. 13, region 301 is the same as region 301 in the browsing screen illustrated in FIG. 12. In the screen illustrated in FIG. 13, region 302 illustrated in FIG. 12 is changed to a region 308. In the region 308, the cell images are classified for each of the particles in a left side portion. The numbers of the cell images of the particles are displayed in a right side portion. The user can perform reclassification of the cell images by pressing button 307 via input unit 31 as appropriate. Buttons 303, 305, and 306 are the same as the buttons illustrated in FIG. 12.

During browsing of the screen illustrated in FIG. 12 or FIG. 13, when the user finds abnormality in the urine sample and determines that reexamination for the subject is necessary, the user presses button 305 via input unit 31. When salt separates out in the urine sample and classification of the cell images cannot be performed or when a large number of mucous threads are present in the urine sample and the cell images cannot be classified, the user also presses button 305 via input unit 31. Consequently, information indicating that reexamination is necessary for the identification information of the urine sample being browsed is necessary is added on the database. Reexamination by microscopic observation or the like is performed on the subject having the identification information to which the information is added. When the information indicating that the reexamination is necessary is added to the database, the user can easily confirm necessity of the reexamination as appropriate.

By referring to the screen illustrated in FIG. 12 or FIG. 13, the user can simply and accurately determine, by referring to the cell images, a condition of a disease that is not easily accurately diagnosed from the measurement result of testing apparatus 10.

For example, in the measurement performed using detector 12, mucous threads and aggregates such as bacteria and salts having shapes extremely similar to casts sometimes cannot be distinguished. Crystal components and yeast-like funguses having shapes similar to red blood cells sometimes cannot be classified. Further, in the method of performing measurement using detector 12, atypical cells in urine sometimes cannot be distinguished from other urine particles and accurately detected. When it is suspected from the measurement result displayed in region 301 that particles affecting diagnosis such as casts and atypical cells are included in the urine sample, by referring to the screen illustrated in FIG. 12 or FIG. 13, the user can refer to the cell images in region 302 and confirm whether the particles are included in the urine sample. Therefore, according to this embodiment, it is possible to highly accurately proceed with diagnosis of urine without being requested to perform complicated work such as centrifugation.

Second Embodiment

Figure 14:
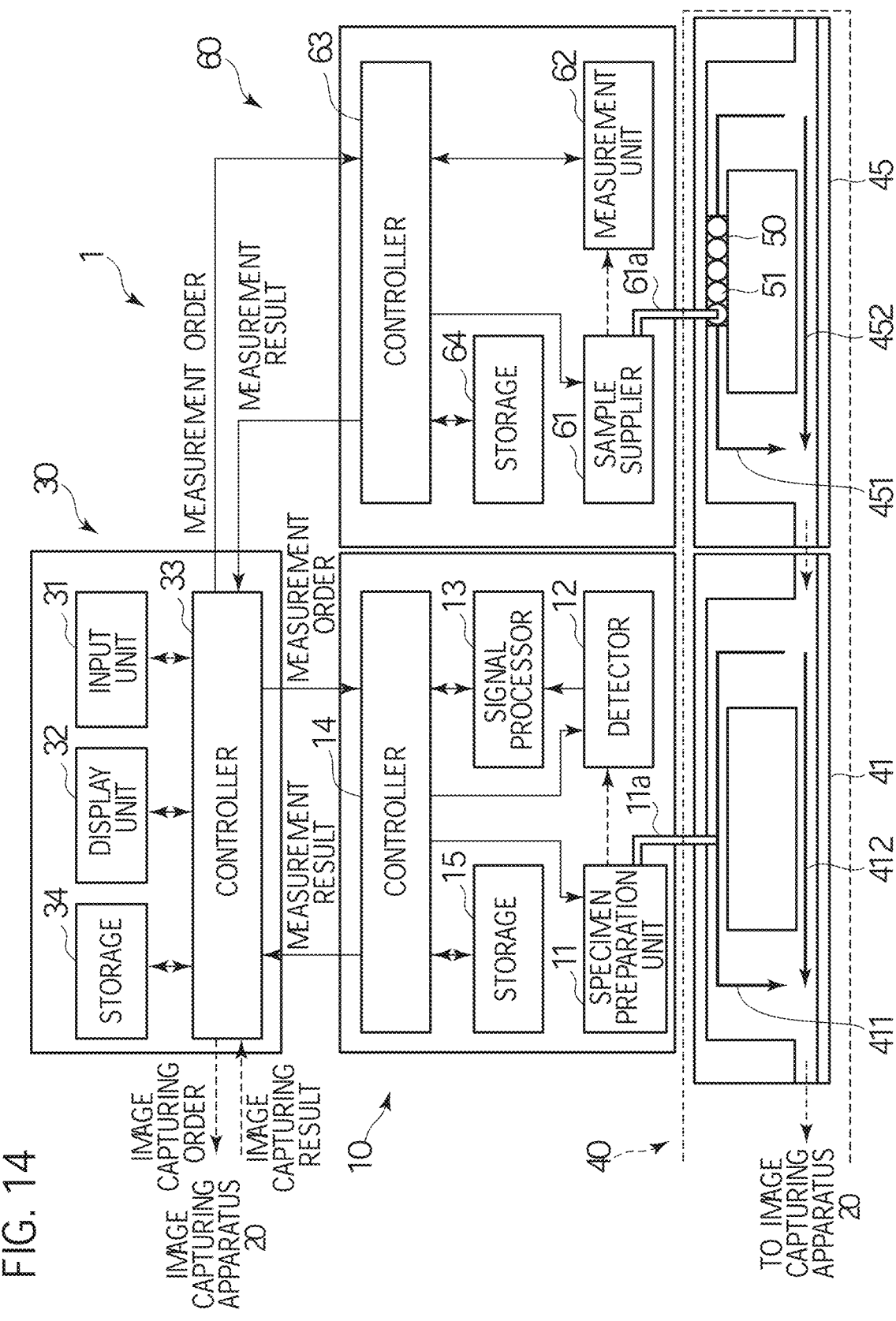
FIG. 14 is a diagram illustrating the configuration of a urine analysis system according to a second embodiment.

As illustrated in FIG. 14, in urine analysis system 1 in a second embodiment, second testing apparatus 60 is added upstream of testing apparatus 10. Conveyance unit 45 is disposed on the front side of second testing apparatus 60. Second testing apparatus 60 is a urine qualitative apparatus that spot-applies a urine sample on test paper and performs tests of urine protein, urine sugar, and the like. Conveyance unit 45 has the same configuration as the configuration of conveyance units 41 and 42. Conveyance unit 45 is controlled by controller 44 of conveyance apparatus 40. When the urine sample is measured by second testing apparatus 60, conveyance unit 45 conveys sample rack 50 with first conveyance path 451. When the urine sample is not measured by second testing apparatus 60, conveyance unit 45 conveys sample rack 50 to conveyance unit 41 with second conveyance path 452. Second conveyance path 452 is connected to second conveyance path 412 of conveyance unit 41.

Second testing apparatus 60 includes sample supplier 61, measurement unit 62, controller 63, and storage 64.

Sample supplier 61 includes suction unit 61a that sucks a urine sample. Suction unit 61a is configured from a pipe-like suction tube. Sample supplier 61 supplies the urine sample sucked by suction unit 61a to measurement unit 62. Measurement unit 62 extracts test paper necessary for measurement from a test paper feeder and spot-applies the urine sample on the extracted test paper. Measurement unit 62 detects a color of the test paper, on which the urine sample is spot-applied, with a color sensor and transmits a detection result to controller 63. Controller 63 includes an arithmetic processing circuit such as a CPU. Storage 64 includes memories such as a ROM, a RAM, and a hard disk. The storage 64 retains various kinds of information necessary for control by controller 63. Storage 64 is also used as a work region when controller 63 performs control.

Controller 63 controls the components in the second test apparatus 60 according to computer programs stored in storage 64. Controller 63 causes storage 64 to store the detection result transmitted from measurement unit 62. Controller 63 analyzes the detection result transmitted from measurement unit 62 and acquires, as a measurement result, quantitative levels of measurement items included in the urine sample. Controller 63 causes storage 64 to store the obtained measurement result and transmits the measurement result to controller 33 of management apparatus 30 together with identification information of the urine sample.

Controller 33 of management apparatus 30 performs the same processing as the processing illustrated in FIG. 10A on the measurement result received from second testing apparatus 60. When receiving the measurement result in S101, in S102, controller 33 registers the received measurement result in the database in storage 34 in association with the identification information. In S103, controller 33 determines based on the received measurement result whether image capturing by image capturing apparatus 20 is necessary for the urine sample having the received identification number. When it is determined in S104 that the image capturing is necessary, controller 33 creates an image capturing order and causes storage 34 to store the image capturing order in associate with the identification number. When it is determined in S104 that the image capturing is unnecessary, controller 33 ends the processing without creating an image capturing order.

When performing the processing illustrated in FIG. 10A on the measurement result received from second testing apparatus 60, in the processing in S103, controller 33 of management apparatus 30 refers to a first condition table and a second condition table illustrated in FIGS. 15A and 15B. For example, when a mode of image capturing processing in image capturing apparatus 20 is only the normal mode, controller 33 refers to the first condition table illustrated in FIG. 15A in the processing in S103. When the mode of the image capturing processing in image capturing apparatus 20 is a mode in which the close inspection mode is also possible, controller 33 refers to the second condition tale illustrated in FIG. 15B in the processing in S103.

When referring to the first condition table, controller 33 compares quantitative levels of measurement items included in the urine sample and thresholds of the measurement items described in the first condition table. When the level of at least one measurement item exceeds the threshold, controller 33 determines that the image capturing processing by image capturing apparatus 20 is necessary and generates an image capturing order. In this case, controller 23 of image capturing apparatus 20 executes image capturing and analysis processing by the normal mode on the urine sample for which the image capturing order is generated. When the levels of all of the measurement items do not exceed the thresholds, controller 33 determines that the image capturing processing by image capturing apparatus 20 is unnecessary.

Note that controller 33 may determine based on the measurement result obtained by testing apparatus 10 whether at least one morbid cast, which usually does not appear in a urine sample of a healthy person, is present in the urine sample of the subject. When determining that at least one morbid cast is present, controller 33 may generate an image capturing order. The user can perform operation for confirming a captured image and, when a morbid cast is absent, omitting stereoscopic observation. When a large number of flat epithelial cells are present in a urine sample of a male, there is a suspicion of urethritis due to trichomonas or chlamydia. Therefore, when determining based on the measurement result obtained by testing apparatus 10 that epithelial cells are present in a urine sample of a male by a number equal to or larger than a predetermined value, controller 33 may generate an image capturing order. When determining based on the measurement result obtained by testing apparatus 10 that an epithelial cell is present in a urine sample of a female, controller 33 may generate an image capturing order. In the case of the female, epithelial cell deriving from pudenda or vagina are easily mixed together with red blood cells, white blood cells, and the like even if there is not abnormality in a urinary system. Therefore, the user can perform operation for confirming a captured image and, if the epithelial cell is a flat epithelial cell, omitting microscopic observation.

Besides, when the measurement result of testing apparatus 10 indicates that classification error of particles, for example, classification error between red blood cells and crystals occurs, controller 33 may generate an image capturing order. Conditions for generating an image capturing order can be set in management apparatus 30 as appropriate according to operation of a user facility. By performing analysis of the particles in the urine sample based on both of a measurement result by a flow cytometry method in testing apparatus 10 and the images obtained by image capturing apparatus 20, it is possible to reduce the number of times of the microscopic observation having a large burden on the user and improve test efficiency when the microscopic observation is performed.

When referring to the second condition table, first, controller 33 compares the qualitative levels of the measurement items included in the urine sample and thresholds of the measurement items described in the second condition table. When the level of at least one measurement item exceeds the threshold, controller 33 determines that the image capturing processing by image capturing apparatus 20 is necessary. Further, controller 33 checks whether "protein" is included in the measurement item, the level of which exceeds the threshold. If "protein" is included in the measurement item, the level of which exceeds the threshold, controller 33 sets the close inspection mode as the mode of the image capturing and analysis processing. If "protein" is not included in the measurement item, the level of which exceeds the threshold, controller 33 sets the normal mode as the mode of the image capturing and analysis. In this case, controller 23 of image capturing apparatus 20 executes the image capturing and analysis processing by the close inspection mode or the normal mode on the urine sample for which the image capturing order is generated. When the levels of all of the measurement items do not exceed the thresholds, controller 33 determines that the image capturing processing by image capturing apparatus 20 is unnecessary.

As in the first embodiment, concerning the first condition table and the second condition table illustrated in FIGS. 15A and 15B, the user may be able to optionally set the thresholds and the conditions of the close inspection mode. As the conditions of the close inspection mode, when thresholds for the close inspection mode larger than the thresholds for image capturing are set and a level of a measurement item is equal to or larger than the threshold for the close inspection mode, the close inspection mode may be set as the mode of the image capturing and the analysis by image capturing apparatus 20.

In the second embodiment, as in the first embodiment, controller 44 of conveyance apparatus 40 acquires an image capturing order based on a measurement result of second testing apparatus 60 from management apparatus 30. That is, in S201 in FIG. 11A, controller 44 inquiries about an image capturing order of the urine sample in sample container 51 held by the conveyance target sample rack 50. In S202, even if image capturing orders based on the measurement result of testing apparatus 10 are not present for all of the urine samples, if an image capturing order based on the measurement result of second testing apparatus 60 is present for at least one urine sample, in S203, controller 44 conveys the conveyance target sample rack 50 with first conveyance path 421. Consequently, the image capturing target urine sample on sample rack 50 is sucked to image capturing apparatus 20 by suction unit 21a. The image capturing apparatus performs image capturing and analysis for the urine sample according to the mode included in the image capturing order.

When second testing apparatus 60 performs measurement, it is desirable that a region where a measurement result of second testing apparatus 60 is displayed is included in the browsing screen illustrated in FIG. 12. Alternatively, a measurement result displayed in region 301 may be switched between a measurement result of testing apparatus 10 and a measurement result of second testing apparatus 60 by a switching button.

According to the second embodiment, the user can simply and accurately diagnose, by referring to the cell images, a condition of a disease that is not easily accurately diagnosed from the measurement result of the testing apparatus 60. In particular, in the second embodiment, a urine sample not subjected to image capturing and analysis from a urinary sediment measurement result of testing apparatus 10 is sometimes subjected to image capturing and analysis from a urine qualitative measurement result of second testing apparatus 60. Therefore, the user can more appropriately diagnose a urine sample having a suspected condition of a disease by confirming the cell images.

<Modification>

In the determination processing in S103 in FIG. 10A, the first and second condition tables illustrated in FIGS. 10B and 10C and the first and second condition tables illustrated in FIGS. 15A and 15B may be changed according to sex and age of a subject and a type of a facility that samples the urine sample. For example, in the case of an infant or a baby, a threshold for determining whether to perform image capturing is set lower than that for an adult. In the case of a female, since an epithelial cell deriving from vagina is easily detected, a threshold for the epithelial cells is set higher than that for a male. For urine samples sampled in a urology department and a pediatric department, a threshold for determining whether to perform image capturing is set lower than that for other facilities, which makes it more likely to generate an image capturing order such that a more highly accurate test is possible for the second condition table, in the case of the urine sample of an infant and a baby, conditions for the close inspection mode are set lower than those for an adult to make it more likely to perform image capturing and analysis by the close inspection mode. Depending on sex and facilities, the conditions of the close inspection mode are changed as explained above. For example, the user can optionally set such changes. Further, the user may be able to set, for each of subjects, for example, according to a condition of a disease of the subject, for the measurement items, the threshold for determining whether image capturing is necessary and the conditions of the close inspection mode.

In this case, as illustrated in FIG. 15C, the processing of management apparatus 30 is changed. In a flowchart of FIG. 15C, S111 is added between S102 and S103. Processing other than processing in S111 is the same as the processing in FIG. 10A. In S111, controller 33 of management apparatus 30 refers to the database and discriminates sex and age of a subject whose urine sample is sampled and a type of a facility that samples the urine sample. Controller 33 changes, based on the discriminated sex, age, and type of the facility, in the first and second tables, the threshold for determining whether image capturing is necessary and the conditions of the close inspection mode to contents set by the user in advance. Controller 33 performs the determination in S103 using the first and second tables changed in this way. Processing after S103 is the same as the processing in FIG. 10A.

According to the modification, it is possible to accurately execute the image capturing and analysis processing according to individual specific circumstances and situations. Therefore, the user can perform more highly accurate diagnosis by referring to the browsing screen.

Third Embodiment

In a third embodiment, a configuration example of a screen displayed on display unit 32 of management apparatus 30 when second testing apparatus 60 is added upstream of testing apparatus 10 as in the second embodiment is explained.

Figure 16:
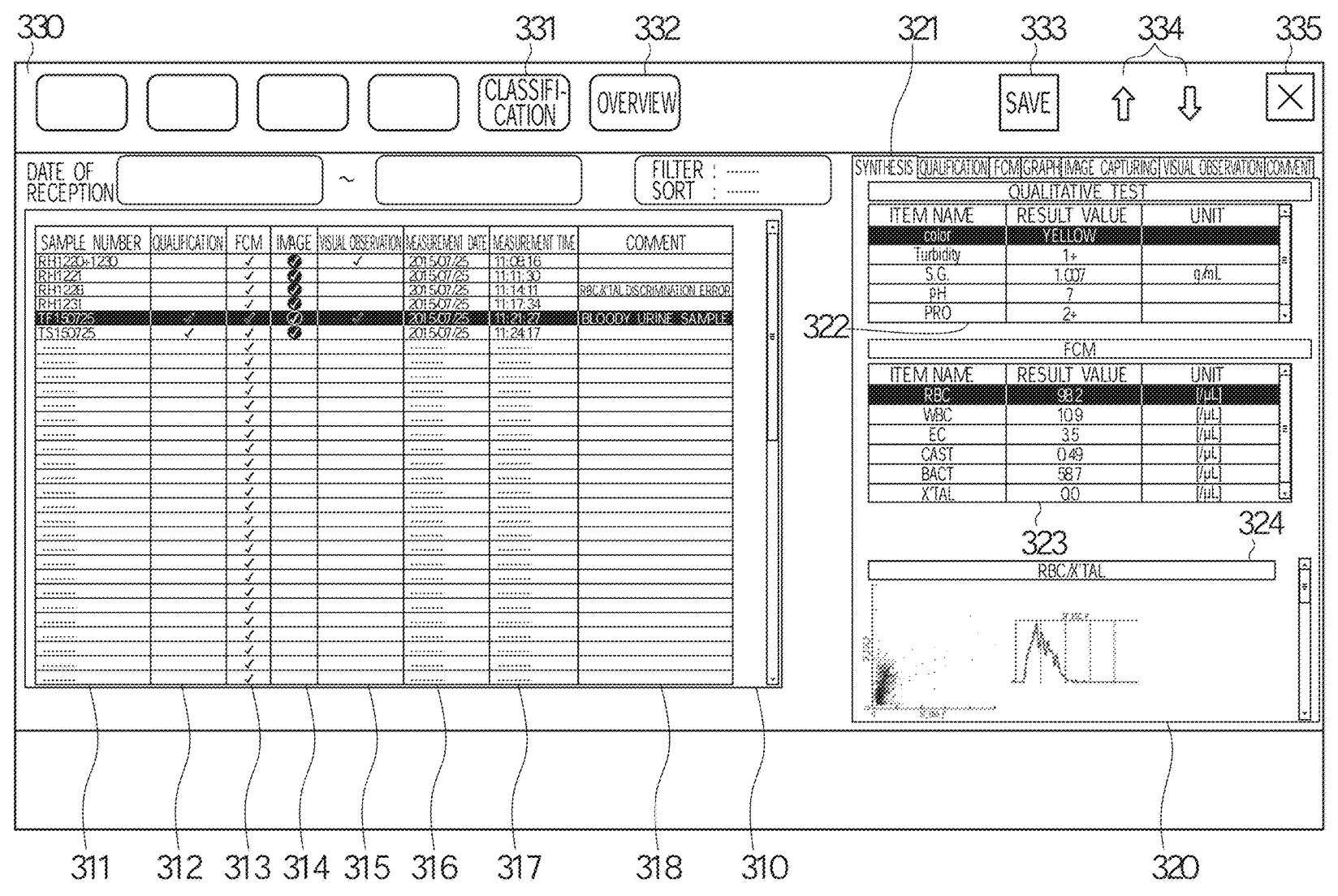

When predetermined operation is performed via input unit 31, a list screen illustrated in FIG. 16 is displayed. List screen includes list display region 310, measurement result display region 320, and button region 330.

A list of test states of samples are displayed in list display region 310. In measurement result display region 320, kinds of information based on a measurement result by testing apparatus 10, a measurement result by second testing apparatus 60, and a captured image captured by image capturing apparatus 20 are displayed to be capable of being switched according to an input by input unit 31. The switching of the display in measurement result display region 320 is performed by operation on tab 321 as explained below. Various buttons are disposed in button region 330.

List display region 310 includes sample number item 311, qualitative item 312, FCM item 313, image item 314, visual observation item 315, measurement date item 316, measurement time item 317, and comment item 318.

An identification number of a urine sample is displayed in sample number item 311. Qualitative item 312 indicates whether urine qualitative measurement is performed by second testing apparatus 60 on the urine sample having the identification number displayed in sample number item 311. FCM item 313 indicates whether urinary sediment measurement is performed by testing apparatus 10 on the urine sample having the identification number displayed in sample number item 311. Image item 314 indicates whether image capturing is already performed by image capturing apparatus 20 on the urine sample having the identification number displayed in sample number item 311.

Visual observation item 315 indicates whether a visual observation test is performed on the urine sample having the identification number displayed in sample number item 311. In the third embodiment, when a visual observation test by microscopic observation is performed on the urine sample, a result of the visual observation test is input to management apparatus 30 and stored in the database. Date and time when the measurement is performed by testing apparatus 10 on the urine sample having the identification number displayed in sample number item 311 are respectively displayed in measurement date item 316 and measurement time item 317.

In comment item 318, a comment on the urine sample having the identification number displayed in sample number item 311 is displayed. As explained below, a user such as a laboratory technician optionally inputs the comment. Besides, the comment includes a comment received from testing apparatus 10. For example, when a particle having an error in classification is present in the urine sample, testing apparatus 10 transmits information indicating the particle having an error in the classification and detail of the classification error to management apparatus 30 together with a measurement result.

As one kind of the classification error, for example, in the scattergrams illustrated in FIGS. 3A to 3E, boundaries of particles overlap and the particles cannot be accurately discriminated. In this case, information indicating "discrimination error" as a detail of the classification error is transmitted from testing apparatus 10 to management apparatus 30 together with information indicating the particles determined as an error in the classification. Management apparatus 30 displays, in comment item 318 illustrated in FIG. 16, a description indicating the particles determined as the classification error and the "discrimination error". For example, when a red blood cell and a crystal cannot be accurately discriminated, a character string "RBC/X'TAL discrimination error" is displayed in comment item 318.

The list table displayed in list display region 310 can be scrolled up and down by a scroll bar disposed at the right end of list display region 310.

A field for inputting a range of reception dates and a field for inputting terms used for sorting are disposed on the upper side of list display region 310. The fields are fields for filtering the urine samples displayed in list display region 310 according to the range of reception dates and the terms or rearranging the urine samples displayed in list display region 310 according to the terms.

In measurement result display region 320, display content can be switched by tab 321. Tab 321 includes seven items of synthesis, qualitative, FCM, graph, image capturing, visual observation, and comment. In FIG. 16, display content at the time when tab 321 of synthesis is selected via input unit 31 is illustrated. In this case, in measurement result display region 320, qualitative result region 322 and sediment result region 323 are disposed to be vertically arranged. Graph region 324 is disposed under qualitative result region 322 and sediment result region 323.

Qualitative result region 322 is a region for displaying a qualitative measurement result by second testing apparatus 60. Sediment result region 323 is a region for displaying a sediment measurement result by testing apparatus 10. Graph region 324 is a region for displaying the measurement result by testing apparatus 10 as various graphs such as scattergrams and histograms. As in the case of FIG. 12, in the scattergrams, colors of plots are changed for each of the particles.

In measurement result display region 320, a measurement result for the urine sample selected in the list table of list display region 310 is displayed. Display of qualitative result region 322, sediment result region 323, and graph region 324 can be scrolled up and down by a scroll bar disposed at the right end.

Concerning the urine sample selected in the list table of list display region 310, when a command of classification error is received from testing apparatus 10, a mark for indicating the classification error, for example, a sign "*" is added to a field of a result value of a particle having the classification error among the particles displayed in sediment result region 323. Consequently, the user can learn that the classification error occurs in the particle without referring to comment item 318 of list display region 310.

Button region 330 includes operation buttons 331 to 335. Operation button 331 is a button used in classifying cell images as explained below. Operation button 332 is a button for displaying a cell image of a urine sample selected in the list table of list display region 310. Operation button 333 is a button for saving, at any timing, a classification result of the cell images and the comment described in comment item 318. Operation button 334 is a button for performing movement operation of a urine sample. When the user pushes up and down arrows of operation button 334 via input unit 31, the urine sample selected in list display region 310 is vertically switched. According to the switching of the urine sample, display content of measurement result display region 320 is switched to information corresponding to a urine sample selected anew. Operation button 335 is a button for closing the screen.

Figure 17:
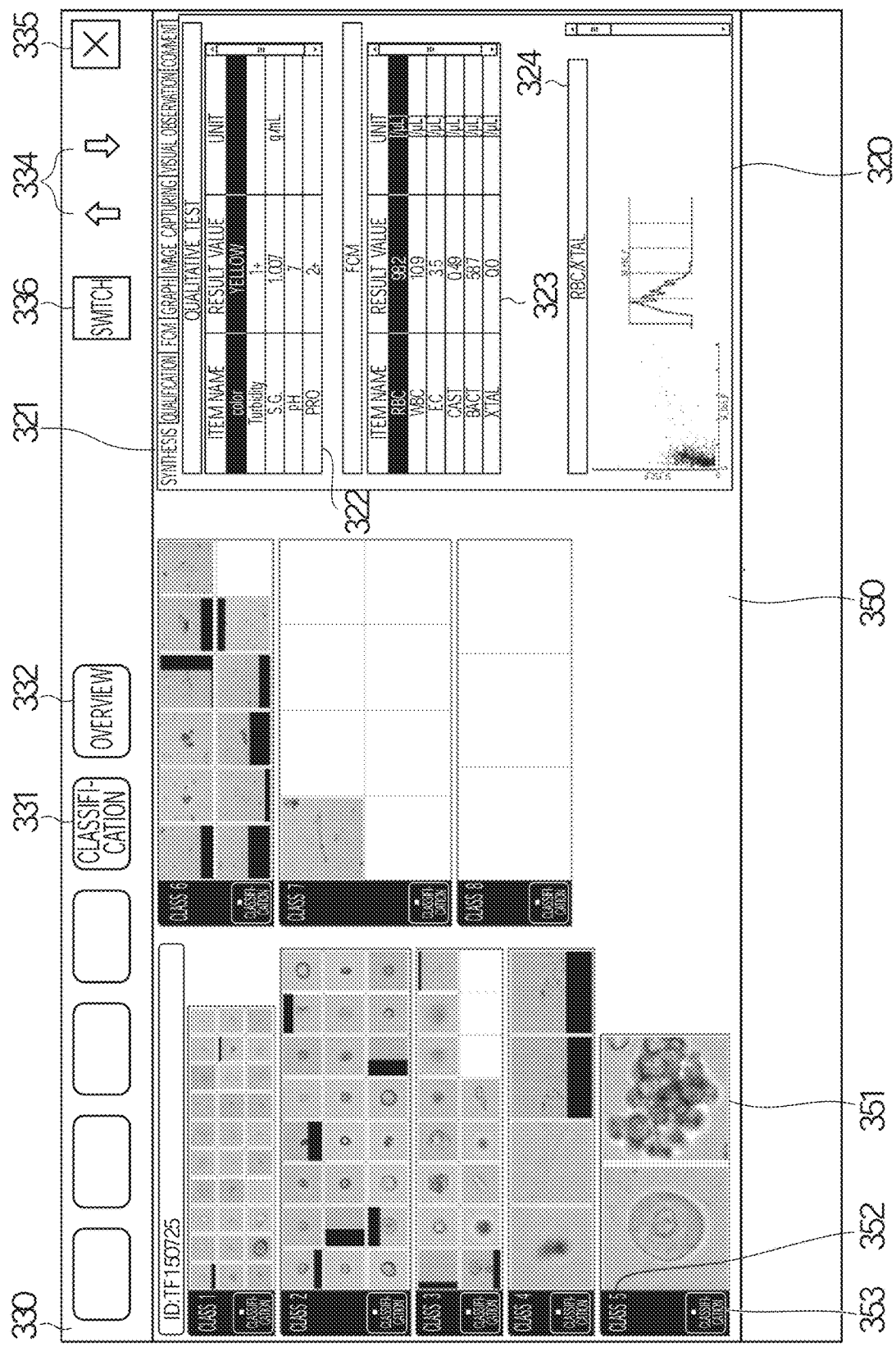
FIG. 17 is a diagram illustrating the configuration of an overview screen at the time when a tab of synthesis is pressed according to the third embodiment.

When the user presses operation button 332 after selecting one urine sample in the list table of list display region 310 via input unit 31, the screen of display unit 32 is switched to a screen illustrated in FIG. 17. This screen is hereinafter referred to as overview screen.

In the overview screen, list display region 310 is replaced with cell image display region 350 in the screen illustrated in FIG. 16. In cell image display region 350, cell images acquired by image capturing apparatus 20 are classified and displayed for each of predetermined indicators. The cell images are classified into eight classes according to the sizes of particles and displayed in cell image display region 350. The indicators for classifying the cell images are not limited to the sizes and may be other parameters for specifying shapes and the like.

Each of divisions of the classes includes region 351, label 352, and operation button 353. In region 351, cell images of the class are displayed. In label 352, a character string for identifying the class is displayed. Operation button 353 is operated when the cell images of the class are classified into particles of specific kinds. The classification of the cell images can also be performed by pressing operation button 331 of button region 330 via input unit 31. The user can proceed with the classification of the cell images in order from class 1 by operating operation button 331 via input unit 31. The classification operation of the cell images performed by the user is explained below with reference to FIG. 25.

The number of cell images displayable in region 351 is determined for each of the classes. For example, in region 351 of class 4, only four cell images are displayable. Fifth or more cell images cannot be displayed. A function for switching, when the user clicks label 352 of each of the classes via input unit 31, display content of cell image display region 350 to display content for displaying all of the cell images included in the class may be given. In this case, a scroll bar for scrolling the cell images is added to cell image display region 350 as appropriate.

In the overview screen illustrated in FIG. 17, operation button 333 in the screen illustrated in FIG. 16 is replaced with operation button 336. Operation button 336 is a button for switching an overview screen before the cell images are classified and an overview screen after the cell images are classified (a classification result screen: see FIG. 26).

In the overview screen illustrated in FIG. 17, a urinary sediment measurement result by testing apparatus 10 and a urine qualitative measurement result by second testing apparatus 60 are vertically displayed side by side in measurement result display region 320. The user can grasp, by cross checking the two measurement results, items in which the two measurement results are deviate from each other.

For example, when a result value of protein is low in the measurement result displayed in qualitative result region 322, although a result value of a cast is high in the measurement result displayed in sediment result region 323, it is seen that the cast is likely to be not properly measured in testing apparatus 10. In this case, the user closely visually examines the cell images of the class corresponding to the cast and carefully confirms whether the cast is included in the urine sample in cell image display region 350. In this way, it is possible to more efficiently and accurately confirm whether the cast is included in the urine sample.

Figure 18:
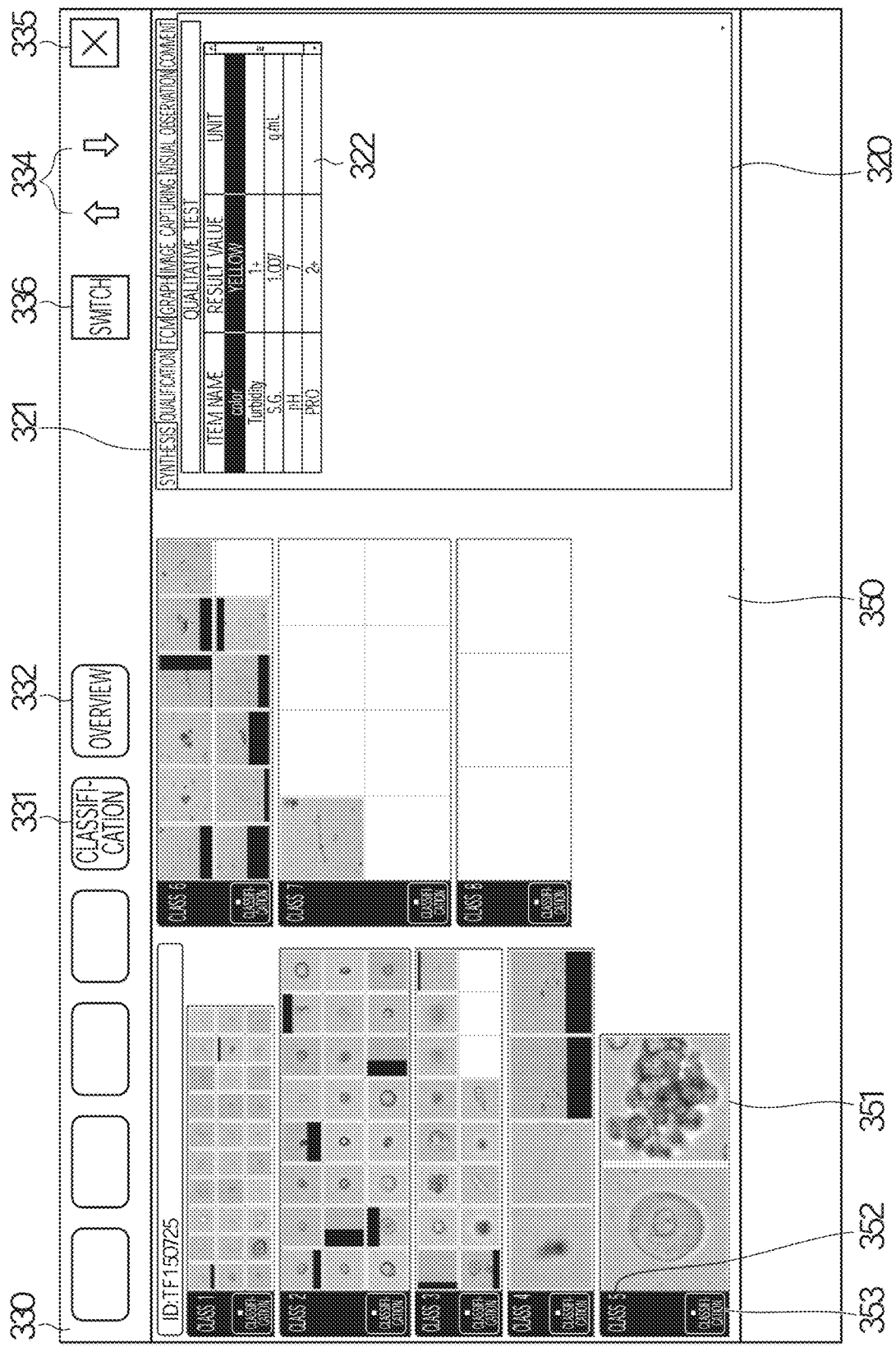
FIG. 18 is a diagram illustrating the configuration of an overview screen at the time when a tab of qualification is pressed according to the third embodiment.

In the overview screen illustrated in FIG. 17, when qualitative type 321 is selected via input unit 31, measurement result display region 320 is switched to display content illustrated in FIG. 18. As illustrated in FIG. 18, when the qualitative tab 321 is selected, only qualitative result region 322 is set in measurement result display region 320. In qualitative result region 322, a measurement item name and an item of a result value indicating the measurement result are displayed. In an item of a unit, a unit of the result value is displayed. In an overview screen illustrated in FIG. 18, the user can evaluate the cell images of the classes based on only a qualitative measurement result.

Figure 19:
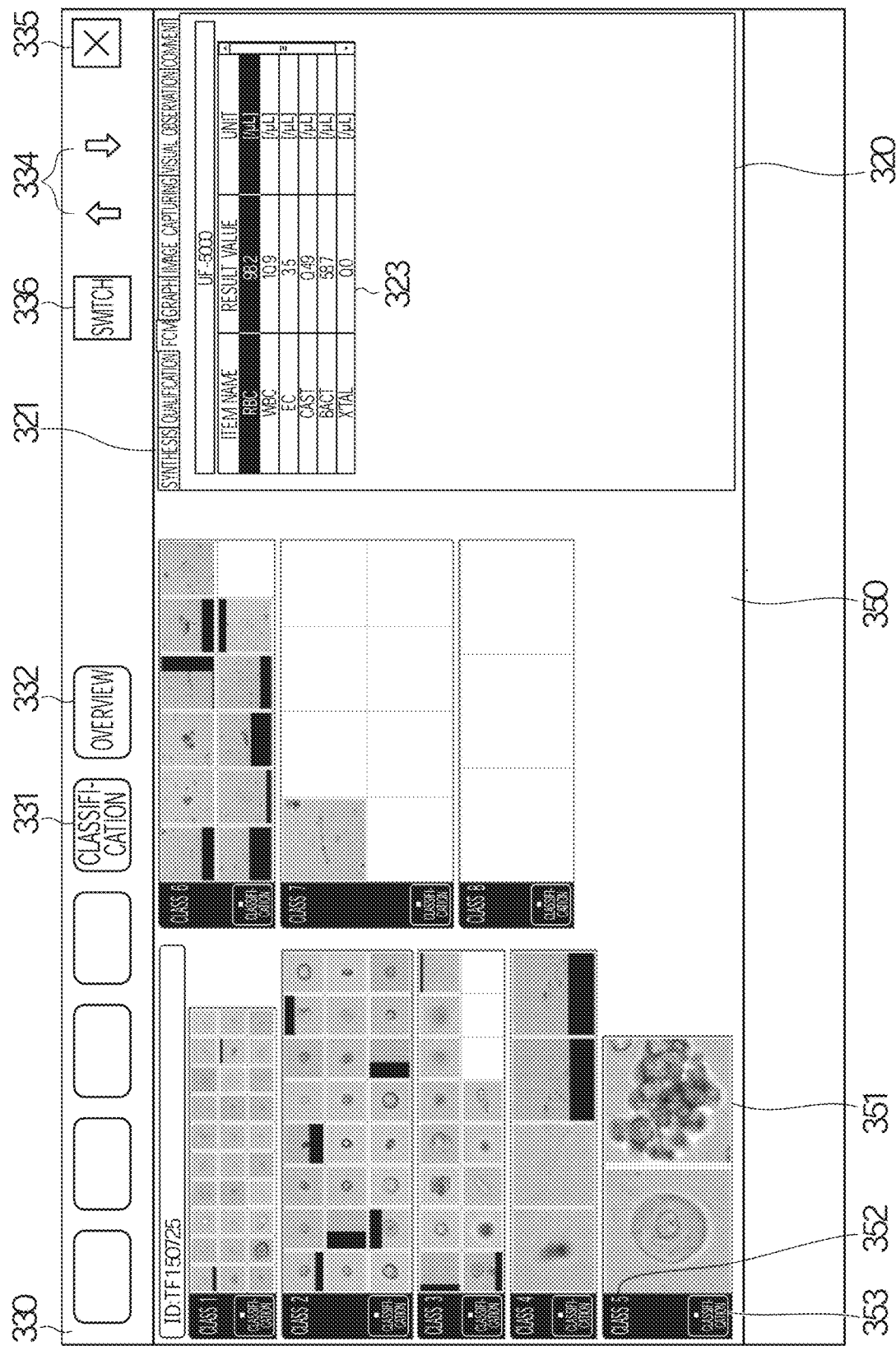
FIG. 19 is a diagram illustrating the configuration of an overview screen at the time when a tab of FCM is pressed according to the third embodiment.

In the overview screen illustrated in FIG. 18, when FCM tab 321 is selected via input unit 31, measurement result display region 320 is switched to display content illustrated in FIG. 19. As illustrated in FIG. 19, when FCM tab 321 is selected, only sediment result region 323 is set in measurement result display region 320. In sediment result region 323, a measurement item name and an item of a result value indicating the measurement result are displayed. In an item of a unit, a unit of the result value is displayed. In an overview screen illustrated in FIG. 19, the user can evaluate the cell images of the classes based on only a sediment measurement result.

As explained above, in the field of the result value of the particle having the classification error, the mark for indicating the classification error, for example, the sign "*" is added. Consequently, the user can also learn from the display content of the overview screen illustrated in FIG. 19 that classification error occurs in a certain particle. Consequently, for example, the user can take a measure for more carefully closely inspect the cell image of the class corresponding to the particle having the classification error.

Figure 20:
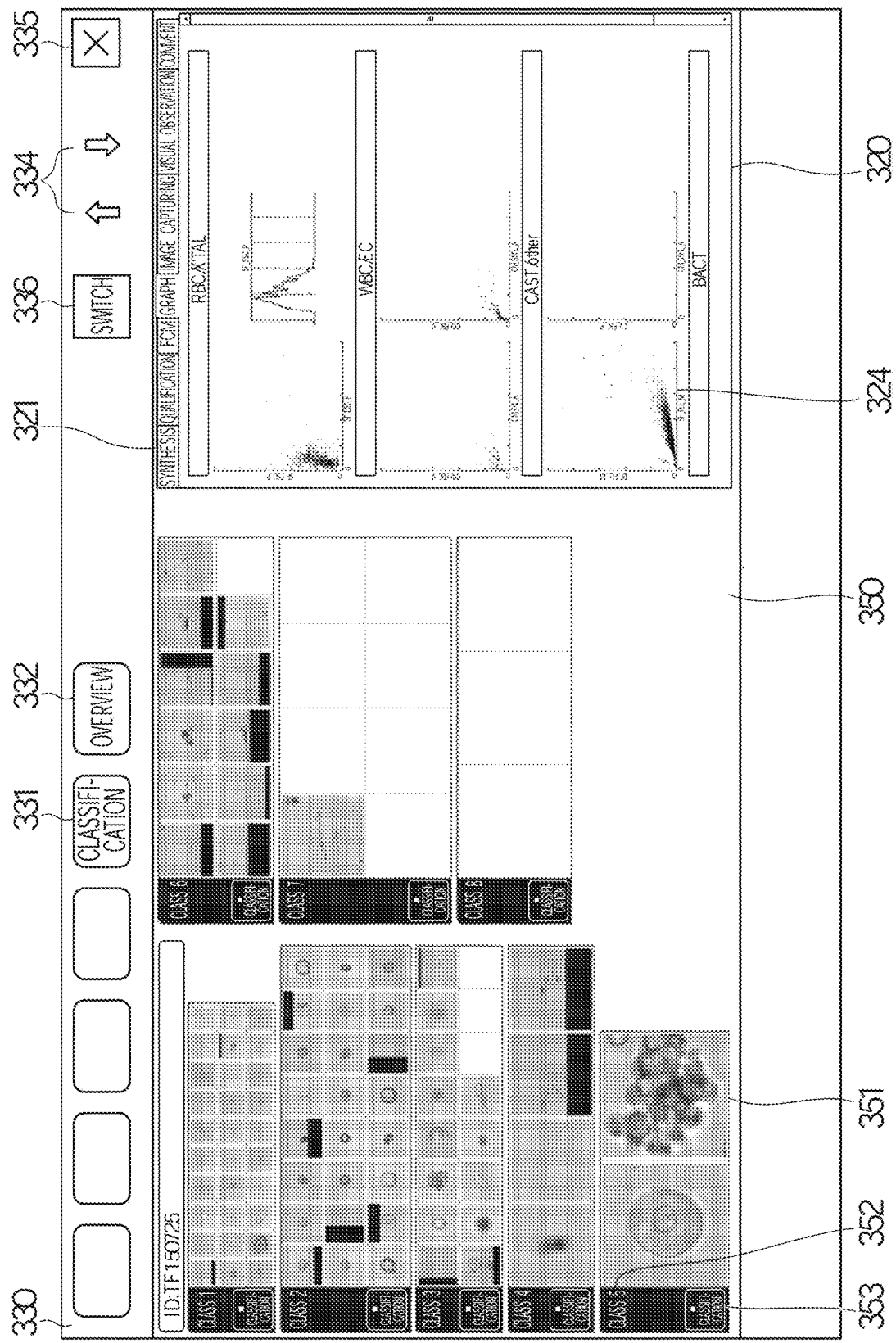
FIG. 20 is a diagram illustrating the configuration of an overview screen at the time when a tab of a graph is pressed according to the third embodiment.

In the overview screen illustrated in FIG. 19, when graph tab 321 is selected via input unit 31, measurement result display region 320 is switched to display content illustrated in FIG. 20. As illustrated in FIG. 20, when graph tab 321 is selected, only graph region 324 is set in measurement result display region 320. In graph region 324, graphs are dividedly displayed for respective kinds of particles. As explained above, in the scattergrams, colors of plots are changed among the kinds of particles. The user can grasp measurement states of the particles by referring to graph region 324. Consequently, when grasping a measurement result to which attention should be paid, for example, the user can take a measure for more carefully closely inspecting the cell image of the class corresponding to the measurement result.

Figure 21:
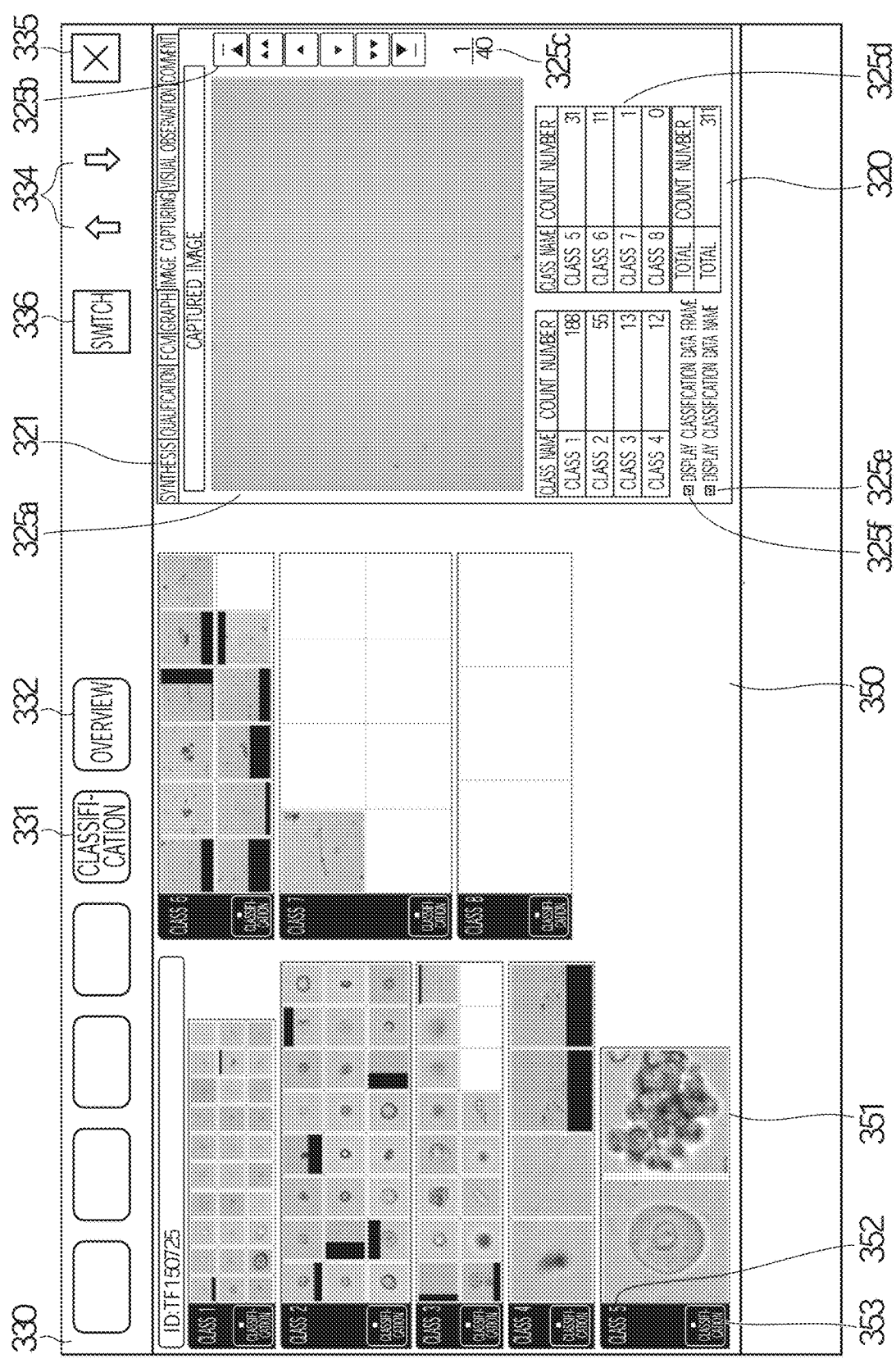
FIG. 21 is a diagram illustrating the configuration of an overview screen at the time when a tab of image capturing is pressed according to the third embodiment.

In the overview screen illustrated in FIG. 20, when image capturing tab 321 is selected via input unit 31, measurement result display region 320 is switched to display content illustrated in FIG. 21. As illustrated in FIG. 21, when image capturing tab 321 is selected, captured image region 325a, operation buttons 325b, image number 325c, and counting result region 325d are set in measurement result display region 320.

As explained above, when performing the imaging in the normal mode, image capturing apparatus 20 acquires forty captured images while changing an image capturing position with respect to one urine sample. When performing the imaging in the close inspection mode, image capturing apparatus 20 acquires eighty captured images with respect to one urine sample. One of the captured images acquired in this way is displayed in captured image region 325a.

Image capturing apparatus 20 transmits the forty captured images captured in the normal mode or the eighty captured images captured in the close inspection mode, cell images segmented from the captured images, and information indicating segmentation positions of the cell images on the captured images to management apparatus 30 together with a sample number of the urine sample.

Operation buttons 325b are buttons for feeding a captured image displayed in captured image region 325a in a forward direction or a reverse direction. Operation buttons 325b at the top and the bottom are respectively buttons for displaying first and last captured image. Two operation buttons 325b in the center are respectively buttons for feeding captured images one by one. Second operation button 325b from the top and the second operation buttons 325b from the bottom are respectively buttons for fast-rewinding and fast-forwarding the captured images.

A denominator of image number 325c indicates the number of captured images acquired for the urine sample selected in list display region 310 illustrated in FIG. 16. When image capturing is performed in the normal mode, the denominator of image number 325c is 40, which is the number of captured images in the normal mode. When image capturing is performed in the close inspection mode, the denominator of image number 325c is 80, which is the number of captured images in the close inspection mode. By referring to the denominator of image number 325c, it is seen in which of the normal mode and the close inspection mode the image capturing operation is performed.

A numerator of image number 325c indicates image capturing order of the captured image displayed in captured image region 325a. When a captured image captured first for the urine sample is displayed in captured image region 325a, the numerator of image number 325c is 1. When the captured image displayed in captured image region 325a is fed by operation on operation button 325b, the numerator of image number 325c changes.

The user can grasp a state and a tendency of particles included in the urine sample by operating operation button 325b via input unit 31 to feed the captured image. The user can appropriately evaluate the cell images displayed in cell image display region 350 based on the information grasped in this way. For example, particles affecting diagnosis such as casts and atypical cells are found from a series of captured images, the user can take a measure for closely inspecting cell images of classes corresponding to the particles and confirming states of the cell images. In this way, it is possible to more efficiently and accurately confirm the particles included in the urine sample.

In an overview screen illustrated in FIG. 21, in counting result region 325d of measurement result display region 320, the numbers of cell images acquired for the urine sample are displayed for each of the classes. Further, a total number of cell imagers acquired for the urine sample are displayed. By referring to these displays, the user can grasp a rough tendency of the particles included in the urine sample. The user can efficiently and appropriately evaluate, based on the grasped tendency, the captured image displayed in captured image region 325a or the cell images of the classes displayed in cell image display region 350.

Measurement result display region 320 includes two check boxes 325e and 325f. When check box 325e is checked via input unit 31, a frame is added to a region where a cell image is segmented with respect to the captured image displayed in captured image region 325a. When check box 325f is checked via input unit 31, a character string indicating a classification result of the cell image is written immediately below the region where the cell image is segmented. The character image is displayed when the call image is already classified. Since the frame and the character string are added in this way, the user can more smoothly confirm the cell images included in the captured image. When a large number of call images are included in the captured image and it is hard to see the cell images if frames and character strings are displayed, the user only has to release the check of check boxes 325e and 325f via input unit 31 as appropriate.

Consequently, the user can satisfactorily confirm the cell images included in the captured image.

Figure 22:
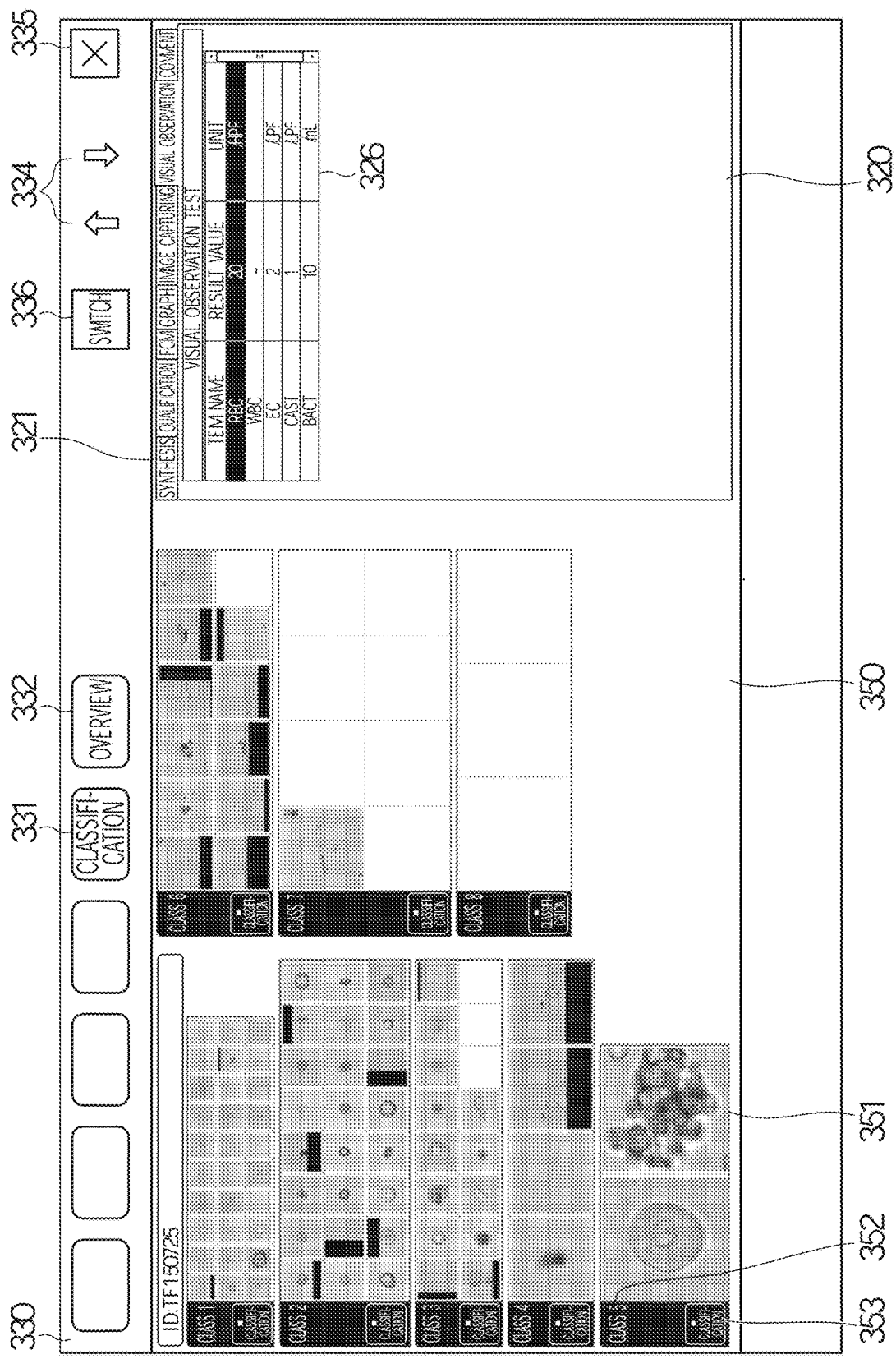
FIG. 22 is a diagram illustrating the configuration of an overview screen at the time when a tab of visual observation is pressed according to the third embodiment.

In the overview screen illustrated in FIG. 21, when visual observation tab 321 is selected via input unit 31, measurement result display region 320 is switched to display content illustrated in FIG. 22. As illustrated in FIG. 22, when visual observation tab 321 is selected, visual observation result region 326 is set in measurement result display region 320. In visual observation result region 326, a result of a visual observation test by microscopic observation is displayed. In visual observation result region 326, a test item name and an item of a result value indicating the test result are displayed. In an item of a unit, a unit of the result value is displayed. In the overview screen illustrated in FIG. 17, the user can evaluate the cell images of the classes further based on the visual observation result.

Figure 23:
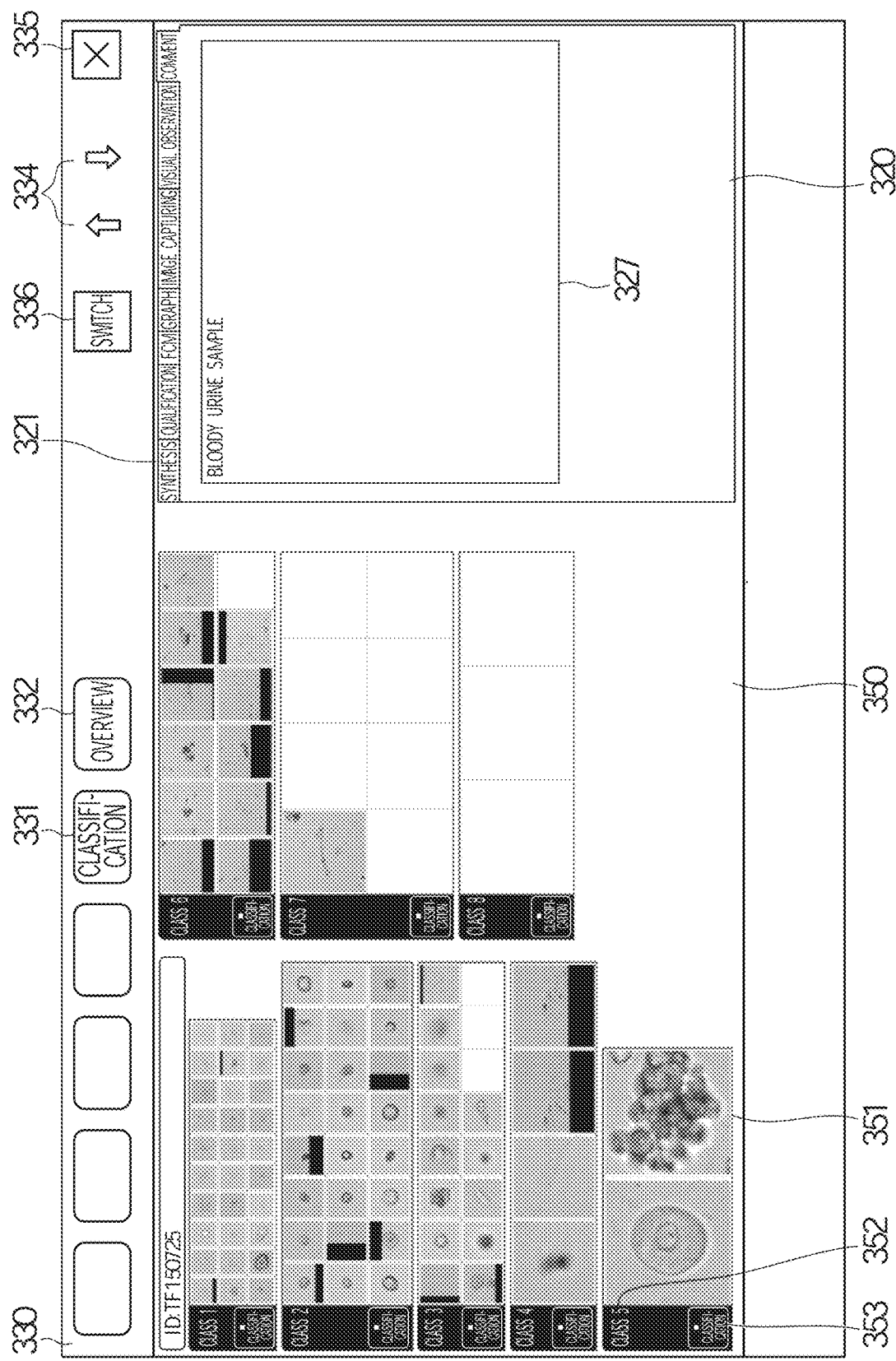
FIG. 23 is a diagram illustrating the configuration of an overview screen at the time when a tab of a comment is pressed according to the third embodiment.

In an overview screen illustrated in FIG. 22, when comment tab 321 is selected via input unit 31, measurement result display region 320 is switched to display content illustrated in FIG. 23. As illustrated in FIG. 23, when comment tab 321 is selected, comment field 327 is set in measurement result display region 320. In comment field 327, the user such as the laboratory technician is capable of inputting a comment on the urine sample as appropriate. That is, in a state in which comment field 327 is displayed in measurement result display region 320, management apparatus 30 receives input of a new comment by input unit 31. In an example illustrated in FIG. 24, a character string "erythrocyturia sample" input by the user is displayed in comment field 327.

Besides, a comment received from testing apparatus 10 is displayed in comment field 327. For example, the particle having an error in the classification as explained above in testing apparatus 10, and the detail of the classification error are displayed in comment field 327. For example, a character string indicating the detail of the classification error is displayed in comment field 327.

In an overview screen illustrated in FIG. 23, the user can efficiently and appropriately evaluate the cell images according to content of the comment displayed in comment field 327.

For example, when display of "RBC/X'TAL discrimination error" is included in comment field 327, the user can grasp that there is an error in classification of red blood cells and crystals in testing apparatus 10. In this case, the user visually closely inspects the cell images of the classes corresponding to the red blood cells and the crystals and more carefully confirms the captured images in cell image display region 350. Consequently, it is possible to efficiently and accurately classify the red blood cells and the crystals. Further, when cell images of other cells such as atypical cells are included in the cell images of the classes, it is possible to smoothly confirm the presence of the cell images. Further, the user is capable of optionally adding a comment to comment field 327. For example, the user can add an item determined by observing the overview screen to comment field 327 at any time via input unit 31. Consequently, it is possible to smoothly proceed with posterior diagnosis.

As illustrated in FIGS. 17 to 23, the overview screen includes cell image display region 350 for displaying cell images of a selected urine sample and measurement result display region 320. In cell image display region 350, cell images acquired by image capturing apparatus 20 are classified and displayed for each of predetermined sizes. In measurement result display region 320, kinds of information such as a sediment measurement result by testing apparatus 10 and the qualitative measurement result by second testing apparatus 60 is displayed to be capable of being switched by operation on tab 321.

In this way, in the overview screen, cell image display region 350 and measurement result display region 320 are included in one screen. Therefore, by switching display content of measurement result display region 320, it is possible to smoothly grasp various kinds of information to which attention should be paid in evaluation of the cell images. It is possible to appropriately and efficiently evaluate the cell images in cell image display region 350 according to the grasped information. The user can evaluate and analyze the cell images from various viewpoints grasped by referring to measurement result display region 320. Consequently, the user can more efficiently and accurately determine a condition of a disease that is not easily accurately diagnosed from the measurement results of testing apparatus 10 and second testing apparatus 60.

In general, when particles in a urine sample are set as analysis targets, it is not easy to classify and analyze the particles according to measurement results obtained by testing apparatus 10 because of circumstances peculiar to urine, for example, there are many kinds of particles that can appear, there is a relatively large width in the number of appeared particles, there is width in appearing forms of the particles such as a difference in a degree of damage, and changes in the forms and the number of the particles such as breeding of bacteria, progress of red blood cell erythrolysis, and separation of crystals easily occur according to the elapse of time from sampling.

On the other hand, in the third embodiment, as illustrated in FIGS. 17 to 23, the cell images of the urine sample are displayed on one screen together with the urinal sediment measurement result by testing apparatus 10. Further, the urine qualitative measurement result by second testing apparatus 60 is included in the screen. Moreover, in measurement result display region 320, kinds of information such as the measurement result by testing apparatus 10 and the measurement result by second testing apparatus 60 is displayed to be capable of being switched according to operation on tab 321 at any time. Therefore, the user can evaluate and analyze the cell images from various viewpoints based on the information switched and displayed as appropriate in measurement result display region 320. Therefore, it is possible to more accurately evaluate the particles peculiar to urine that can take various forms. Moreover, since the cell images, the measurement results, and the like are displayed on the same screen, the user can compare and contrast the cell images and the measurement results. Consequently, it is possible smoothly and efficiently proceed with the evaluation of the cell images.

Figure 24:
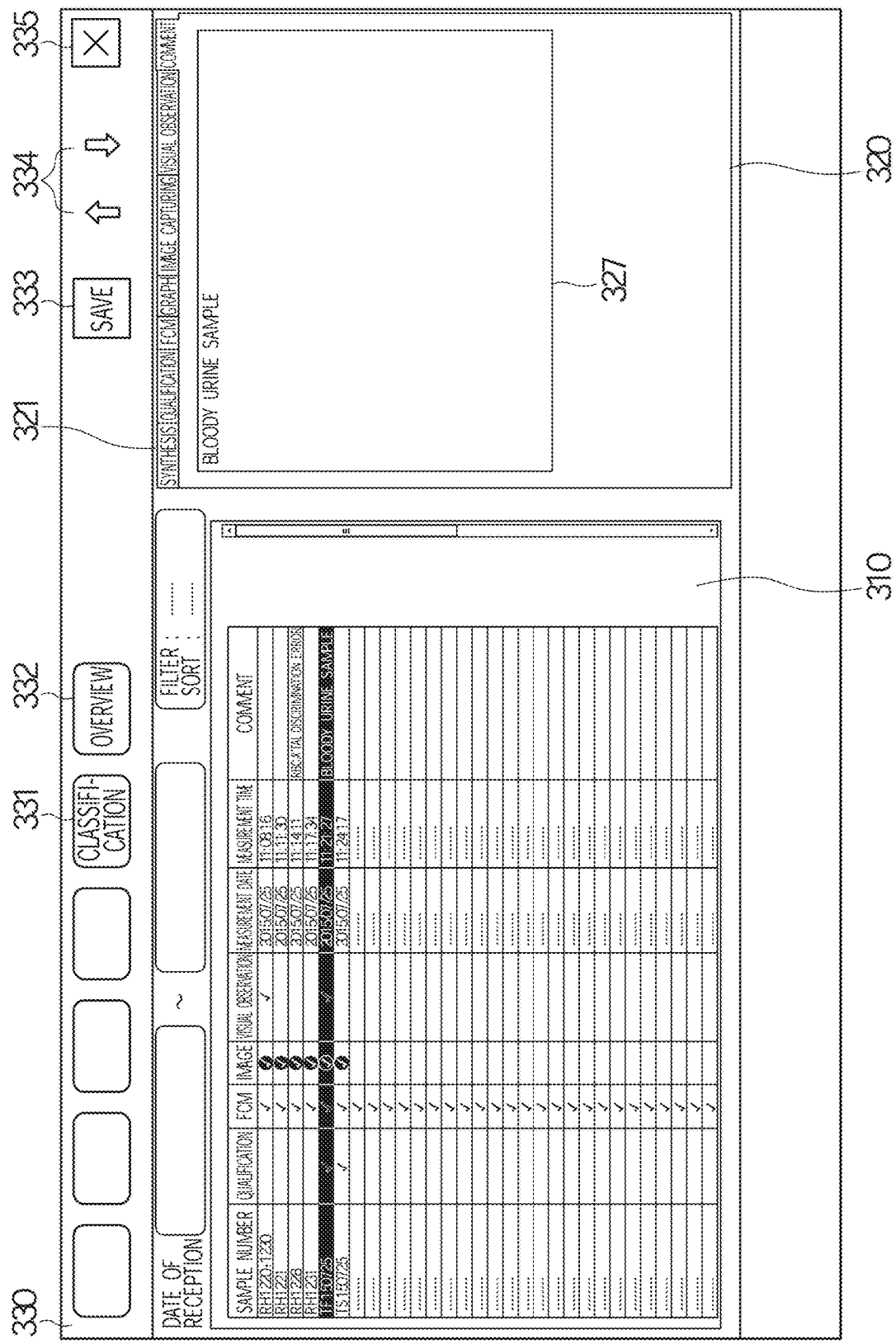
FIG. 24 is a diagram illustrating the configuration of a list screen at the time when the tab of synthesis is pressed according to the third embodiment.

Note that tab 321 in measurement result display region 320 is operable not only on the overview screens illustrated in FIGS. 17 to 23 but also on the screen of the list display illustrated in FIG. 16. When the tabs 321 of synthesis, qualitative, FCM, graph, image capturing, visual observation, and comment are respectively operated via input unit 31 on the screen of the list display, on the screen illustrated in FIG. 16, the display content of measurement result display region 320 is switched to the display contents illustrated in FIGS. 17 to 23. For example, when comment tab 321 is operated via input unit 31 on the screen illustrated in FIG. 16, a screen illustrated in FIG. 24 is displayed.

In the overview screens illustrated in FIGS. 17 to 23, the user can proceed with classification of cell images of a desired class displayed in cell image display region 350.

Figure 25:
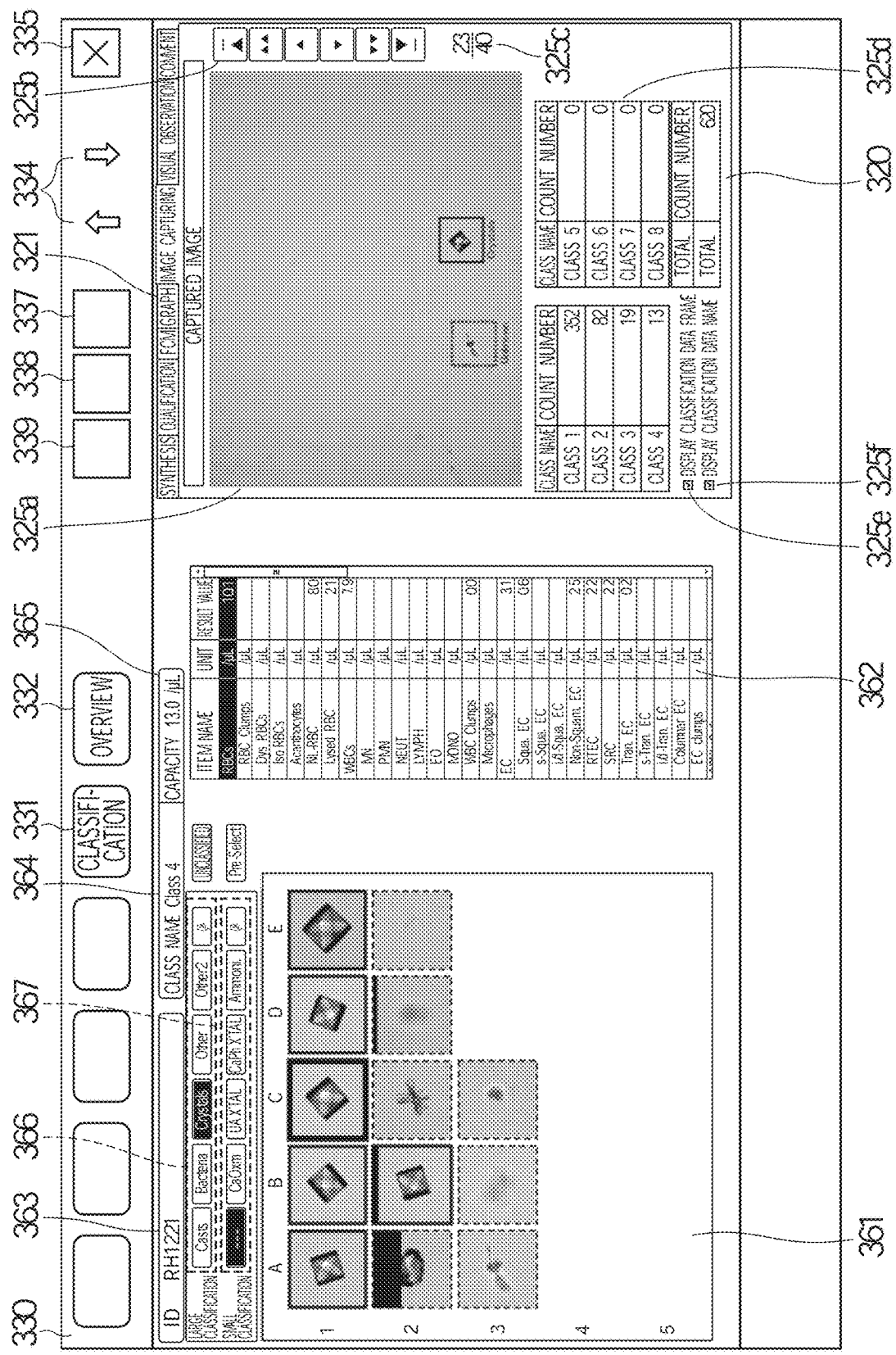
FIG. 25 is a diagram illustrating the configuration of a classification operation screen according to the third embodiment.

For example, in the overview screen in which image capturing tab 321 is pressed, when operation button 353 of class 4 in cell image display region 350 is pressed via input unit 31, a screen illustrated in FIG. 25 is displayed. This screen hereinafter referred to as classification operation screen.

As illustrated in FIG. 25, the classification operation screen includes, besides measurement result display region 320, classification target display region 361, classification result display region 362, sample ID display region 363, class display region 364, capacity display region 365, large classification selection region 366, and small classification selection region 367. Operation buttons 337 to 339 are added to button region 330.

Operation buttons 337 to 339 are buttons for simplifying classification operation. Operation button 337 is a button for releasing classification concerning all particles included in a classification target class and sets the particles in an unclassified state. Operation button 338 is a button for releasing classification of already classified cell images and returning the cell images to the unclassified state. Operation button 339 is a button for classifying all of the cell images in the unclassified state included in the classification target class into currently selected large classification and small classification.

In classification target display region 361, cell images of a class selected as a classification target are displayed. When the number of the cell images of the selected class is large and not all of the cell images can be displayed in classification target display region 361, a scroll bar is added to the right end of classification target display region 361.

In classification result display region 362, counting results of the particles after the classification is performed are displayed. Classification result display region 362 includes items indicating kinds of the particles and items of result values indicating counting results of the particles. The counting results of the particles after the classification is performed are displayed in the items of the result values. In an item of a unit, a unit of the result value is illustrated.

When the classification for the cell images is performed, the items of the result values of classification result display region 362 are updated. More specifically, as explained below, the user operates a selection button of large classification selection region 366 and a selection button of small classification selection region 367 via input unit 31 and further operates a classification target cell image, a classification for the cell image is decided. According to the decision of the classification, the items of the result values of classification result display region 362 are updated.

In sample ID display region 363, an identification number of the urine sample is displayed. In class display region 364, a class selected as a classification target is displayed. In capacity display region 365, the number of cell images of the class selected as the classification target is displayed as a number per 1 μL. In the case of the normal mode, a total volume of urine samples corresponding to all of captured images is approximately 1 μL, the number of cell images of the class selected as the classification target is displayed. On the other hand, in the case of the close inspection mode, the total volume of the urine samples corresponding to all of the captured images is approximately 2 μL. Therefore, in capacity display region 365, a number obtained by dividing the number of the cell images of the class selected as the classification target by 2 is displayed.

Large classification selection region 366 includes selection buttons. Classification candidates of cell images are respectively allocated to the selection buttons. In the selection buttons, notations indicating the classification candidates, for example, notations indicating kinds of particles such as "Casts" (cast), "Bacteria" (bacteria), and "Crystal" (crystal) are added. Further, the larger classification selection region 366 includes a selection button selected when a cell image cannot be classified into a particle of any kind. A notation such as "other" (others) or "other 2" (others 2) is added to the selection button. The right end of large classification selection region 366 includes a change button for changing a selection button group. When the change button is pressed via input unit 31, a combination of selection button groups of large classification selection region 366 is changed to a combination of other particles.

Small classification selection region 367 includes selection buttons for more finely classifying the particles selected in large classification selection region 366. Reclassification candidates of the cell images are respectively allocated to the selection buttons. Notations indicating the reclassification candidates, for example, notations indicating contents of reclassification such as "Ca0xm" (oxalic acid Ca), "UA X'TAL" (uric acid crystal), "CaPh X'TAL" (phosphoric acid Ca), and "Ammmoni." (phosphoric acid AmMg, uric acid Am) are added to the selection buttons. A button at the left end of small classification selection region 367 is a selection button selected when the reclassification cannot be performed. A change button for changing a selection button group is included in the right end of small classification selection region 367. When the change button is pressed via input unit 31, a combination of the selection button group of small classification selection region 367 is changed to a combination of other reclassification.

In classification target display region 361, markings corresponding to states of classification are added to the respective cell images. For example, a frame of an orange color is added to a cell image classified into a particle. A frame of a blue color is added to an unknown cell image that cannot be classified into any particles. A frame is not added to an unclassified cell image. A frame of a yellow color is added to a cell image selected as a classification target.

A form of the markings added to the cell images is not limited to the form of changing the colors of the frames and only has to be a form with which the classification states of the cell images can be grasped. In an example illustrated in FIG. 25, for convenience, the classification states of the cell images are indicated by the thicknesses of the frames and kinds of frame lines. A thick frame indicates a cell image selected as a classification target. A frame of a solid line thinner than the thick frame indicates a cell image classified into a particle. A broken line frame indicates an unknown cell image that cannot be classified into any particle. A frame is not added to an unclassified cell image.

In the classification operation screen illustrated in FIG. 25, when the user clicks one of the cell images displayed in classification target display region 361 via input unit 31, a captured image from which the cell image is segmented is displayed in captured image region 325a of measurement result display region 320. That is, a captured image including the selected cell image and the surroundings of the cell image is displayed in captured image region 325a. At this point, when check box 325e of measurement result display region 320 is checked, as illustrated in FIG. 25, in the captured image, a frame is added to a region corresponding to the selected cell image. The frame is the same frame as the frame added to the selected cell image in classification target display region 361. Since the frame is added to the captured image displayed in captured image region 325*a* in this way, the cell image selected in classification target display region 361 can be identified in the captured image. Therefore, the user can easily grasp a region of the classification target cell image on the captured image.

When another cell image is included in the captured image, a frame is also added to a region corresponding to the other cell image. The frame added to the other cell image is the same frame as the frame added to the other cell image in classification target display region 361. Therefore, the user can clearly distinguish and grasp the region of the classification target cell image and the region of the other cell image on the captured image displayed in captured image region 325*a*.

When check box 325*f* of measurement result display region 320 is checked, as illustrated in FIG. 25, below the frame added to the captured image in captured image region 325*a*, indication indicating how the cell image corresponding to the frame is classified is added. Classification corresponding to a selection button currently selected in large classification selection region 366 is added to the frame corresponding to the classification target cell image.

Since the captured image including the classification target cell image is displayed in captured image region 325*a* in this way, the user can grasp a state around the surroundings of the classification target cell image in the urine sample. Consequently, the user can smoothly and efficiently proceed with the classification of the cell images.

The urine sample includes particles, the same type of which tends to be present close to one another. For example, when crystals are included in the urine sample, it could often occur that another crystal is present around one crystal. Therefore, in the captured image displayed in captured image region 325*a*, if a cell image of another particle is present around the classification target cell image, by contrasting the cell image of the other particle and the classification target cell image, it is sometimes possible to smoothly proceed with determination whether the classification target cell image is the same kind as the other particle.

For example, even when, since the resolution of the classification target cell image is low, it is difficult to accurately determine that a particle appearing in the cell image is a crystal, if a cell image of another crystal having high resolution is present around the cell image, according to contrast with the cell image of the other crystal, it is sometimes possible to determine that the particle appearing in the classification target cell image is a crystal. Therefore, since the captured image including the classification target cell image is displayed in captured image region 325*a*, the user can smoothly and efficiently proceed with the classification of the cell images.

In the classification operation screen illustrated in FIG. 25, the captured image displayed in captured image region 325*a* does not always have to be one of the forty or eighty captured images acquired by image capturing apparatus 20. For example, an image having a predetermined breadth including the classification target cell image in the center may be generated from a captured image from which the classification target cell image is segmented and captured images before and after the captured image among the forty or eighty captured images. The generated image may be displayed in captured image region 325*a*. Then, even when a cell image is present in an end edge portion of a captured image acquired by image capturing apparatus 20, the cell image and the surroundings of the cell image can be satisfactorily displayed in captured image region 325*a*.

The user decides one cell image displayed in classification target display region 361 as a classification target and observes the cell image. According to the observation, the user determines large classification of the cell image and selects a selection button corresponding to the determined large classification from large classification selection region 366 via input unit 31 and presses the selection button. Subsequently, the user determines small classification of the cell image and selects a selection button corresponding to the determined small classification from small classification selection region 367 via input unit 31 and presses the selection button. Further, the user presses the cell image decided as the classification target via input unit 31. Consequently, the classification of the cell image is decided. According to the decision of the classification of the cell image, the result value in classification result display region 362 is updated.

After performing the classification of the cell images in this way, if an unclassified cell image remains, the user performs classification for the unclassified cell image according to the same operation as the operation explained above. After the classification is completed for all of the captured images displayed in captured image region 325*a*, when predetermined operation is performed, a classification result is registered in the database.

For example, operation button 334 is operated via input unit 31 by the user and the display target urine sample is changed, a dialog for urging saving of the classification result is displayed. A save button included in the dialog is pressed via input unit 31, whereby the classification result is registered in the database. Alternatively, after the classification operation screen illustrated in FIG. 25 returns to the list screen illustrated in FIG. 16 according to predetermined operation via input unit 31, when operation button 333 is pressed via input unit 31, a classification result is registered in the database. Operation for saving the classification result may be other operation.

As illustrated in FIG. 25, the classification operation screen includes classification target display region 361 for displaying cell images included in a class to which a classification instruction is input and measurement result display region 320 and further includes a classification operation region for inputting, via input unit 31, kinds of particles illustrated in the cell images displayed in classification target display region 361, that is, large classification selection region 366 and small classification selection region 367. Therefore, the user can properly evaluate the cell images displayed in classification target display region 361 based on various kinds of information obtained with reference to measurement result display region 320 and can efficiently and appropriately proceed with the classification of the cell images. Moreover, since the cell images and measurement results and the like are displayed on the same screen, the user can easily compare and contrast the cell images and measurement results. Consequently, it is possible to smoothly and efficiently proceed with the evaluation and the classification of the cell images.

Further, the classification operation screen includes, together with classification target display region 361 and measurement result display region 320, classification result display region 362 for displaying a classification result. Consequently, the user can confirm count values of particles while proceeding with the classification. Therefore, the user can quickly and smoothly grasp a diagnosis result of a condition of a disease.

Figure 26:
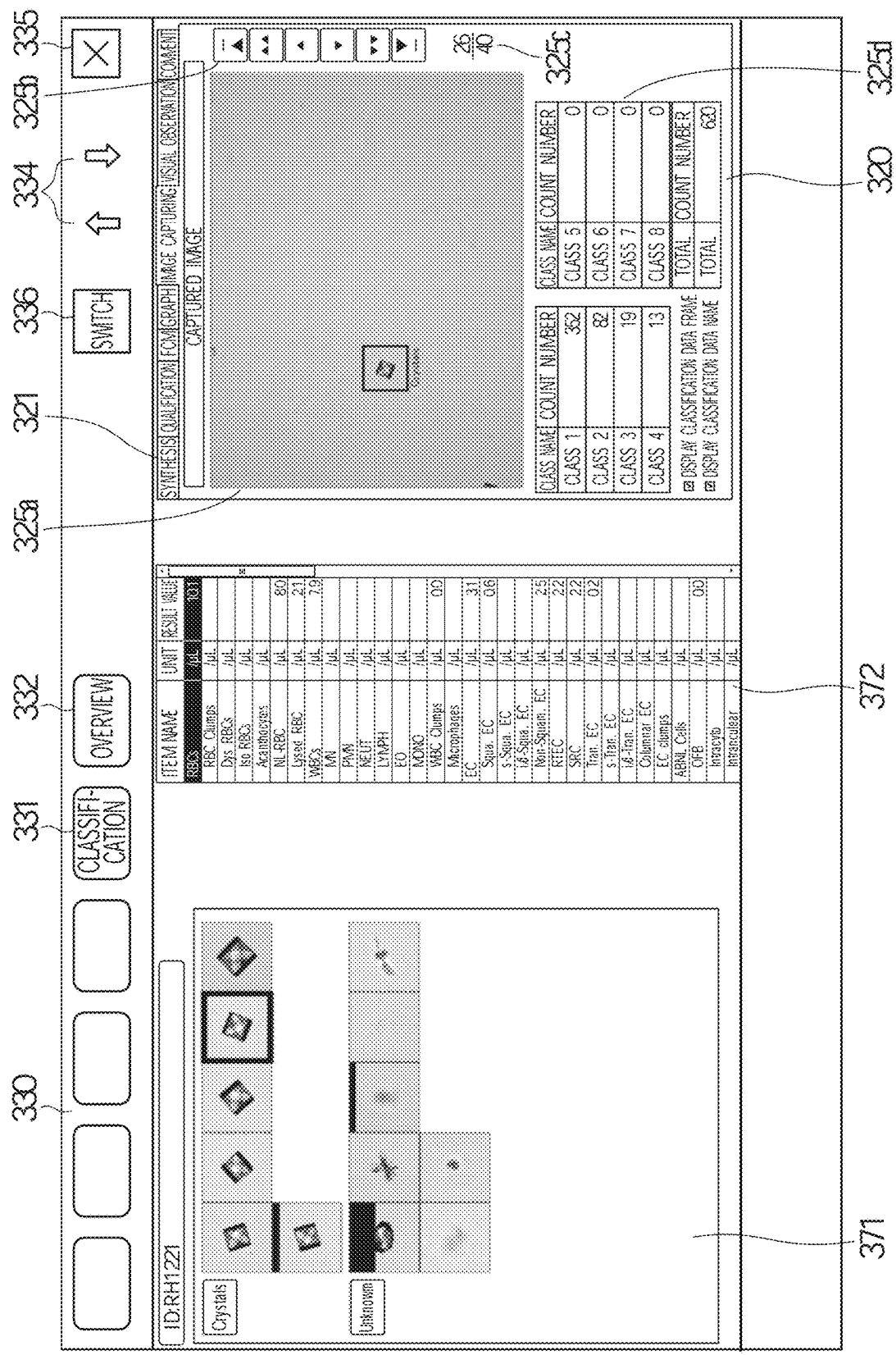
FIG. 26 is a diagram illustrating the configuration of a classification result screen according to the third embodiment.

In the classification operation screen illustrated in FIG. 25, when the operation button 335 is pressed via input unit 31, the screen is switched to a classification result screen illustrated in FIG. 26. This screen includes classified image display region 371 and classification result display region 372. In classified image display region 371, the cell images displayed in classification target display region 361 illustrated in FIG. 25 are divided by classification result and displayed for each classification result. In an example illustrated in FIG. 26, the cell images are divided into "Crystals" (crystal) and "Unknown" (unknown) and displayed. In classification result display region 372, as in the classification result display region illustrated in FIG. 25, a classification result of the cell images is displayed.

In captured image region 325a of measurement result display region 320, a captured image including the cell images selected in classified image displayed region 371 is displayed. When the selection of the cell image is changed in classified image display region 371, the captured image displayed in captured image region 325a is changed. In classified image display region 371, a frame indicating that the cell image is selected is added to the selected cell image.

In the classification result screen illustrated in FIG. 26, the user can switch the display content of measurement result display region 320 in the same manner as illustrated in FIGS. 17 to 23 by operating tab 321 via input unit 31. In the classification result screen illustrated in FIG. 26, the cell images are divided in classified image display region 371 using a classification result as an indicator. In this case as well, the user can evaluate the cell images displayed in classified image display region 371 from various viewpoints based on various kinds of information grasped from the display content of measurement result display region 320.

In the screen illustrated in FIG. 16, after a classified urine sample is selected, when operation button 332 is pressed via input unit 31, a classification result screen having the same layout as FIG. 26 is displayed. In this case, in classified image display region 371, the cell images are displayed in a manner divided into all particle classes. In this case, the user can switch the display content of measurement result display region 320 in the same manner as illustrated in FIGS. 17 to 23 by operating tab 321 via input unit 31. Therefore, the user can evaluate the classified cell images displayed in classified image display region 371 from various viewpoints based on various kinds of information grasped from the display content of measurement result display region 320.

Fourth Embodiment

Figure 27:
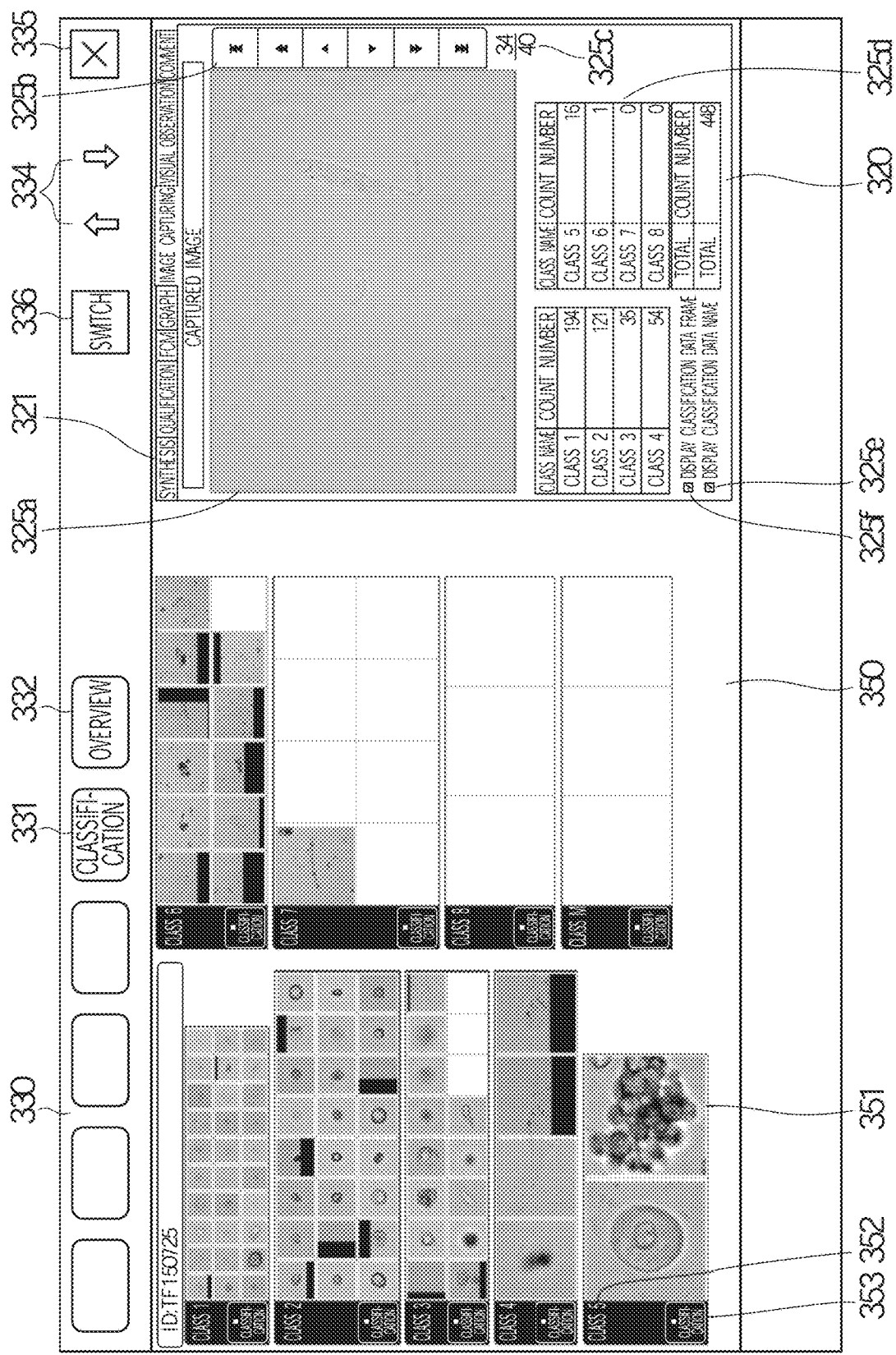
FIG. 27 is a diagram illustrating the configuration of an overview screen at the time when a tab of image capturing is pressed according to a fourth embodiment.

In a fourth embodiment, compared with the third embodiment, the user can manually segment cell images via input unit 31 in management apparatus 30 and classify segmented cell images. Differences from the third embodiment are explained below.

in the fourth embodiment, instead of the overview screen illustrated in FIG. 21, an overview screen illustrated in FIG. 27 is displayed. Specifically, in the list screen illustrated in FIG. 16, after one urine sample is selected in list display region 310 via input unit 31, when operation button 332 is pressed and image capturing tab 321 is selected, the screen of display unit 32 is switched to the overview screen illustrated in FIG. 27. In the overview screen illustrated in FIG. 27, compared with the overview screen illustrated in FIG. 21, a section of "class M" corresponding to a manually segmented cell image is added to cell image display region 350. Like the sections of classes 1 to 8, the section of class M includes region 351, label 352, and operation button 353.

The user performs operation explained below in order to manually segment a cell image. First, the user operate operation button 325b via input unit 31 to display a captured image in which a cell desired to be segmented appears in captured image region 325a. Subsequently, the user sets a region desired to be segmented on the captured image. For example, the user sets a region corresponding to a cell by designating opposed two vertexes of a rectangle or performing dragging between the opposed two vertexes via input unit 31.

Figure 28:
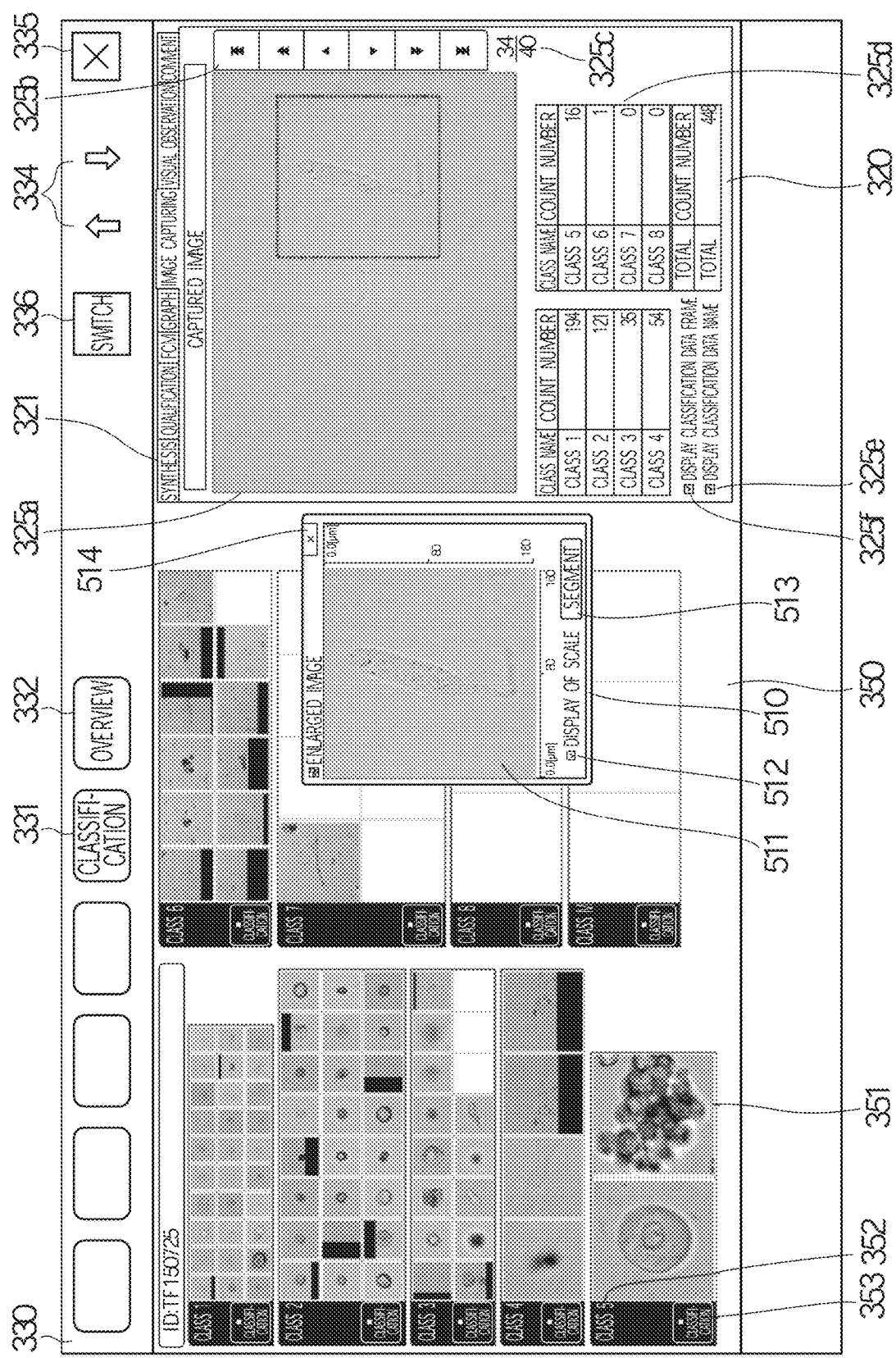
FIG. 28 is a diagram illustrating the configuration of an overview screen at the time when the tab of image capturing is pressed and the configuration of a dialog box for segmenting a cell image.

In the overview screen illustrated in FIG. 27, when region is set on the captured image in captured image region 325a, as illustrated in FIG. 28, dialog box 510 is popup-displayed. Dialog box 510 includes region 511, check box 512, segmentation button 513, and close button 514. In region 511, an image in the region set on the captured image is enlarged and displayed. Check box 512 is used to set whether a scale of the image displayed in region 511 is displayed.

Figure 29:
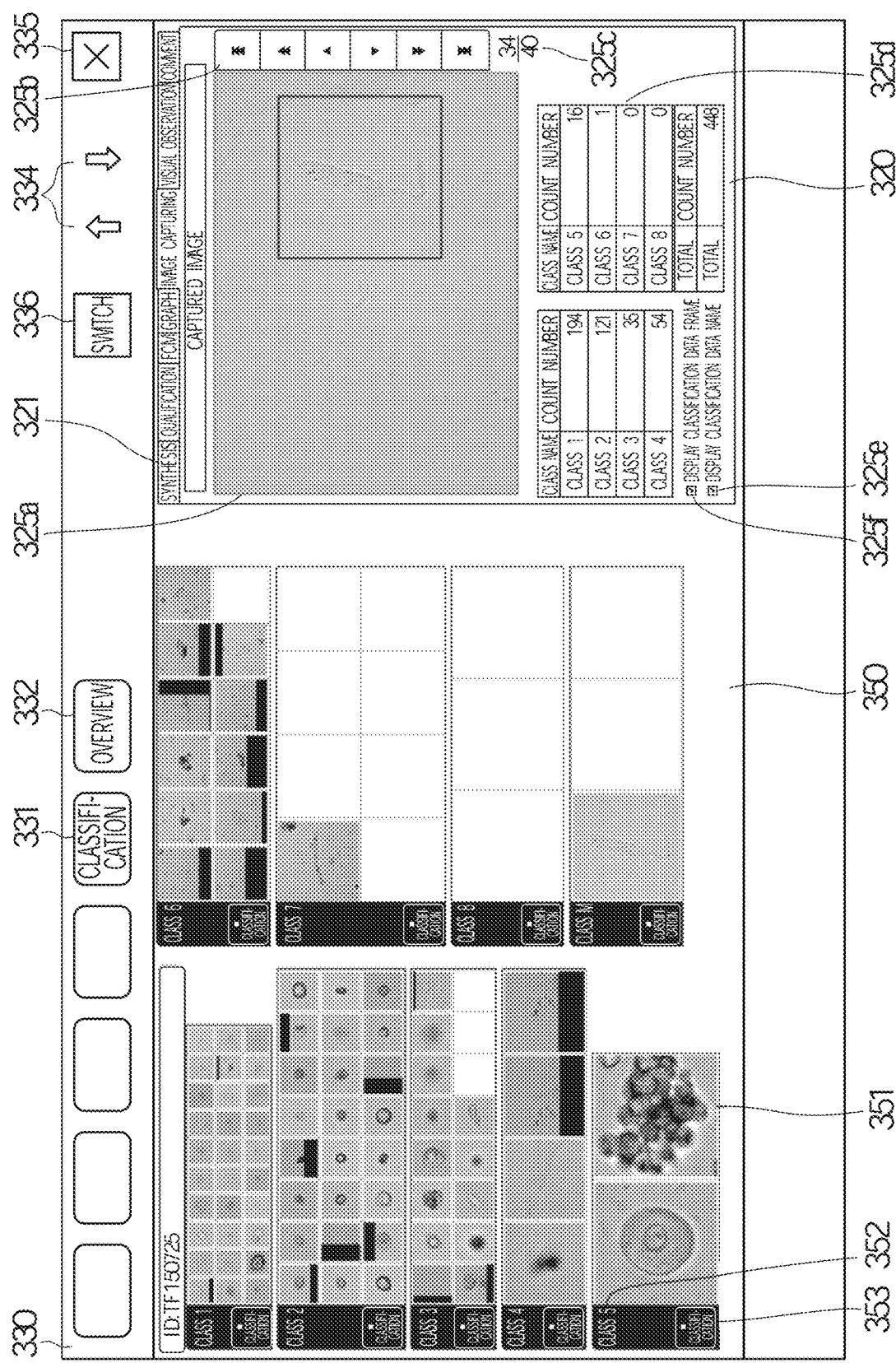
FIG. 29 is a diagram illustrating the configuration of an overview screen at the time when the tab of image capturing is pressed according to the fourth embodiment.

When the user presses segmentation button 513 via input unit 31, controller 33 of management apparatus 30 acquires the image in the region set on the captured image in captured image region 325a. Specifically, controller 33 registers the image in the region set on the captured image in captured image region 325a in the database constructed in storage 34 as an image corresponding to class M. As illustrated in FIG. 29, controller 33 displays, in region 351 corresponding to class M, as a segmented image, the image in the region set on the captured image in captured image region 325a and closes dialog box 510. When the user presses close button 514 via input unit 31, controller 33 releases the region set on the captured image in captured image region 325a and closes dialog box 510.

When the region is set on the captured image in captured image region 325a, controller 33 may acquire the image in the region of the captured image as a cell image without displaying dialog box 510.

As illustrated in captured image region 325a in FIG. 27, when identity of a cell is low because a luminance difference between the cell in a captured image and a background region is small, image capturing apparatus 20 sometimes cannot properly acquire a cell image from the captured image. However, when the cell image can be manually acquired from the captured image as explained above, a cell image that cannot be acquired by image capturing apparatus 20 can be acquired anew.

Subsequently, in an overview screen illustrated in FIG. 29, as in the case of the cell images of classes 1 to 8, the user can proceed with the classification of the cell image of class M. When the user presses operation button 353 of class M in cell image display region 350 via input unit 31, a classification operation screen illustrated in FIG. 30 is displayed.

Figure 30:
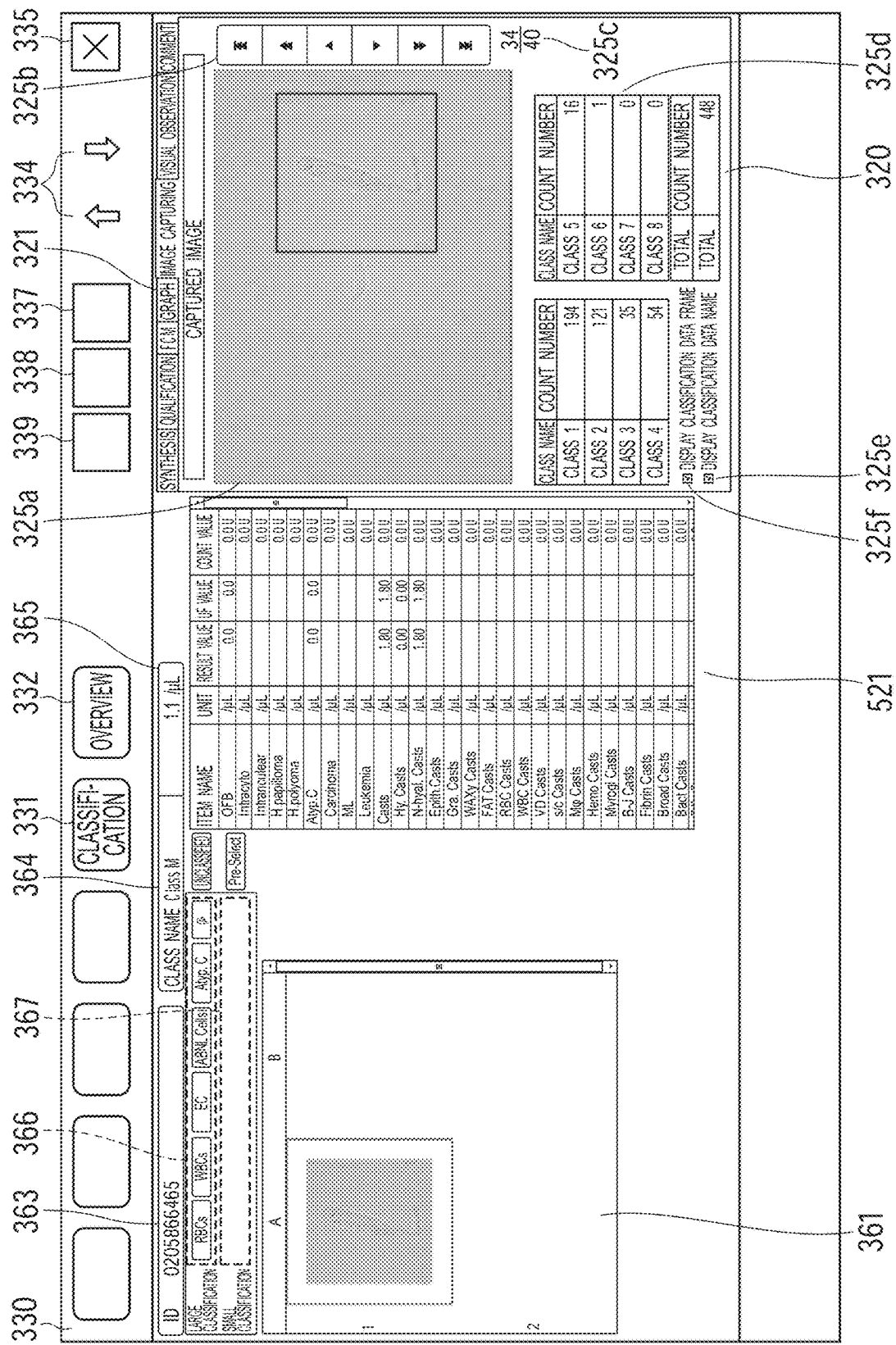
FIG. 30 is a diagram illustrating the configuration of a classification operation screen according to the fourth embodiment.

In the classification operation screen illustrated in FIG. 30, compared with the classification operation screen illustrated in FIG. 25, "Class M" is displayed in class display region 364. The cell image manually acquired as explained above is displayed in classification target display region 361. As in the third embodiment, for example, a frame of a predetermined color is added to the cell image in classification target display region 361 as a marking corresponding to a state of the classification. The user can popup-display an enlarged cell image by double-clicking the cell image in classification target display region 361 via input unit 31.

Note that, in the classification operation screen illustrated in FIG. 30, the user can set the region and segment the cell image as explained above from the captured image displayed in captured image region 325a.

In the classification operation screen illustrated in FIG. 30, compared with the classification operation screen illustrated in FIG. 25, classification result display region 521 is added instead of classification result display region 362. In classification result display region 521, compared with classification result display region 362 illustrated in FIG. 25, an item indicating a UF value and an item indicating a count value are added. As explained above, testing apparatus 10 performs measurement concerning measurement items and acquires a urinary sediment measurement result. The item indicating the UF value indicates a measurement result acquired in testing apparatus 10. The item indicating the count value indicates a count value of a particle calculated by classifying a cell image. Before the classification of the cell image is started, UF values are adopted as final result values in all of particles. Therefore, as illustrated in FIG. 30, "U" is displayed concerning all of the particles at the right end of the classification result display region 521.

The user selects a cell image in classification target display region 361 via input unit 31 and, then, as in the third embodiment, starts classification of the cell image. That is, the user determines large classification and small classification of the selected cell image and selects selection buttons corresponding to the determined large classification and the determined small classification from large classification selection region 366 and small classification selection region 367 and presses the selection buttons. Consequently, the classification of the cell image is decided. The display in classification result display region 521 is updated according to the decided classification.

Figure 31:
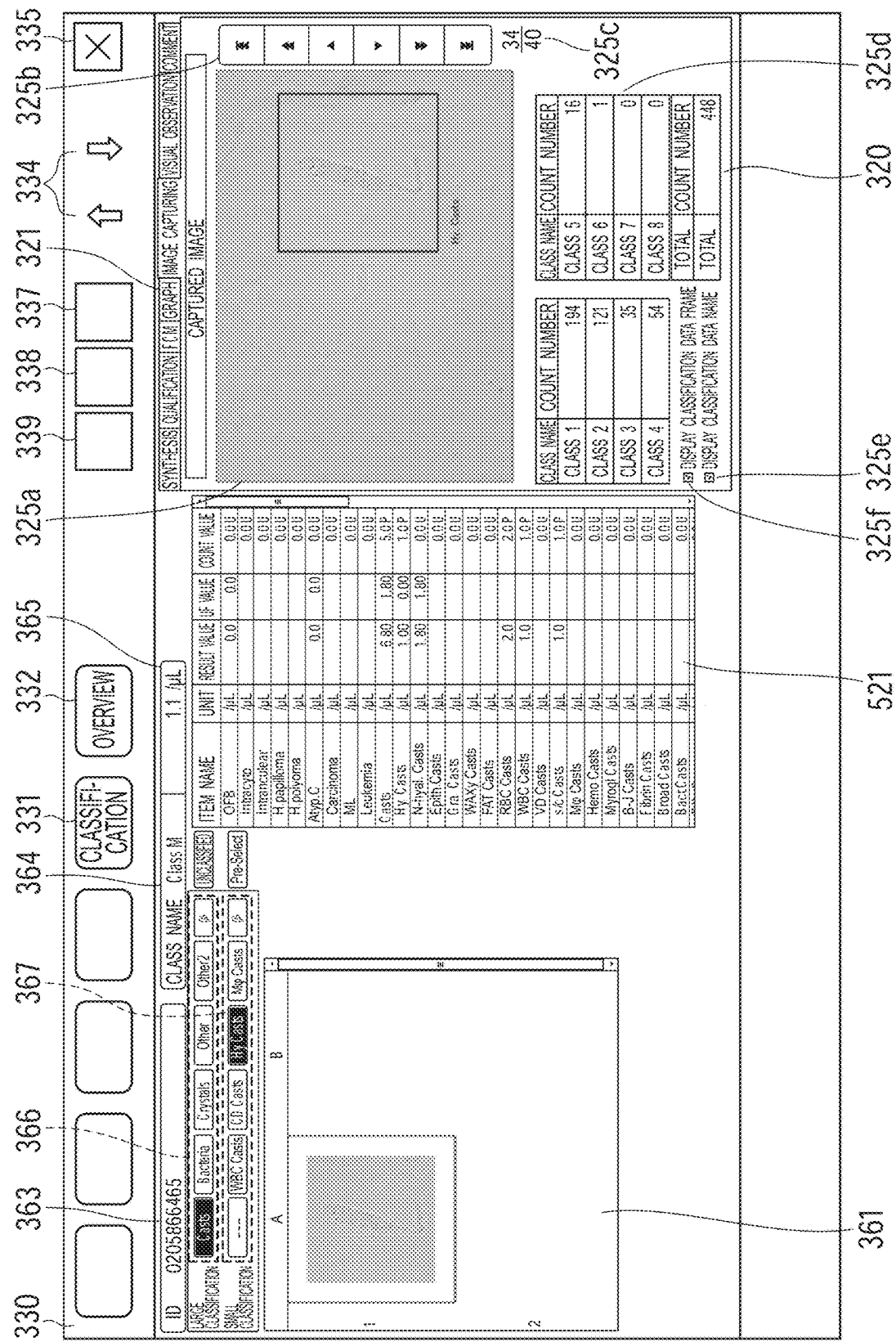
FIG. 31 is a diagram illustrating the configuration of the classification operation screen according to the fourth embodiment.

For example, as illustrated in FIG. 31, when "Casts" (a cast) and "HY. Casts" (a glass cast) are respectively selected as the selected large classification and the selected small classification of the cell image, a count value corresponding to "Hy. Casts" in classification result display region 521 is updated to, for example, "1.0". According to the update of the count value to "1.0", a result value of "Hy. Casts" is updated from "0.00" to "1.00". "P" indicating that the count value is adopted is displayed at the right end of classification result display region 521 instead of "U" indicating that the UF value is adopted.

Note that, when one cell image of class M is classified into a certain particle, a count value of the particle is updated to a value increased by 1/µl in the case of the normal mode and updated to a value increased by 0.5/µL in the case of the close inspection mode.

In an example illustrated in FIG. 31, count values are updated concerning items in which measurement results are not obtained in testing apparatus 10, that is, "RBC Casts" (a red blood cell cast), "WBC Casts" (a white blood cell cast), and "s/c Casts" (a salt crystal cast) in which UF values are blank. Results values are updated according to the update of the count values. "P" is displayed at the right end of classification result display region 521. A count value is updated to "5.0" according to the update of the count values concerning "Hy. Casts", "RBC. Casts", "WBC Casts", and "s/c Casts". "P" is displayed at the right end of classification result display region 521. A result value is updated to "6.80".

When the classification of the cell image of class M ends and predetermined operation concerning saving is performed, a result of the classification performed based on the cell image and the result values in classification result display region 521 are registered in the database. Note that, when classification of a cell image is performed via input unit 31 concerning the cell images of classes 1 to 8, as in the cell image of class M, content of classification result display region 521 is updated. A result of the classification performed based on the cell image and the result values in classification result display region 521 are registered in the database.

As illustrated in FIG. 31, when the cell image is classified into "Hy. Casts" via input unit 31, irrespective of the fact that a UF value of "Hy. Casts" obtained by testing apparatus 10 is "0.00", a count value of "Hy. Casts" calculated by the classification of the cell image via input unit 31 is adopted as a result value. That is, when the cell image is classified via input unit 31, the count value is reflected on the result value irrespective of the UF value.

In other words, concerning the kind of the particle classified by testing apparatus 10, when the kind of the particle is not received via input unit 31, controller 33 displays a UF value obtained by testing apparatus 10 on the screen as a result value. On the other hand, concerning the kind of the particle classified by testing apparatus 10, when the kind of the particle is received via input unit 31, controller 33 displays a count value calculated based on the kind of the particle received via input unit 31 on the screen as a result value. For example, in the example illustrated in FIG. 31, concerning "N-hyal. Casts" (a non-glass cast), a UF value of which is acquired, the cell image is not classified and a count value is not acquired. Therefore, concerning "N-hyal. Casts", a UF value "1.80" is displayed as a result value. On the other hand, concerning "Hy. Casts" (a glass cast), a UF value of which is acquired, the cell image is classified and a count value is acquired. Therefore, concerning "Hy. Casts", a count value "1.0" acquired by the classification of the cell image is displayed as a result value.

Consequently, even when reliability of a measurement result acquired by testing apparatus 10 is considered to be low, it is possible to improve reliability of a result value by classifying the cell image via input unit 31.

For example, as illustrated in FIG. 16, when "RBC/X'TAL discrimination error" is displayed in comment item 318 concerning the urine sample, the user often observes a red blood cell and a crystal appearing in a captured image. At this point, when a cell image is not properly generated concerning the red blood cell and the crystal, the user manually segments the cell image corresponding to the red blood cell and the crystal and classifies the segmented cell image. Consequently, in items corresponding to the red blood cell and the crystal in classification result display region 521, even if a UF value considered to be low in reliability is adopted as a result value, a count value based on the classification of the cell image is adopted as a result value. Therefore, it is possible to improve reliability of the result value. Note that, when reliability of a measurement result acquired by testing apparatus 10 is considered to be high, rather than the count value based on the classification of the cell image, a UF value only has to be adopted as a result value.

When a predetermined disease is suspected, it is also useful to manually segment a cell image and classify the segmented cell image.

For example, when urine protein is detected in second testing apparatus 60, there is a suspicion of chronic nephritis, glomerulonephritis, or interstitial nephritis. In this case, in order to estimate a progress degree and a part of the disease, the user often observes a cast appearing in a captured image. When a pathologic cast (a cellular cast) other than a glass cast such as a red blood cell cast or a white blood cell cast formed in a columnar shape by a red blood cell or a white blood cell, which leaks from a glomerulus, together with a protein component in a nephric tubule appears in the captured image, it is possible to determine that likelihood of glomerulonephritis is high. When a cell image is not properly generated concerning the pathologic cast, the user manually segments a cell image corresponding to the pathologic cast and classifies the segmented cell image. Consequently, as illustrated in FIG. 31, concerning "RBC Cats" and "WBC Casts", UF values of which are blank, result values are displayed. In this way, when a specific disease is suspicious, it is possible to manually segment a cell image as appropriate and acquire a necessary result value. Therefore, it is possible to accurately determine a disease.

Figure 32:
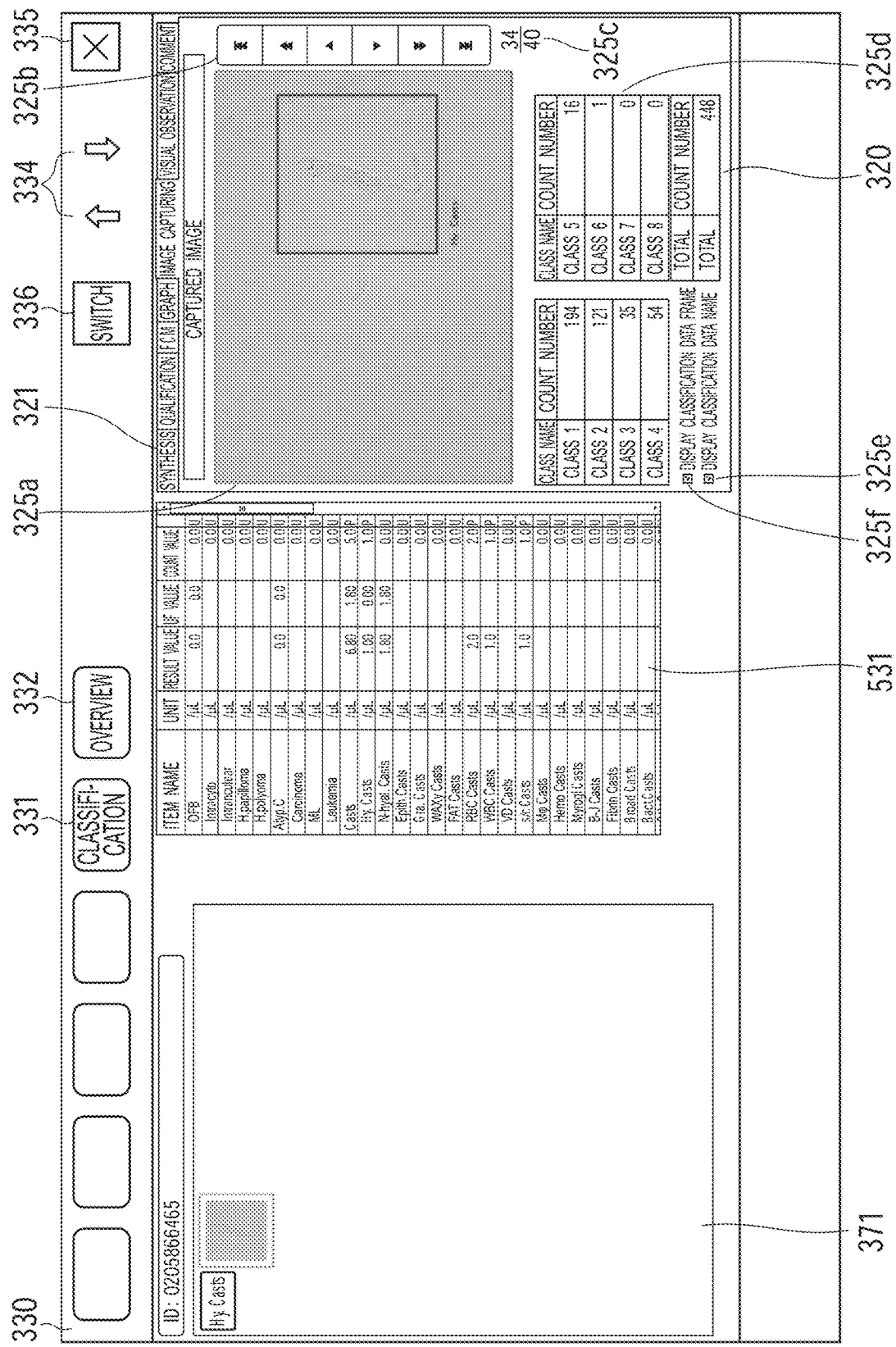
FIG. 32 is a diagram illustrating a classification result screen according to the fourth embodiment.

In the classification operation screen illustrated in FIG. 31, when the user presses operation button 335 via input unit 31, the screen is switched to a classification result screen illustrated in FIG. 32. In the classification result screen illustrated in FIG. 32, compared with the classification result screen illustrated in FIG. 26, classification result display region 531 is added instead of classification result display region 372. Classification result display region 531 is configured the same as classification result display region 521 illustrated in FIG. 31. In classified image display region 371, a cell image segmented by image capturing apparatus 20 and a manually segmented cell image are displayed together. Marking is added to the manually segmented cell image such that it is seen that the cell image is manually segmented. For example, a frame of a predetermined color is added to the manually segmented cell image.

In this way, in the fourth embodiment, as in the third embodiment, classification results of cell images can be displayed as a list. When a count value based on classification of a cell image is displayed as a result value, "P" is displayed at the right ends of classification result display regions 521 and 531. Consequently, the user can learn at a glance that the displayed result value is displayed based on the classification of the cell image.

Further, in the fourth embodiment, the user can display a designated value by simple input in the result value in classification result display regions 521 and 531. Simple inputs to both of classification result display regions 521 and 531 are the same procedure. Therefore, in the following explanation, for convenience, the simple input is executed on classification result display regions 521.

Figure 33:
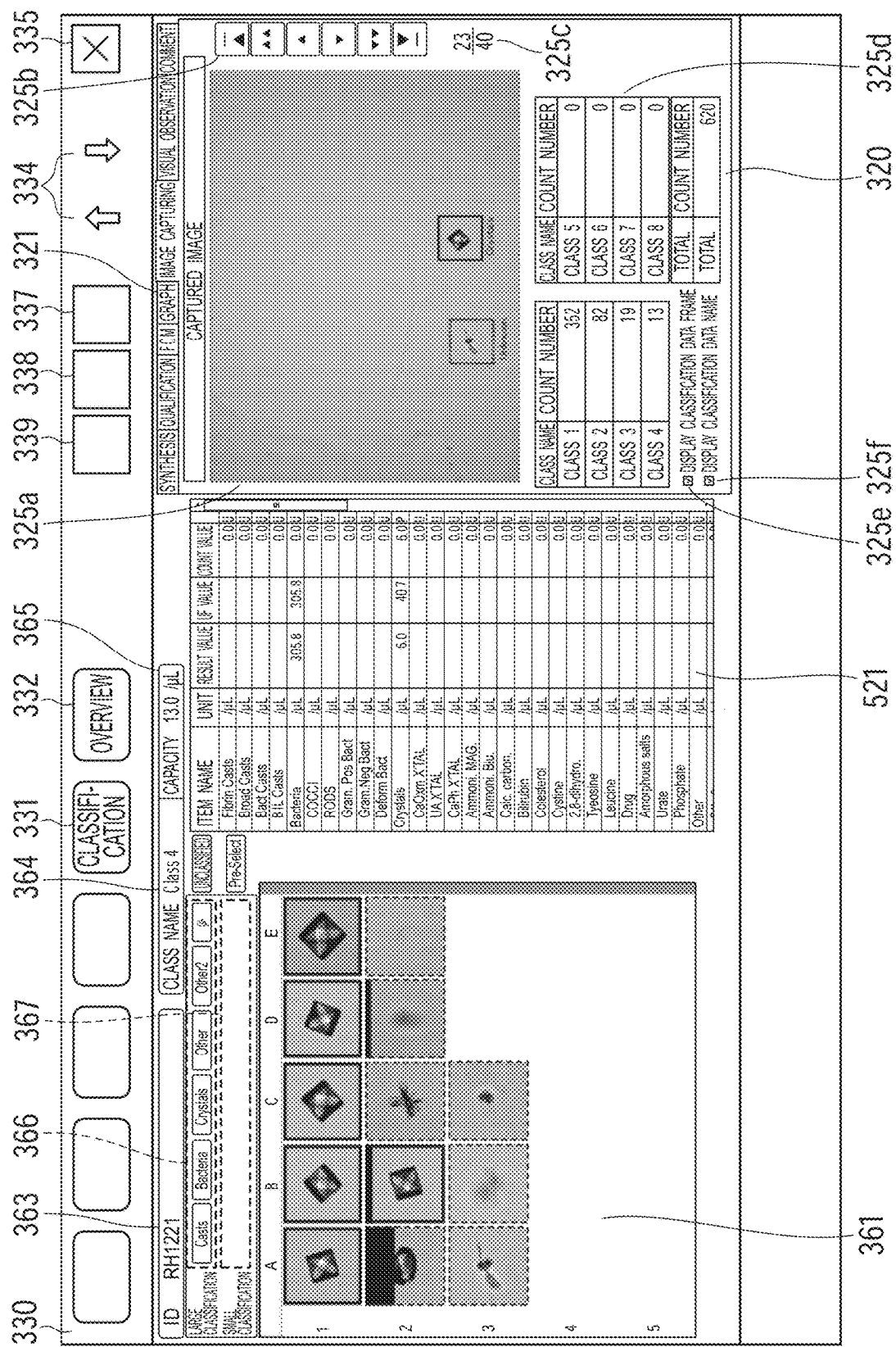
FIG. 33 is a diagram illustrating the configuration of the classification operation screen according to the fourth embodiment.
Figure 34:
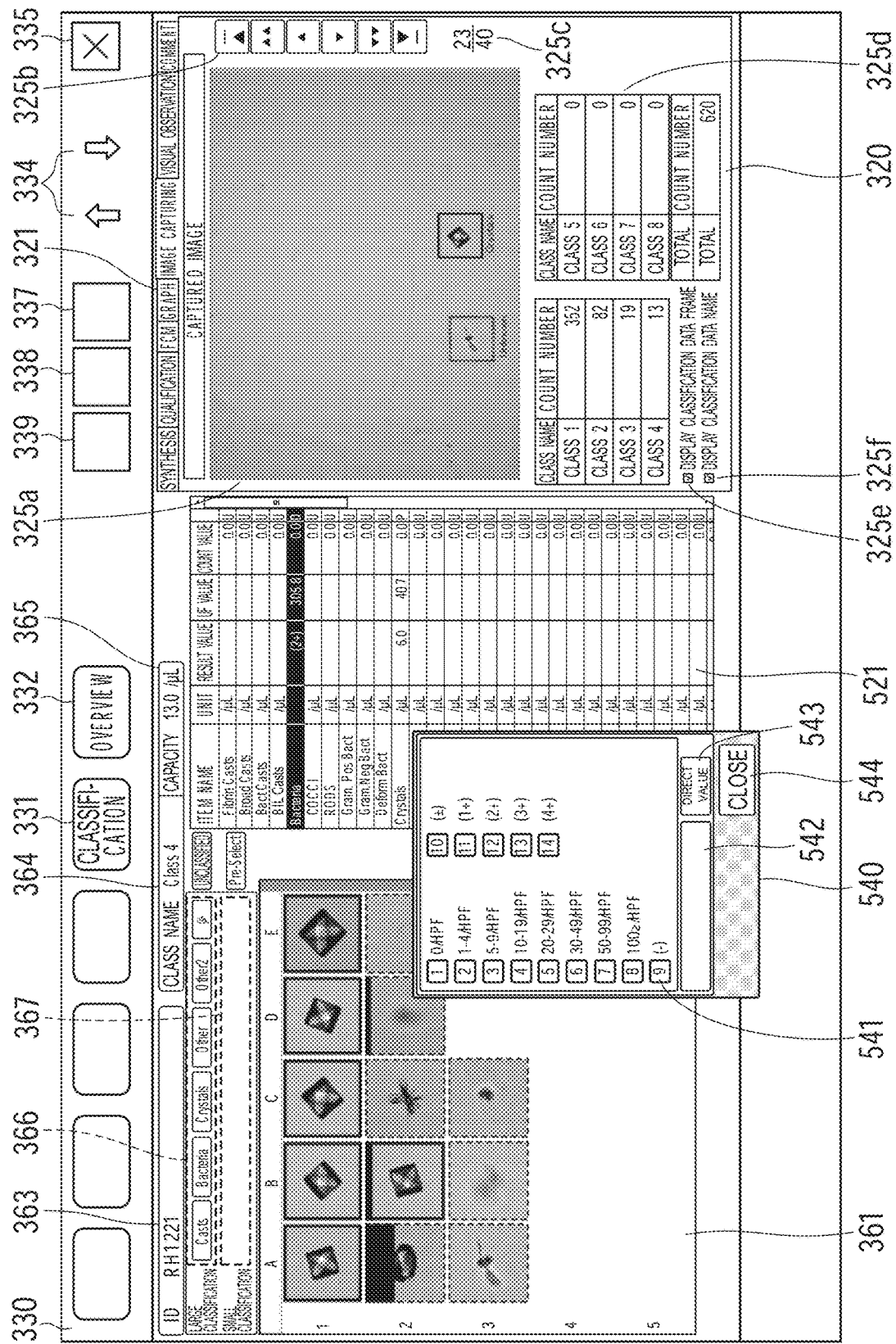
FIG. 34 is a diagram illustrating the configuration of the classification operation screen and the configuration of a dialog box for performing simple input according to the fourth embodiment.

FIG. 33 illustrates a classification operation screen corresponding to class 4. The classification operation screen has the same configuration as the configuration of the classification operation screen illustrated in FIG. 30. When a designated value by the simple input is adopted as a result value, the user double-clicks an item of a particle desired to be changed in classification result display region 521 via input unit 31. Consequently, a change target particle is determined. As illustrated in FIG. 34, dialog box 540 for changing a result value is popup-displayed. In an example illustrated in FIG. 34, a row corresponding to "Bacteria" (bacteria) is double-clicked. Dialog box 540 for changing a result value of "Bacteria" is displayed.

As illustrated in FIG. 34, dialog box 540 includes fourteen buttons 541, text box 542, direct value input button 543, and close button 544. Fourteen buttons 541 include buttons 541 with numbers 1 to 8 for inputting a semi-quantitative value and buttons 531 with numbers 9 to 14 for inputting a quantitative value. In the example illustrated in FIG. 34, as the semi-quantitative value, the number of pieces in a HPF (High Power Field) can be input. As the quantitative value, a degree of presence of a particle can be input. In dialog box 540, larger number of buttons 541 for inputting the numbers of pieces in a LPF (Low Power Field) and a WF (Whole Field) may be disposed to correspond to values desired to be input by the simple input.

For example, when the user presses button 541 with "12" via input unit 31, the change target result value is changed to "(2+)". When the user inputs a value to text box 542 via input unit 31 and presses direct value input button 543, the change target result value is changed to the value in text box 542. When the result value is changed by the simple input using dialog box 540, "D" indicating that the simple input is performed is displayed at the right end of a change target row. A unit of classification result display region 521 is changed to a unit of a value input by the simple input. In the example illustrated in FIG. 34, the result value of "Bacteria" is changed to "(2+)". Since the changed result value is a quantitative value, a unit of "Bacteria" is changed to none. When closing dialog box 540, the user presses close button 544 via input unit 31.

In this way, by using dialog box 540, the user can change result values in classification result display regions 521 and 531 without going through a procedure for segmenting and classifying respective cell images as explained above. Consequently, efficiency of a test is achieved. When the simple input is performed, "D" is displayed at the right ends of classification result display regions 521 and 531. Therefore, the user can learn at a glance that the displayed result value is input by the simple input.

When the simple input is performed, an input count value input by the simple input is reflected on a result value irrespective of a UF value. In other words, when a count value of a particle is not received via input unit 31 concerning a kind of a particle classified by testing apparatus 10, controller 33 displays a UF value obtained by testing apparatus 10 on the screen as a result value. On the other hand, when a count value of the particle is received via input unit 31 concerning the kind of the particle classified by testing apparatus 10, controller 33 displays the count value of the particle received via input unit 31 on the screen as a result value. Consequently, even when reliability of a measurement result acquired by testing apparatus 10 is considered to be low, it is possible to improve reliability of a result value by changing the result value with the simple input.

Fifth Embodiment

In a fifth embodiment, compared with the third embodiment, a screen design of a predetermined portion is different. As in the fourth embodiment, manual segmentation of cell images and classification of the cell images are possible. In the drawings referred to below, for convenience, portions having the same functions as the functions in the third and fourth embodiments are denoted by the same reference numerals and signs as the reference numerals and signs in the third and fourth embodiments.

The user performs operation explained below in order to perform the manual segmentation of cell images and the classification of the cell images. First, on the same overview screen as FIG. 17, the user presses operation button 353 via input unit 31 and further presses image captured tab 321 via input unit 31. Consequently, as illustrated in FIG. 35, a classification operation screen for classes is displayed.

Figure 35:
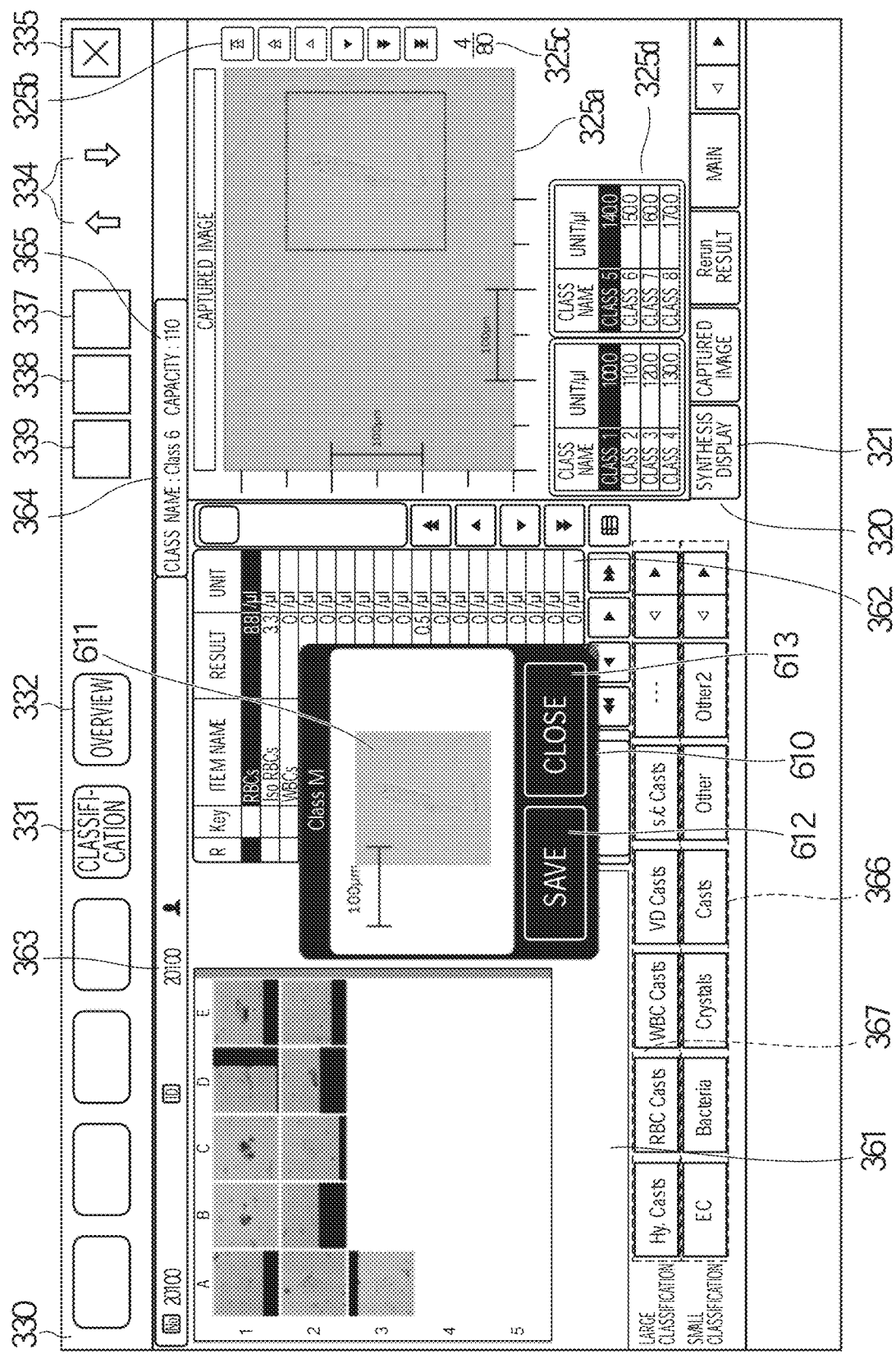
FIG. 35 is a diagram illustrating the configuration of a classification operation screen and the configuration of a dialog box for segmenting a cell image according to a fifth embodiment.

The classification operation screen illustrated in FIG. 35 corresponds to the classification operation screen illustrated in FIG. 25. In FIG. 35, tab 321 is disposed in a lower part of the screen and includes items such as synthesis display, a captured image, a Rerun result, and a main. In FIG. 35, large classification selection region 366 and small classification selection region 367 are disposed in a lower part of the screen. Like the item of the result value of classification result display region 362 illustrated in FIG. 25, an item of a result of classification result display region 362 illustrated in FIG. 35 indicates a result value.

Subsequently, the user operates operation button 325b via input unit 31 to display, in captured image region 325a, a captured image in which a cell desired to be segmented appears. The user determines a large classification and a small classification of the cell and, then, operates a selection button for large classification selection region 366 and a selection button for small classification selection region 367 via input unit 31 and selects classification. Consequently, controller 33 of management apparatus 30 receives the classification of the segmentation target cell. In an example illustrated in FIG. 35, a state is illustrated in which the segmentation target cell appears in captured image region 325a and a selection button corresponding to "Casts" (cast) of large classification selection region 366 and a selection button corresponding to "Hy. Casts" (glass cast) of small classification selection region 367 are pressed.

Subsequently, as in the fourth embodiment, the user sets a region desired to be segmented on the captured image via input unit 31. When the region is set on the captured image in captured image region 325a, as illustrated in FIG. 35, dialog box 610 is popup-displayed. Dialog box 610 includes region 611, save button 612, and close button 613. In region 611, an image in the region set on the captured image is enlarged and displayed. A scale of the image is displayed near region 611.

When the user presses save button 612 via input unit 31, controller 33 of management apparatus 30 registers the image in the region set on the captured image in captured image region 325a in the database constructed in the storage 34 as an image corresponding to class M. Controller 33 registers the classification of the cell received via large classification selection region 366 and small classification selection region 367 in the database. Controller 33 closes dialog box 610.

When the segmentation and the classification of cell images are performed, as in the fourth embodiment, controller 33 updates, according to the classification of the manually segmented cell, the result value in classification result display region 362 illustrated in FIG. 35. Note that, in the fifth embodiment, the manually segmented cell image is internally registered in the database as class M. However, the section of class M is not displayed on the overview screen.

After dialog box 610 is displayed, when the segmentation target cell image and the classification of the cell is not registered in the database, the user presses close button 613 via input unit 31. Consequently, controller 33 discards the region set on the captured image and the classification of the cell received via large classification selection region 366 and small classification selection region 367 and closes dialog box 610.

Figure 36:
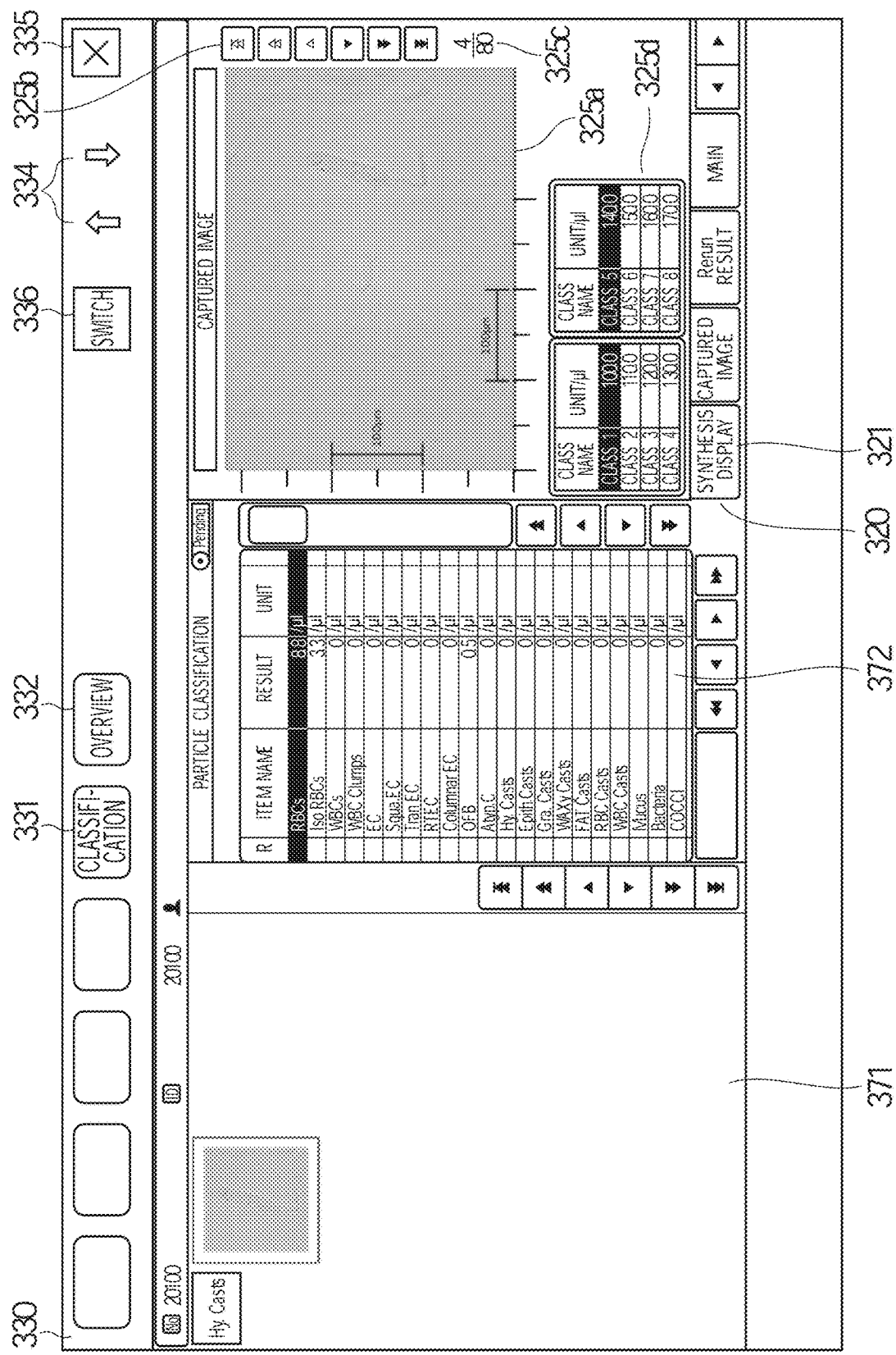
FIG. 36 is a diagram illustrating the configuration of a classification result screen according to the fifth embodiment.

On the classification operation screen illustrated in FIG. 35, when operation button 335 is pressed via input unit 31, the screen is switched to a classification result screen illustrated in FIG. 36. The classification result screen illustrated in FIG. 36 corresponds to the classification result screen illustrated in FIG. 26. In classified image display region 371 illustrated in FIG. 36, marking is added to the manually segmented cell image such that it is seen that the cell image is manually segmented. For example, a frame of a predetermined color is added to the manually segmented cell image.

In the fifth embodiment, as in the fourth embodiment, the user can update result values in classification result display regions 362 and 372 to designated values with simple input. Specifically, the user double-clicks items of particles desired to be changed in classification result display regions 363 and 372 via input unit 31. Consequently, as illustrated in FIG. 37A, dialog box 620 for changing a result value is popup-displayed.

Figure 37A:
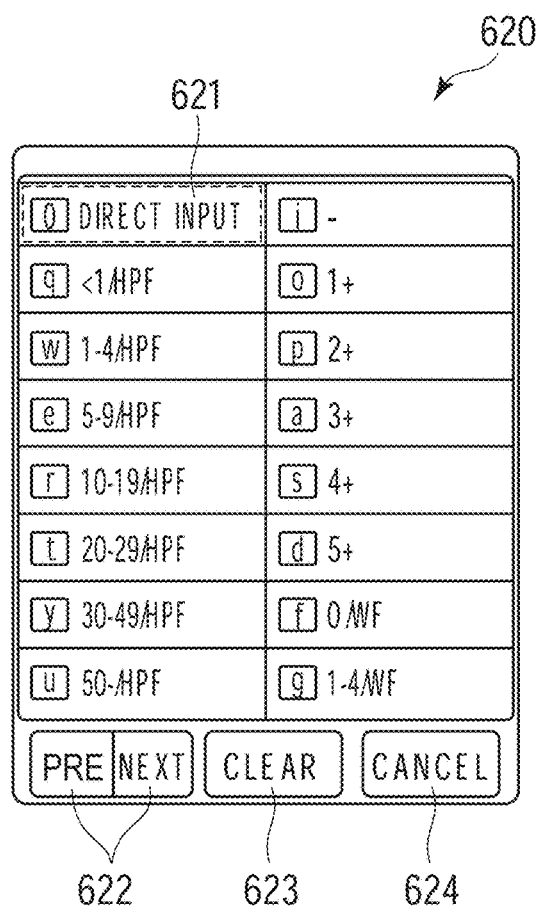
FIG. 37A is a diagram illustrating the configuration of a dialog box for performing simple input according to the fifth embodiment.
Figure 37B:
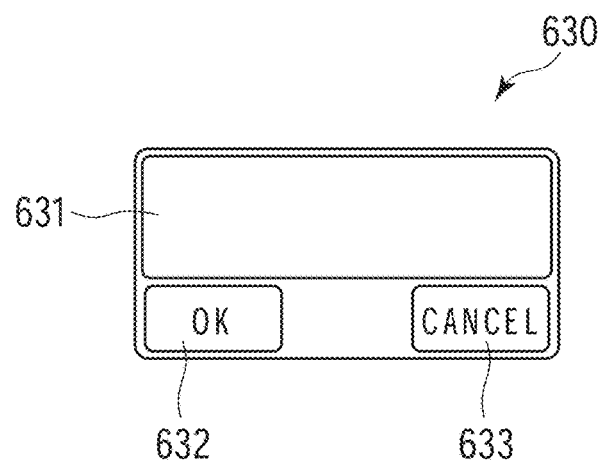
FIG. 37B is a diagram illustrating the configuration of a dialog box for performing direct input according to the fifth embodiment.

As illustrated in FIG. 37A, dialog box 620 includes sixteen buttons 621, two display change buttons 622, clear button 623, and cancel button 624. When the user presses button 621 for inputting a semi-qualitative value and a qualitative value via input unit 31, a change target result value is changed to a value corresponding to pressed button 621. When the user presses button 621 corresponding to direct input via input unit 31, dialog box 630 illustrated in FIG. 37B is further popup-displayed. When the user inputs a value to text box 631 of dialog box 630 via input unit 31 and presses OK button 632, the change target result value is changed to the value in the text box 631 and dialog box 630 is closed. When closing dialog box 630 illustrated in FIG. 37B, the user presses cancel button 633 via input unit 31.

When clearing the change target result value, the user presses clear button 623 of dialog box 620 via input unit 31. When switching button 621 disposed in dialog box 620 to button 621 for inputting another value, the user presses display change button 622 via input unit 31.

Validation in the Fourth and Fifth Embodiments

Controller 33 of control apparatus 30 is configured to be capable of setting validation for changing a sediment measurement result by testing apparatus 10, a qualitative measurement result by second testing apparatus 60, a result of a visual observation test, and a result of classification performed based on a cell image to states reportable to the outside. When performing the validation, the user operates a predetermined operation button of button region 330 via input unit 31 to display validate dialog 640 illustrated in FIG. 38.

Figure 38:
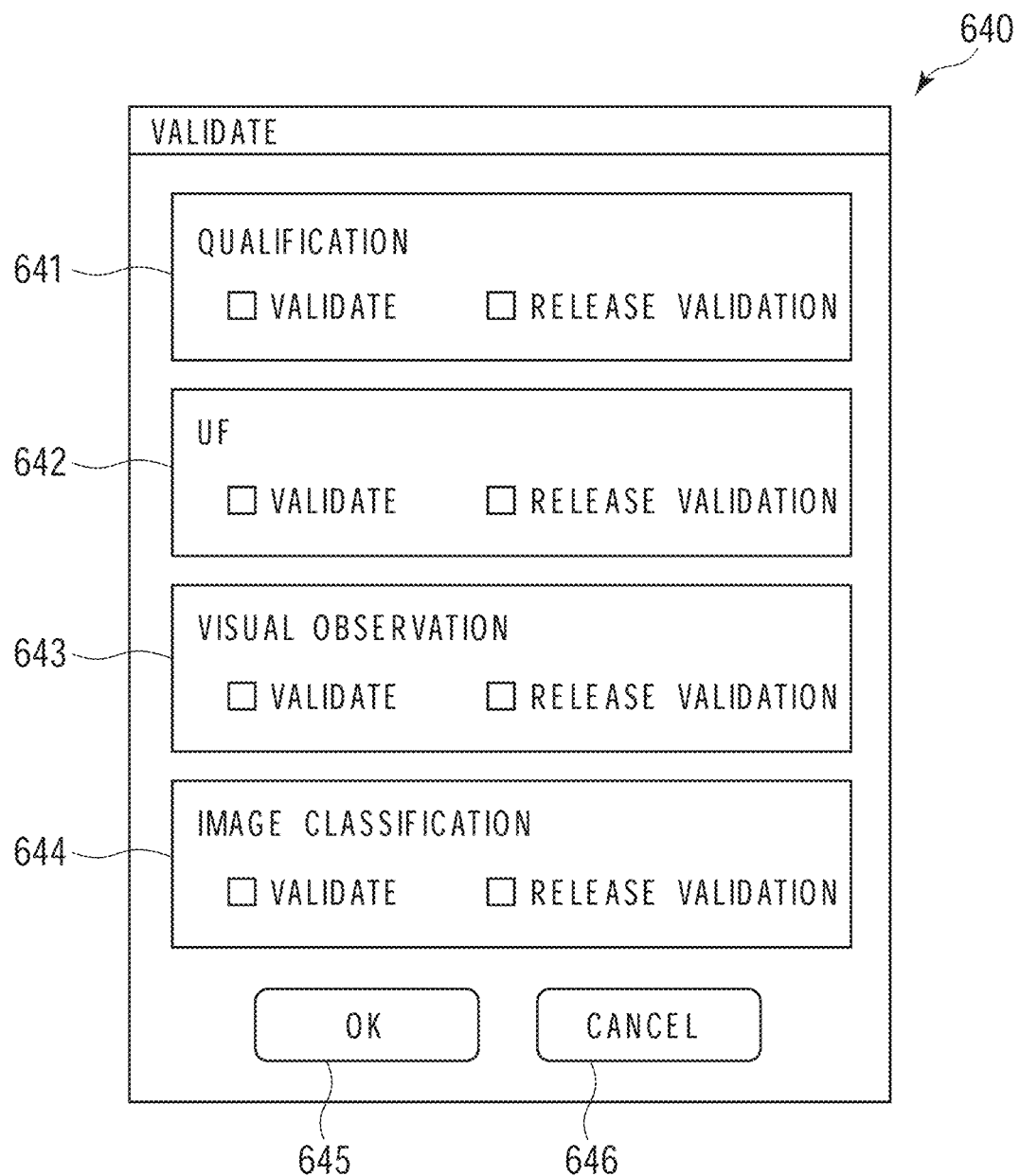
FIG. 38 is a diagram illustrating the configuration of a validate dialog according to the fourth and fifth embodiments.

As illustrated in FIG. 38, validate dialog 640 includes regions 641 to 644, OK button 645, and cancel button 646. Regions 641 to 644 respectively include check boxes for setting and releasing the validation with respect to a qualitative measurement result, a sediment measurement result, a result of a visual observation test, and a result of classification performed based on a cell image.

When performing the validation to change the results to the reportable states, the user checks the check boxes for setting the validation in regions 641 to 644 via input unit 31. When releasing the validation, the user checks the check boxes for releasing the validation in regions 641 to 644 via input unit 31. Note that regions 643 and 644 are configured such that only the check boxes in any one of the regions are operable. Consequently, the validation can be set and released for only any one of the result of the visual observation test and the result of the classification performed based on the cell image.

When the user presses OK button 645 via input unit 31, the validation is performed concerning a result of checking the check boxes for setting the validation. The validation is released concerning a result of checking the check boxes for releasing the validation. When the user presses cancel button 646 via input unit 31, the states of the check boxes are discarded. Validate dialog 640 is closed.

When the validation is performed concerning the qualitative measurement result, the sediment measurement result, and the result of the visual observation test, the result value displayed in qualitative result region 322 illustrated in FIG. 18, the result value displayed in sediment result region 323 illustrated in FIG. 19, and the result value in visual observation result region 326 illustrated in FIG. 22 are validated. When the validation is performed concerning the result of the classification performed based on the cell image, the result values displayed in classification result display regions 362, 372, 521, and 531 are validated. Specifically, controller 33 of management apparatus 30 registers indication that the setting and the releasing of the validation are performed in the database constructed in storage 34 in association with the result values.

The result values, on which the setting of the validation is performed in this way, are changed to states reportable to a doctor and the like or states viewable by the doctor and the like. For example, controller 33 transmits the result values, on which the validation is performed, to a host computer that receives viewing requests from other computers. Alternatively, controller 33 displays the result values, on which the validation is performed, on display unit 32 according to a viewing request of the doctors and the like.

The invention claimed is:

1. A urine analysis system comprising:
a testing apparatus that comprises a flow cell and that supplies a part of a urine sample in a sample container to the flow cell to measure particles included in the part of the urine sample according to a flow cytometry method;
an image capturing apparatus that comprises a cell, different from the flow cell of the testing apparatus, for accommodating another part of the urine sample retrieved from the sample container and that captures images of particles in the another part of the urine sample in the cell; and
a management apparatus that receives a measurement result obtained by the testing apparatus and the particle images captured by the image capturing apparatus, wherein
the management apparatus generates an image capturing order based on the measurement result obtained by the testing apparatus, and
the image capturing apparatus captures images of particles based on the image capturing order, and transmits the captured particle images to the management apparatus.

2. The urine analysis system according to claim 1, further comprising a conveyance apparatus that conveys a urine sample from the testing apparatus to the image capturing apparatus based on the image capturing order, wherein
the image capturing apparatus includes a suction unit that sucks the urine sample conveyed by the conveyance apparatus.

3. The urine analysis system according to claim 2, wherein
the conveyance apparatus includes:
a first conveyance path to convey a urine sample to the image capturing apparatus;
a second conveyance path to convey a urine sample wide bypassing the image capturing apparatus; and
a collection unit that collects a urine sample conveyed through the first conveyance path or the second conveyance path, and
the conveyance apparatus conveys, through the first conveyance path, a urine sample for which the image capturing order has been generated, whereas the conveyance apparatus conveys, to the collection unit through the second conveyance path, a urine sample for which the image capturing order has not been generated.

4. The urine analysis system according to claim 1, wherein
the testing apparatus includes:
a light source that irradiates the flow cell with light; and
a light receiver that receives light generated from a measurement specimen in response to the irradiation of the light, and
an amount of a urine sample supplied to the flow cell of the testing apparatus is larger than an amount of the urine sample introduced into the cell of the image capturing apparatus.

5. The urine analysis system according to claim 1, wherein the testing apparatus measures at least one of a red blood cell, a white blood cell, a yeast, an epithelial cell, a crystal, and a cast according to the flow cytometry method.

6. The urine analysis system according to claim 1, wherein
the image capturing apparatus is configured to selectively execute either of a normal mode for capturing a first number of images of the urine sample in the cell and a close inspection mode for capturing a second number of images of the urine sample in the cell, the second number being larger than the first number, and
the management apparatus generates an image capturing order for the normal mode when a measurement result of the particles obtained from the urine sample satisfies a first condition and generates an image capturing order for the close inspection mode when the measurement result satisfies a second condition.

7. The urine analysis system according to claim 6, wherein
the testing apparatus measures at least one of a cast and an epithelial cell according to the flow cytometry method, and
the management apparatus generates the image capturing order for the close inspection mode when a measurement result of the at least one of the cast and the epithelial cell obtained from the urine sample satisfies the second condition.

8. The urine analysis system according to claim 6, wherein
the image capturing apparatus includes a first cell and a second cell,
when the image capturing order for the normal mode is generated by the management apparatus, the image capturing apparatus introduces the urine sample into any one of the first cell and the second cell and executes the image capturing processing, and
when the image capturing order for the close inspection mode is generated by the management apparatus, the image capturing apparatus introduces the urine sample into both of the first cell and the second cell and executes the image capturing processing.

9. The urine analysis system according to claim 1, wherein the management apparatus includes a display unit and displays the measurement result and the captured particle images on the display unit.

10. The urine analysis system according to claim 9, wherein the management apparatus displays the measurement result and the particle image in one screen on the display unit.

11. The urine analysis system according to claim 9, wherein the management apparatus displays, as the measurement result on the display unit, a kind of each particle included in the urine sample, a count value thereof, and a scattergram indicating a distribution thereof.

12. The urine analysis system according to claim 9, wherein the management apparatus displays particle images obtained by the image capturing apparatus on the display unit with the particle images divided into classes defined by a predetermined indicator.

13. The urine analysis system according to claim 12, wherein the predetermined indicator is size of the particles.

14. The urine analysis system according to claim 1, further comprising a second testing apparatus that measures a chemical component in the urine sample using test paper, wherein
when a measurement value of the particles in the urine sample obtained by the testing apparatus exceeds a threshold or when a measurement value of the chemical component in the urine sample obtained by the second testing apparatus exceeds a second threshold, the management apparatus generates the image capturing order of the urine sample.

15. The urine analysis system according to claim 1, wherein the testing apparatus measures a first amount of urine sample, and the image capturing apparatus captures images of a second amount of urine sample, the second amount being smaller than the first amount.

16. The urine analysis system according to claim 1, wherein the testing apparatus detects light obtained by irradiating the particles in the urine sample, and distinguish the particles based on signal waveform of the detected light.

17. The urine analysis system according to claim 1, wherein the testing apparatus measures moving particles passing through the flow cell and the image capturing apparatus captures images of particles standing still in the cell.

18. An image capturing apparatus comprising:
a suction unit that comprises a tube and sucks a part of a urine sample;
an image capturer that comprises a cell that accommodates the part of the urine sample sucked by the suction unit and captures images of particles in the part of the urine sample in the cell; and
a controller comprising a processor configured with a program to perform operations comprising, in communication with a management apparatus that is programmed to generate an image capturing order based on a measurement result of particles included in another part of the urine sample measured by a testing apparatus under a flow cytometry, controlling the suction unit and the image capturer, wherein
the processor of the controller is configured with the program to perform operations further comprising:
receiving the image capturing order from the management apparatus;
causing the suction unit to suck the urine sample based on the received image capturing order; and
causing the image capturer to capture images of particles in the urine sample sucked by the suction unit based on received the image capturing order, and
the cell is different from a flow cell of the testing apparatus.

19. A urine analysis method comprising:
measuring particles included in a first part of a urine sample running in a flow cell according to a flow cytometry method;
automatically sucking a second part of the urine sample based on a measurement result of the particles and accommodating the second part of the urine sample in a cell that is different from the flow cell;
capturing images of particles in the second part of the urine sample; and
displaying the measurement result obtained by the flow cytometry method and the particle images in a comparable manner.

20. The urine analysis method according to claim 19, wherein the step of measuring particles comprises detecting light obtained by irradiating the particles in the urine sample and distinguishing the particles based on signal waveform of the detected light.

* * * * *